US006562854B2

(12) United States Patent
Church et al.

(10) Patent No.: US 6,562,854 B2
(45) Date of Patent: May 13, 2003

(54) COMPOSITIONS COMPRISING A SUBSTITUTED BENZIMIDAZOLE USEFUL FOR TREATING IMMUNOMEDIATED INFLAMMATORY DISORDERS

(75) Inventors: Timothy J. Church, Redwood City, CA (US); Neil Scott Cutshall, San Mateo, CA (US); Anthony R. Gangloff, Pacifica, CA (US); Thomas E. Jenkins, La Honda, CA (US); Martin S. Linsell, Foster City, CA (US); Joane Litvak, Oakland, CA (US); Kenneth D. Rice, Sausalito, CA (US); Jeffrey R. Spencer, San Mateo, CA (US); Vivian R. Wang, Redwood City, CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/874,412

(22) Filed: Jun. 4, 2001

(65) Prior Publication Data

US 2001/0053779 A1 Dec. 20, 2001

Related U.S. Application Data

(63) Continuation of application No. 08/980,515, filed on Dec. 1, 1997, now abandoned, which is a continuation-in-part of application No. 08/833,674, filed on Apr. 7, 1997, now abandoned, which is a continuation-in-part of application No. 08/357,491, filed on Dec. 14, 1994, now abandoned.

(51) Int. Cl.$^7$ ................... A61K 31/4184; C07D 403/06
(52) U.S. Cl. ..................... 514/394; 548/305.7
(58) Field of Search ........................ 548/305.7; 514/394

(56) References Cited

U.S. PATENT DOCUMENTS

| 3,105,837 | A |   | 10/1963 | Ursprung ................. 260/309.2 |
| 3,210,370 | A |   | 10/1965 | Ursprung ................. 260/309.2 |
| 3,324,050 | A |   | 6/1967 | Joo et al. ................. 548/305.7 |
| 4,074,046 | A |   | 2/1978 | Mohan ..................... 548/305.7 |
| 4,940,723 | A |   | 7/1990 | Tidwell et al. ............. 514/396 |
| 5,126,352 | A |   | 6/1992 | Ganguly et al. ............ 514/293 |
| 5,387,600 | A | * | 2/1995 | Aikawa et al. ............. 514/395 |
| 5,693,515 | A |   | 12/1997 | Clark et al. ................ 435/184 |

FOREIGN PATENT DOCUMENTS

| CA | 2104196 | 8/1993 | ......... C07D/403/14 |
| WO | WO92/20642 | 11/1992 | ........... C07C/43/21 |
| WO | WO93/23392 | 11/1993 | ......... C07D/403/12 |
| WO | WO94/27594 | 12/1994 | .......... A61K/31/30 |
| WO | WO95/08540 | 3/1995 | ......... C07D/235/20 |
| WO | WO95/19772 | 7/1995 | .......... A61K/31/415 |

OTHER PUBLICATIONS

Abraham et al., "Characterization of a late phase pulmonary response after antigen challenge in allergic sheep," *Am. Rev. Respir. Dis.* 128:839–844 (1983).

Allegra et al., "Duration of mucociliary dysfunction following antigen challenge," *J. Appl. Physiol.* 55: 726–730 (1983).

Castells et al., "Tryptase levels in nasal–lavage fluid as an indicator of the immediate allergic response," *J. Allergy Clin. Immunol.* 82:348–355 (1988).

Caughey et al., Substance P and Vasoactive Intestinal Peptide Degradation by Mast Cell Tryptase and Chymase, *J. Pharmacol. Exp. Ther.* 244:133–137 (1988).

Caughey, G.H., "The Structure and Airway Biology of Mast Cell Proteinases," *Am. J. Respir. Cell Mol. Biol.* 4:387–394 (1991).

Caughey et al., "Bis (5–amidino–2–benzimidazolyl) methane and related amidines are potent, reversible inhibitors of mast cell tryptases," *J. Pharmacol. Exp. Ther.* 264:676–682 (1993).

Chiu et al., "Gastric Cytoprotective Properties of SCH 32651, A Novel Antiulcer Agent," *Arch. Int. Pharmacodyn.* 270:128–140 (1984).

Fairley et al., "Structure, DNA Minor Groove Binding, and Base Pair Specificity of Alkyl–and Aryl–Linked Bis(amidinobenzimidazoles) and Bis(amidinoindoles)", *J. Med. Chem.* 36:1746–1753 (1993).

Franconi et al., "Mats Cell Tryptase and Chymase Reverse Airway Smooth Muscle Relaxation Induced by Vasoactive Intestinal Peptide in the Ferret," *J. Pharmacol. Exp. Ther.* 248 (3):947–951 (1989).

Geratz et al., "Streptococcal Cell Wall–Induced Systematic Disease" *American Journal of Pathology* 139(4):921–931 (1991).

Kalenderian et al., "Elevated Histamine and Tryptase Levels in Smokers' Bronchoalveolar Lavage Fluid—Do Lung Mast Cells Contribute to Smokers' Emphysena?" *Chest* 94:119–123 (1988).

Krebs et al., "Preparation of bis(imidazolyl) carbinols," (CA 117:150988), 1992, 2 pages.

Larsen, "Experimental Models of Reversible Airway Obstruction," *The Lung: Scientific Foundations*, 953–965 (1991).

(List continued on next page.)

*Primary Examiner*—Laura L. Stockton
(74) *Attorney, Agent, or Firm*—Towsnend and Townsend and Crew LLP

(57) ABSTRACT

Novel compounds, compositions and methods effective for the prevention and treatment of mast-cell mediated inflammatory disorders are described. The compounds, compositions and methods are effective for the prevention and treatment of inflammatory diseases associated with the respiratory tract, such as asthma and allergic rhinitis, as well as other types of immunomediated inflammatory disorders, such as rheumatoid arthritis, conjunctivitis and inflammatory bowel disease, various dermatological conditions, as well as certain viral conditions. The compounds comprise potent and selective inhibitors of the mast cell protease tryptase. The compositions for treating these conditions include oral, inhalant, topical and parenteral preparations as well as devices comprising such preparations.

16 Claims, 2 Drawing Sheets-

OTHER PUBLICATIONS

Miller et al., "Cloning and Characterization of Complementary DNA for Human Tryptase," *J. Clin. Invest.* 84: 1188–1195 (1989).

Miller et al., "Cloning and Characterization of a Second Complementary DNA for Human Tryptase," *J. Clin. Invest.* 86:864–870 (1990).

Muramatu et al., "Inhibitory effects of aryl trans–4 (aminomethyl) cyclohexanecarboxylate on serine proteases, and their antiallergic effects," *Hoppe–Seyler's Z. Physiol. Chem. Bd.* 363:203–211 (1982).

Russi et al., "Effects of leukotriene $D_4$ on mucociliary and respiratory function in allergic and nonallergic sheep," *J. Appl. Physiol.* 59: 1416–1422 (1985).

Ruoss et al., "Mast Cell Tryptase Is a Mitogen for Cultured Fibroblasts," *J. Clin. Invest.* 88:493–49 (1991).

Schwartz et al., "Tryptase Levels as an Indicator of Mast–Cell Activation in Sytematic Anaphylaxis and Mastocytosis," *N. Engl. J. Med.* 316:1622–1626 (1987).

"Neutral Proteases of Mast Cells" in *Monographs in Allergy*, vol. 27, pp. 52–66 (ed. L.B. Schwartz, Karger, NY), 1990.

Sekizawa et al., "Mast Cell Tryptase Causes Airway Smooth Muscle Hyperresponsiveness in Dogs," *J. Clin. Invest.* 83:175–179 (1989).

Slapke et al., "Protesase inhibitor prevents bronchoconstriction in man," *Eur. J. Resper. Dis.* 68:29–34 (1986).

Soler et al., "A PAF antagonist blocks antigen–induced airway hyperresponsiveness and inflammation in sheep," *J. Appl. Physiol.* 67:406–413 (1989).

Sturzebecher et al., "Inhibition of Human Mast Cell Tryptase by Benzamidine Derivatives," *Biol. Chem Hoppe–Seyler* 373:1025–1030 (1992).

Tam et al., "Degradation of Airway Neuropeptides by Human Lung Tryptase," *Am. J. Respir. Cell Mol. Biol.* 3:27–32 (1990).

Tidwell et al., "Aromatic Amidines: Comparison of Their Ability to Block Respiratory Syncytial Viru Induced Cell Fusion and to Inhibit Plasmin, Urokinase, Thrombin, and Trypsin," *J. Med. Chem.* 26:294–298 (1983).

Tidwell et al., "Diarylamadine Derivatives with One or Both of the Aryl Moieties Consisting of an Indol or Indol–like Ring. Inhibitors or Arginine–Specific Esterproteases" *Journal of Medicinal Chemistry* 21 (7) :613–623 (1978).

Tidwell et al., "Suppression of Respiratory Syncytial Virus Infection in Cotton Rats by Bis(5–Amidino–2–Benzimidazolyl) Methane," *Antimicrobial Agents and Chemotherapy* 26:591–593 (1984).

Vanderslice et al., Molecular Cloning of Dog Mast Cell Tryptase and a Related Protease: Structural Evidence of a Unique Mode of Serine Protease Activation, *Biochemistry* 28:4148–4155 (1989).

Vanderslice et al., "Human Mast cell tryptase: Multiple cDNAs and genes reveal a multigene serine protease family," *Proc. Natl. Acad. Sci. USA* 87:3811–3815 (1990).

Wang et al., "Synthesis of Bis–benzimidazoles", *J. Am. Chem. Soc.* 79:5706–5708 (1957).

Wanner et al., "Models of Airway Hyperresponsiveness," *Am. Rev. Respir. Dis.* 141:253–257 (1990).

Wenzel et al., "Activation of Pulmonary Mast Cells by Bronchoalveolar Allergen Challenge," *Am. Rev. Resp. Dis.* 141:1002–1008 (1988).

* cited by examiner

COMPOSITIONS COMPRISING A SUBSTITUTED BENZIMIDAZOLE USEFUL FOR TREATING IMMUNOMEDIATED INFLAMMATORY DISORDERS

FIELD OF THE INVENTION

This application is a continuation of Ser. No. 08/980,515 filed Dec. 1, 1997, now abandoned, which is a continuation-in-part of application Ser. No. 08/833,674, filed Apr. 7, 1997 now abandoned, which is a continuation-in-part of application Ser. No. 08/357,491, filed Dec. 14, 1994 now abandoned, which are herein incorporated by reference, and relates to compounds and compositions for treating diseases associated with serine protease, particularly tryptase, activity.

DESCRIPTION OF THE FIELD

Tryptase, the predominant protease secreted from human mast cells, is thought to be involved in neuropeptide processing and tissue inflammation. Tryptase concentrations are elevated in the bloodstream for several hours following anaphylaxis (Schwartz et al. (1987) *N. Eng. J. Med.* 316:1622-1626), are increased in nasal and lung lavage fluid from atopic subjects following specific antigen challenge (Castells et al. (1988) *J. Allerg. Clin. Immunol.* 141:563-568) and are elevated in lung lavage fluid of atopic asthmatics after endobronchial allergen challenge. Smokers often have striking elevations of bronchoalveolar lavage fluid tryptase levels, a finding that provides some support for the hypothesis that release of proteinase from activated mast cells could contribute to lung destruction in smoker's emphysema. (Celenteron et al. (1988) Chest 94:119–123). In addition, tryptase has been shown to be a potent mitogen for fibroblasts, suggesting that it is involved in pulmonary fibrosis and interstitial lung disease (Ross et al. (1991) *J. Clin. Invest.* 88:493–499).

Asthma is recognized as an inflammatory disorder (Hood et al. (1984) In: Benjamin-Cummings, ed. *Immunology* 2nd ed.) and frequently is characterized by progressive development of hyper-responsiveness of the trachea and bronchi to both immunospecific allergens and generalized chemical or physical stimuli. The disease involves multiple biochemical mediators in both its acute and chronic stages. The hyper-responsiveness of asthmatic bronchiolar tissue is believed to be the result of chronic inflammatory reactions, which irritate and damage the epithelium lining the airway wall and promote pathological thickening of the underlying tissue. Bronchial biopsies in patients with only mild asthma have features of inflammation in the airway wall.

Allergic responses to inhaled allergens can initiate the inflammatory sequence. For example, allergens can activate mast cells and basophils, which are present in the epithelium and underlying smooth muscle tissue by binding IgE located on the cell surface. Activated mast cells release a number of preformed or primary chemical mediators (e.g., histamine) of the inflammatory response and generate numerous other secondary mediators of inflammation (e.g., superoxide, lipid derived mediators, etc.) in situ. In addition, several large molecules (e.g., proteoglycans, tryptase, chymase, etc.) are released by degranulation of mast cells.

The release of these preformed mediators from mast cells probably accounts for the early bronchiolar constriction in the asthmatic reaction to air borne allergens. The early phase of the asthmatic reaction peaks approximately fifteen minutes after exposure to allergen and is generally followed by recovery over the ensuing one to two hours. Twenty five to thirty five percent of the patient population experience a further decline in respiratory function which maximizes six to twelve hours after exposure. This late reaction phase is accompanied by a marked increase in the number of inflammatory cells (e.g., eosinophils, neutrophils, lymphocytes, etc.) infiltrating the bronchiolar tissue. The infiltrating cells are attracted to the site by release of mast cell derived chemotactic agents and then become activated during the late reaction phase. The late asthmatic response is believed to be a secondary inflammatory reaction mediated in part by the secretory activity of granulocytes.

Tryptase is implicated in the degradation of vasodilating and bronchorelaxing neuropeptides (Caughey et al. (1988) *J. Pharmacol. Exp. Ther.* 244:133–137; Franconi et al. (1988) *J. Pharmacol. Exp. Ther.* 248:947–951; and Tam et al. (1990) *Am. J. Respir. Cell Mol. Biol.* 3:27–32) and modulation of bronchial responsiveness to histamine (Sekizawa et al. (1989) *J. Clin. Invest.* 83:175–179). These findings suggest that tryptase may increase bronchoconstriction in asthma by destroying bronchodilating peptides. Tryptase cleaves fibrinogen α-chains and high molecular weight kinninogen, which suggests that tryptase plays a role with heparin as a local anticoagulant. Tryptase activates prostromelysin (pro-MMP-3) and procollagenase (pro-MMP-1) via MMP-3, which suggests that tryptase is involved in tissue inflammation and remodeling and joint destruction in rheumatoid arthritis. Further, administration of tryptase inhibitor protects against development of the late and airway hyper-responsive phases in allergen challenged sheep (Clark et al. (1995) Am. *J. Respir. Crit. Care Med.* 152: 2076–2083) and inhibits the immediate cutaneous response to intradermal injection of allergen in allergic sheep (Molinari et al. (1995) *Amer. Physiol. Soc.* 79(6):1966–1970). All of the above-described findings clearly indicate the applicability of tryptase inhibitors as therapeutic agents in treating asthma and other disorders associated with inflammation of the respiratory tract.

The disclosures of these and other documents, including patents and patent applications, referred to throughout this application are incorporated herein by reference.

SUMMARY OF THE INVENTION

This application relates to a compound of Formula I:

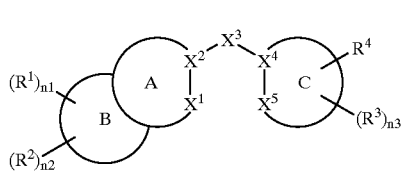

in which:

n1 is 0 or 1, n2 is 0, 1, 2, 3 or 4;

n3 is 0, 1, 2, 3 or 4;

A together with B comprises a fused heterobicyclic radical containing 8 to 12 annular atoms, wherein each ring contains 5 to 7 annular members, each annular atom optionally is a heteroatom, $X^1$ and $X^2$ are adjacent annular members of an aromatic ring and $X^1$ is a heteroatom moiety selected from —N=, —NR$^5$—, —O— and —S—, wherein $R^5$ is hydrogen, $(C_{1-6})$alkyl or hetero$(C_{2-6})$alkyl;

C comprises a fused heteropolycyclic radical containing 8 to 18 annular atoms, wherein each ring contains 5 to 7 annular members, each annular atom optionally is a heteroatom, $X^4$ and $X^5$ are adjacent annular members of an aromatic ring, $X^5$ is a heteroatom moiety selected from —N=, —$NR^5$—, and —S—, wherein $R^6$ is hydrogen, a group selected from $(C_{1-8})$alkyl or hetero$(C_{2-12})$alkyl, which group optionally is substituted with one to two substituents independently selected from $(C_{1-6})$alkanoyloxy, $(C_{1-6})$alkylamino, di$(C_{1-6})$alkylamino, tri$(C_{1-6})$alkylammonio, $(C_{1-6})$alkylcarbamoyl, di$(C_{1-6})$alkylcarbamoyl, $(C_{1-6})$alkyloxy, $(C_{1-6})$alkyloxycarbonyl, $(C_{1-6})$alkyloxysulfonyl, amino, carboxy, carbamoyl, $(C_{6-14})$aryl, halo, hetero$(C_{5-14})$aryl, hydroxy and sulfo, or as defined below; and any carbocyclic ketone, thioketone and iminoketone derivative thereof;

$X^3$ is —O—, —S—, —S(O)—, —S(O)$_2$—, —C(O)—, —$NR^7$— or —$CR^7R^8$—, wherein $R^7$ is hydrogen, $(C_{1-6})$alkyl, hetero$(C_{2-12})$alkyl or together with $R^6$ forms $(C_{2-4})$alkylene or hetero$(C_{2-4})$alkylene and $R^8$ is hydrogen, $(C_{1-6})$alkyl or hydroxy or together with $R^7$ forms $(C_{2-6})$alkylene or $(C_{1-6})$alkylidene, wherein any aliphatic or alicyclic moiety comprising $R^7$ and/or $R^8$ optionally are substituted with one to three substituents selected from $(C_{1-6})$alkylamino, di$(C_{1-6})$alkylamino, tri$(C_{1-6})$alkylammonio, $(C_{1-6})$alkyloxy, $(C_{1-6})$alkyloxycarbonyl, $(C_{1-6})$alkanoyloxy, amino, carboxy, carbamoyl, $(C_{1-6})$alkylcarbamoyl, di$(C_{1-6})$alkylcarbamoyl, halo and hydroxy;

$R^1$ is amino($N_{1-4}$)azolidinyl, amino($N_{1-4}$)azolyl, ($N_{1-4}$)azolidinyl, ($N_{1-4}$)azolyl, carbamoyl, cyano, —(CH$_2$)$_x$NHC(NR$^9$)R$^9$, —(CH$_2$)$_x$NHC(NH)NR$^9$R$^9$, —(NR$^9$)R$^9$, —C(NH)NHR$^{10}$, —C(NH)NR$^{10}$R$^{10}$ or —(CR$^{11}$R$^{11}$)$_y$NH$_2$ and bonded to any annular atom with an available valence comprising B, wherein x is 0 or 1, y is 0, 1, 2 or 3, each $R^9$ independently is hydrogen or $(C_{1-6})$alkyl, each $R^{10}$ is independently $(C_{1-6})$alkyl and each $R^{11}$ independently is hydrogen, $(C_{1-3})$alkyl or together with another $R^{11}$ and a carbon atom to which both are attached forms cyclopropyl, wherein any aliphatic or alicyclic moiety comprising $R^1$ optionally is substituted with one to two substituents independently selected from $(C^{1-6})$alkyloxycarbonyl, $(C_{1-6})$alkanoyloxy, carboxy, carbamoyl, $(C_{1-6})$alkylcarbamoyl, di$(C_{1-6})$alkylcarbamoyl, $(C_{1-6})$alkylsulfonyl and hydroxy;

each $R^2$ independently is $(C_{1-6})$alkyl, $(C_{1-6})$alkyloxycarbonyl, $(C_{1-6})$alkanoyloxy, $(C_{1-6})$alkyloxy, carboxy, carbamoyl, $(C_{1-6})$alkylcarbamoyl, di$(C_{1-6})$alkylcarbamoyl, $(C_{1-6})$alkylsulfinyl, $(C_{1-6})$alkylsulfonyl, $(C_{1-6})$alkylthio, halo or hydroxy and bonded to any annular atom with an available valence comprising B, wherein any aliphatic moiety comprising $R^2$ optionally is substituted with one to two substituents independently selected from $(C_{1-6})$alkyloxycarbonyl, $(C_{1-6})$alkanoyloxy, carboxy, carbamoyl, $(C_{1-6})$alkylcarbamoyl, di$(C_{1-6})$alkylcarbamoyl, $(C_{1-6})$alkylsulfonyl and hydroxy;

each $R^3$ independently is $(C_{1-6})$alkyl, $(C_{1-6})$alkyloxy, $(C_{1-6})$alkylthio, cyano, halo, perhalo$(C_{1-6})$alkyl or hydroxy and bonded to any annular atom with an available valence comprising C; and $R^4$ is —$R^{12}$, —$OR^{12}$, —$N(R^{13})R^{12}$, —$SR^{12}$, —$S(O)R^{12}$, —$S(O)_2R^{12}$, —$S(O)_2OR^{12}$, —$S(O)_2N(R^{13})R^{12}$, —$N(R^{13})S(O)_2R^{12}$, —$C(O)R^{12}$, —$C(O)OR^{12}$, —$C(O)N(R^{13})R^{12}$, —$N(R^{13})C(O)R^{12}$, —$OC(O)N(R^{13})R^{12}$, —$N(R^{13})C(O)OR^{12}$, —$CH_2)_zN(R^{13})C(O)N(R^{13})R^{12}$, —$OP(O)(OR^{13})O\ R^{12}$ or —$C(O)N(R^{14})CH(COOH)R^{12}$ and bonded to any annular carbon atom with an available valence comprising C, wherein:

z is 0, 1 or 2, $R^{12}$ is —$R^{15}$ or —$X^6$—$R^{15}$)$_{n15}$, wherein n15 is 1 or 2, $X^6$ is $(C_{1-10})$alkylene, cyclo$(C_{3-10})$alkylene, hetero$(C_{2-10})$alkylene or heterocyclo$(C_{3-10})$alkylene and each $R^{15}$ is independently hydrogen, $(C_{6-14})$aryl, cyclo$(C_{3-14})$alkyl, polycyclo$(C_{6-14})$aryl, heteropolycyclo$(C_{6-14})$aryl, heterocyclo$(C_{3-14})$alkyl, hetero$(C_{5-14})$aryl or as defined below, $R^{13}$ is hydrogen, $(C_{1-6})$alkyl or hetero$(C_{2-6})$alkyl;

$R^{14}$ is hydrogen, $(C_{1-6})$alkyl or together with $X^6$ and $R^{15}$ forms $(C_{3-4})$alkylene;

any aliphatic and alicyclic moiety comprising $R^4$ optionally is substituted with one to five substituents independently selected from $(C_{1-6})$alkyl, $(C_{1-6})$alkylamino, di$(C_{1-6})$alkylamino, $(C_{1-6})$alkylcarbamoyl, di$(C_{1-6})$alkylcarbamoyl, $(C_{1-6})$alkyloxy, $(C_{1-6})$alkyloxycarbonyl, $(C_{1-6})$alkylsulfinyl, $(C_{1-6})$alkylsulfonyl, $(C_{1-6})$alkythio, amino, $(C_{6-10})$arylsulfonyl, carbamoyl, carboxy, cyano, guanidino, halo, hydroxy, mercapto and uriedo; and any aromatic moiety comprising $R^{15}$ optionally is substituted with one to three substituents independently selected from cyano, guanidino, halo, halo-substituted $(C_{1-8})$alkyl, —$R^{16}$, —$OR^{16}$, —$SR^{16}$, —$S(O)_2R^{16}$, —$S(O)_2R^{16}$, —$S(O)_2N(R^{13})R^{16}$—, —$C(O)R^{16}$, —$C(O)OR^{16}$ and —$C(O)N(R^3)R^{16}$, wherein $R^{13}$ is as defined above and $R^{16}$ is hydrogen, optionally mono-substituted $(C_{1-8})$alkyl (wherein the optional substitutent is $(C_{1-6})$alkylamino, di$(C_{1-6})$alkylamino, tri$(C_{1-6})$alkylammonio, $(C_{1-6})$alkylcarbamoyl, di$(C_{1-6})$alkylcarbamoyl, $(C_{1-6})$alkyloxycarbonyl, $(C_{1-6})$alkyloxysulfonyl, amino, carboxy, carbamoyl, hydroxy or sulfo), cyclo$(C_{3-6})$alkyl, hetero$(C_{1-8})$alkyl, hetero$(C_{1-6})$aryl, heterocyclo$(C_{3-6})$alkyl or phenyl;

with the proviso that n1 is not 0, when n2 is 0 or $R^2$ is $(C_{1-6})$alkyl or $(C_{1-6})$alkyloxy, n3 is 0 or $R^3$ is $(C_{1-6})$alkyl or $(C_{1-6})$alkyloxy and $R^4$ is hydrogen, $(C_{1-10})$alkyl or $(C_{1-10})$alkyloxy; and the N-oxide derivatives, prodrug derivatives, protected derivatives, individual isomers, mixtures of isomers and pharmaceutically acceptable salts thereof.

The present invention also provides for pharmaceutical compositions of the compounds of the invention. These pharmaceutical compositions can be in a variety of forms including oral dosage forms, inhalable forms, as well as injectable and infusible solutions. When used in inhalant or aerosol form, the compounds of the present invention are used in combination with a pharmaceutically acceptable carrier solution or dry powder which can be converted into aerosol form. Similarly, when used in oral administration, the compounds of the present invention are used in combination with a pharmaceutically acceptable carrier suitable for such oral administration. When used for the treatment of immunomediated inflammatory skin conditions, the compounds of the present invention are used in combination with a non-toxic, pharmaceutically acceptable topical carrier. The compounds of the present invention can be used in combination with antiinflammatories or other asthma therapies, such as β-adrenergic agonists, antiinflammatory corticosteroids, anticholinergics, bronchodilators such as methyl xanthenes and the like.

The compounds described herein are useful for the prevention and treatment of immunomediated inflammatory disorders, and particularly those associated with the respiratory tract, including asthma, and particularly the hyperresponsiveness phase associated with chronic asthma, and allergic rhinitis. Thus, the present invention also provides a method for treating immunomediated inflammatory disorders wherein a patient having an immunomediated inflammatory disorder is administered a therapeutically effective dose or amount of a compound of the present invention. Further, the compounds described herein are useful for treating syncytial viral infections.

DETAILED DESCRIPTION OF THE INVENTION

Definitions

Figure 1:
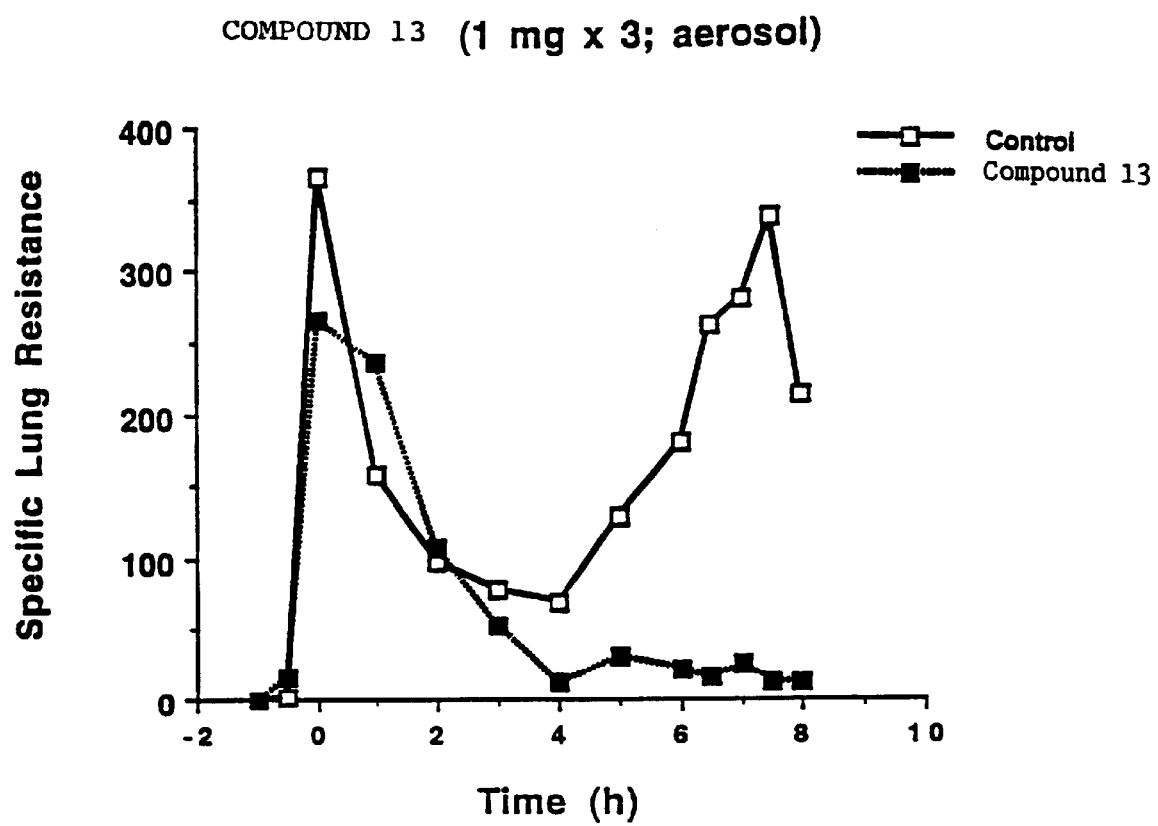
FIG. 1 compares the specific lung resistance of a control (open squares) versus 2-(5-aminomethyl-1H-benzoimidazol-2-ylmethyl)—N—(3-phenylpropyl)-1H-benzoimidazole-5-carboxamide (Compound 4; closed squares) over time as measured in hours.

Unless otherwise stated, the following terms used in the specification and claims are defined for the purposes of this application and have the meanings given below:

"Alkanoyl" means the radical —C(O)R, wherein R is alkyl as defined below, having overall the number of carbon atoms indicated (e.g., $(C_{1-6})$alkanoyl includes the radicals formyl, acetyl, propionyl, butyryl, isobutyryl, crotonoyl, isocrotonyl, etc.).

"Alicyclic moiety" means any saturated or unsaturated, monocyclic or polycyclic hydrocarbon portion of a radical. For example, alicyclic moiety refers to cycloalkyl, as defined herein, as well as to alicyclic portions comprising cycloalkylalkyl, cycloalkyloxy, cycloalkylcarbonyl, cycloalkylalkanoyl, cycloalkylcarbamoyl, and the like.

"Aliphatic moiety" means any straight or branched, saturated or unsaturated hydrocarbon portion of a radical. For example, aliphatic moiety refers to alkyl or heteroalkyl, as defined herein, as well as to aliphatic portions comprising alkyloxy, arylalkyl, heteroarylalkyl, alkylcarbamoyl, alkanoyl, arylalkanoyl, heteroarylalkanoyl, and the like.

"Alkyl", for the purposes of this application, means a straight or branched, saturated or unsaturated aliphatic hydrocarbon radical having the number of carbon atoms indicated, and any ketone, thioketone or iminoketone thereof (e.g., $(C_{1-8})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, 3-oxopentyl, 3-thioxopentyl, 3-iminopentyl, etc.).

"Alkylene" means a saturated or unsaturated hydrocarbon divalent radical having the number of carbon atoms indicated and any ketone, thioketone, iminoketone and substituted derivative thereof (e.g., $(C_{1-10})$alkylene includes methylene (—CH$_2$—), ethylene (—CH$_2$CH$_2$—), methylethylene, vinylene, ethynylene, trimethylene (—CH$_2$CH$_2$CH$_2$—), 2-oxotrimethylene (CH$_2$C(O)CH$_2$—), 2-thiatrimethylene (—CH$_2$C(S)CH$_2$—), 2-iminotrimethylene (—CH$_2$C(NH)CH$_2$—), propenylene (—CH$_2$CH=CH— or —CH=CHCH$_2$—), propanylylidene (=CHCH$_2$CH$_2$—), propendiylene (=CHCH=CH—), 1-aminotetramethylene, pentamethylene, etc.).

"Alkylidene" means the radical =CRR, wherein each R independently is hydrogen or alkyl, as defined above, having overall the number of carbon atoms indicated (e.g., $(C_{1-6})$ alkylidene includes methylidene, ethylidene, propylidene, isopropylidene, etc.).

"Alkyloxy" means the radical —OR, wherein R is alkyl as defined above, having the number of carbon atoms indicated (e.g., $(C_{1-6})$alkyloxy includes the radicals methoxy, ethoxy, propoxy, isopropoxy, butoxy, sec-butoxy, isobutoxy, tert-butoxy, vinyloxy, allyloxy, 1-propenyloxy, isopropenyloxy, 1-butenyloxy, 2-butenyloxy, 3-butenyloxy, 2-methylallyloxy, ethynyloxy, 1-propynyloxy, 2-propynyloxy, etc.).

"Alkylsulfinyl", "alklsulfonyl" and "alkylthio" mean the radicals —SOR, —S(O)$_2$R and —SR, respectively, wherein R is alkyl as defined above, having the number of carbon atoms indicated (e.g., $(C_{1-6})$alkylsulfonyl includes methylsulfonyl, ethylsulfonyl, propylsulfonyl, isopropylsulfonyl, butylsulfonyl, sec-butylsulfonyl, isobutylsulfonyl, tert-butylsulfonyl, vinylsulfonyl, allylsulfonyl, 1-propenylsulfonyl, isopropenylsulfonyl, 1-butenylsulfonyl, 2-butenylsulfonyl, 3-butenylsulfonyl, 2-methylallylsulfonyl, ethynylsulfonyl, 1-propynylsulfonyl, 2-propynylsulfonyl, etc.).

"Ammonio" means the radical —NH$_3^+$.

"Amidino" means the radical —C(NH)NH$_2$.

"Amino" means the radical —NH$_2$.

"Animal" includes humans, non-human mammals (e.g., dogs, cats, rabbits, cattle, horses, sheep, goats, swine, deer, etc.) and non-mammals (e.g., birds, etc.).

"Aryl" means an aromatic monocyclic or fused polycyclic hydrocarbon radical containing the number of carbon atoms indicated, wherein each ring contained therein is comprised of 6 annular members (e.g., $(C_{6-14})$aryl includes phenyl, naphthyl, anthracenyl, phenanthrenyl, etc.).

"Arylsulfonyl" mean the radicals —S(O)$_2$R, wherein R is aryl as defined above, having the number of carbon atoms indicated (e.g., $(C_{6-10})$arylsulfonyl includes phenylsulfonyl, naptht-1-ylsulfonyl, etc.).

"Aromatic moiety" means any aromatic portion of a radical. For example, aromatic moiety refers to aryl and heteroaryl, as defined herein, as well as the aromatic portions comprising arylalkyl, heteroarylalkyl, polycycloaryl, heteropolycycloaryl, and the like.

"Azolidinyl" means a saturated or unsaturated 5-membered monocyclic radical containing the number of nitrogen atoms indicated. For example, $(N_{1-4})$azolidinyl includes pyrazolidinyl, pyrrolidinyl, imidazolidinyl, trizolidinyl, tetrazolidinyl, dihydropyrrolyl, dihydroimidazolyl, dihydropyrazolyl and dihydrotriazolyl.

"Azolyl" means an aromatic 5-membered monocyclic radical containing the number of nitrogen atoms indicated. For example, $(N_{1-4})$azolyl includes pyrrolyl, imidazolyl, pyrazolyl, triazolyl and tetrazolyl.

"Carbamoyl" means the radical —C(O)NH$_2$.

"Carboxy" means the radical —C(O)OH.

"Cyano" means the radical —CN.

"Cycloalkyl" means a saturated or unsaturated, monocyclic or fused polycyclic hydrocarbon radical containing the number of carbon atoms indicated, wherein each ring contained therein is comprised of 3 to 8 annular members, and any carbocyclic ketone, thioketone and iminoketone derivative thereof (e.g., $(C_{3-14})$cycloalkyl includes cyclopropyl, cyclobutyl, cyclopentyl, cyclohexyl, cyclohexenyl, 2,5-cyclohexadienyl, bicyclo[2.2.2]octyl, oxocyclohexyl, dioxocyclohexyl, thiocyclohexyl, etc.).

"Cycloalkylene" means a saturated or unsaturated, monocyclic or fused polycyclic hydrocarbon divalent radical containing the number of carbon atoms indicated, wherein each ring contained therein is comprised of 3 to 8 annular members, and any carbocyclic ketone, thioketone or iminoketone derivative thereof (e.g., $(C_{3-10})$cycloalkylene includes 1,2-cyclopropylene, 1,2-cyclobutylene, 1,3-cyclobutylene, 1,2-cyclopentylene, 1,3-cyclopentylene, 1,4-cyclopentylene, 1,4-cyclohexylene, 3-cyclohexen-1,2-ylene, 2,5-cyclohexadien-1,4-ylene, 1,4-bicyclo[2.2.2]octylene, 5-oxo-1,3-cyclohexylene, 2,5-dioxo-1,4-cyclohexylene, 5-thioxo-1,4-cyclohexylene, etc.).

"Deprotecting" refers to removing any protective groups present after the selective reaction has been carried out.

"Disease" specifically includes any unhealthy condition of an animal or part thereof and includes an unhealthy condition which may be caused by, or incident to, medical or veterinary therapy applied to that animal, i.e., the "side effects" of such therapy.

"Fused heteropolycyclic radical" includes "fused heterobicyclic radical" and means a heterocyclic radical containing two to three fused rings having the number of annular members indicated, wherein at least two annular members of one ring are common to a second ring (e.g., a heteropolycyclic radical containing from 8 to 18 annular atoms and the carbocyclic ketone and thioketone derivatives thereof includes 1H-benzimidazol-2-yl, 1H-naphtho[2,3-d]imidazol-2-yl, 1H-imidazo[4,5-f]quinolin-2-yl, 1H-imidazo[4,5-b]pyridin-2-yl, 1H-phenanthro[9,10-d]imidazol-2-yl, 1H-imidazo[4,5-g]quinoxalin-2-yl, 2,6-dioxo-2,3,6,7-tetrahydro-1H-purin-8-yl, 2,6-dithioxo-2,3,6,9-tetrahydro-1H-purin-8-yl, 7H-purin-8-yl, 5,1,6-dihydrocyclopentaimidazol-2-yl, 4-quinolin-2-yl, etc.).

"Guanidino" means the radical —NHC(NH)NH$_2$.

"Halo" means fluoro, chloro, bromo or iodo.

"Heteroatom" means an atom selected from N, O, S and P.

"Heteroatom moiety", unless indicated otherwise, means a moiety selected from —N=, —NR$^{17}$—, —O—, —S—, —S(O)—, —S(O)$_2$—, —P(O)(OR$^{17}$)—, wherein R$^{17}$ is hydrogen or $(C_{1-6})$alkyl.

"Heteroalkyl" means alkyl, as defined above, except one or more of the carbon atoms indicated is replaced by a heteroatom moiety, as defined in the Detailed Description of the Invention, and any ketone, thioketone or iminoketone derivative thereof (e.g., hetero$(C_{2-12})$alkyl includes methoxy, ethoxy, ethylthio, 2-(2-methoxyethoxy)ethoxy, 3-methoxymethoxycarbonylmethoxy, 2—(N-ethyl-methylamino)ethyl, 2-ethyliminoethyl, ethoxymethoxyphosphoryloxy, etc.).

"Heteroalkylene" means alkylene, as defined above, except one or more of the carbon atoms indicated is replaced by a heteroatom moiety, as defined in the Detailed Description of the Invention, or any suitable combination thereof (e.g., —OS(O)$_2$—,—S(O)$_2$—, —N(R)S(O)$_2$—, —S(O)$_2$NR$^{17}$—, —OP(O)(OR$^{17}$)O—, and the like, wherein R$^{17}$ is hydrogen or $(C_{1-6})$alkyl), and any ketone, thioketone or iminoketone derivative thereof (e.g., hetero$(C_{2-10})$alkylene includes azaethylene (—CH$_2$NH—), 2-azapropenylene (—CH$_2$N=CH$_2$—), 1-oxatrimethylene (—CH$_2$CH$_2$O—), 2-oxo-3-azapentamethylene, 3-aza-2-thiopentamethylene, 2-oxa-3-oxopentamethylene, 3-aza-2-iminopentamethylene (—CH$_2$CH$_2$NHC(NH)CH$_2$—), 2,4-aza-2-methyl-3,3-dioxo-3-thiapentamethylene (—CH$_2$NHS(O)$_2$N(CH$_3$)CH$_2$—), 3-hydroxy-2,4-oxa-3-oxo-3-phosphapentamethylene (—CH$_2$OP(O)(OH)OCH$_2$—), 3-aza-2-oxo-4-carboxyhexamethylene, 4-aza-1-oxa-3-oxohexamethylene, 1-thia-3-oxo-4-azahexamethylene, 1-thia-1,1,3-trioxo-4-azahexamethylene (—CH$_2$CH$_2$NHC(O)CH$_2$S(O)$_2$—), 3-aza-4-oxoheptamethylene, 1,4,7-trioxaoctamethylene, 6-aza-1-oxa-2,5-dioxooctamethylene (—CH$_2$CH$_2$NHC(O)CH$_2$CH$_2$C(O)O—), 3-aza-4-oxodecamethylene, etc.).

"Heteroaryl" means an aromatic monocyclic or fused polycyclic divalent radical having the number of annular atoms indicated, wherein each ring contained therein is comprised of 5 to 6 annular members and one or more of the annular atoms is a heteroatom moiety selected from —N=, —NR$^{17}$—, —O— or —S—, wherein R$^{17}$ is hydrogen or $(C_{1-6})$alkyl, and each ring contained therein is comprised of 5 to 6 annular members (e.g., hetero$(C_{5-14})$aryl includes thienyl, furyl, pyrrolyl, pyrimidinyl, isoxazolyl, oxaxolyl, indolyl, benzo[b]thienyl, isobenzofuranyl, purinyl, isoquinolyl, pterdinyl, perimidinyl, imidazolyl, pyridyl, pyrazolyl, pyrazinyl, quinolyl, etc.).

"Heterocycloalkyl" means cycloalkyl, as defined above, except one or more of the annular carbon atoms indicated are replaced by a heteroatom moiety, as defined in the Detailed Description of the Invention, and any carbocyclic ketone, thioketone or iminoketone derivative thereof (e.g., the term heterocyclo$(C_{5-14})$alkyl includes piperidyl, pyrrolidinyl, pyrrolinyl, imidazolidinyl, quinuclidinyl, morpholinyl, etc.).

"Heterocycloalkylene" means cycloalkylene, as defined above, except one or more of the annular carbon atoms indicated is replaced by a heteroatom moiety, as defined in the Detailed Description of the Invention, and any carbocyclic ketone, thioketone or iminoketone derivative thereof (e.g., the term heterocyclo$(C_{3-14})$alkylene includes piperidylene, pyrrolidinylene, pyrrolinylene, imidazolidinylene, quinuclidinylene, morpholinylene, etc.).

"Heteropolycycloaryl" means polycycloaryl, as defined below, except one or more of the annular carbon atoms indicated are replaced by a heteroatom moiety, as set defined in the Detailed Description of the Invention, and any carbocyclic ketone, thioketone of iminoketone derivative thereof (e.g., heteropolycyclo$(C_{8-10})$alkyl includes 3,4-dihydro-2H-quinolinyl, 5,6,7,8-tetrahydroquinolinyl, 3,4-dihydro-2H-[1,8]naphthyridinyl, 2,4-dioxo-3,4-dihydro-2H-quinazolinyl, 3-oxo-2,3-dihydrobenzo[1,4]oxazinyl, etc.).

"Hydroxy" means the radical —OH.

"Immunomediated inflammatory disorder" means those diseases associated with mast cell mediator release and susceptible to treatment with a tryptase inhibitor (e.g., immediated type hypersensitivity diseases such as asthma, allergic rhinitis, urticaria and angioedema, eczematous anaphylaxis, dermatitis such as atopic dermatitis, hyperproliferative skin disease, peptic ulcers, inflammatory bowel disorder, ocular and vernal conjunctivitis, rheumatoid arthritis, inflammatory skin conditions, and the like).

"Hyper-responsiveness" means the late phase bronchoconstriction and airway hyperreactivity associated with chronic asthma. Hyper-responsiveness of asthmatic bronchiolar tissue is believed to result from chronic inflammation reactions, which irritate and damage the epithelium lining the airway wall and promote pathological thickening of the underlying tissue.

"Syncytial viral infection" means an infection by a virus, such as a respiratory syncytial virus, causing the formation of a cellular protoplasmic mass, i.e. syncytia, via infection.

"Imino" means the radical =NH.

"Isomers" mean compounds of Formula I having identical molecular formulae but differ in the nature or sequence of bonding of their atoms or in the arrangement of their atoms in space. Isomers that differ in the arrangement of their atoms in space are termed "steroisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diasteromer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. The substituents attached to the chiral center under consideration are ranked in accordance with the Sequence Rule of Cahn, Ingold and Prelog and the absolute descriptor R or S is cited in parenthesis followed by a hyphen and the chemical name of the compound. Compounds of Formula I that contain a chiral center can exist as individual stereoisomers or mixtures of steroisomers. For the purposes of the present application when referring to a compound of Formula I by name or by formula and the configuration is not designated, it is to be understood that the referenece is to all possible configurations of the compound.

"Optional" or "optionally" means that the subsequently described event or circumstance may or may not occur, and that the description includes instances where the event or circumstance occurs and instances in which it does not. For example, the phrase "optionally is substituted with one to three radicals" means that the group referred to may or may not be substituted in order to fall within the scope of the invention.

"N-oxide derivatives" means a derivatives of compound of Formula I in which nitrogens are in an oxidized state (i.e., O←N) and which possess the desired pharmacological activity. The N-oxide derivatives of compounds of Formula I can be prepared by methods known to those of ordinary skill in the art.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirabale and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptabale inorganic bases include sodium hydroxide, sodium carbonate, potassium hydroxide, aluminum hydroxide and calcium hydoxide. Acceptable organic bases include ethanolamine, diethanolamine, triethanolamine, tromethamine, N-methylglucamine and the like.

"Polycycloaryl" means a fused polycyclic radical containing the number of carbon atoms indicated, wherein at least one, but not all, of the fused rings comprising the radical is aromatic and each ring contained therein is comprised of five to six annular members, and any carbocyclic ketone and thioketone derivative thereof (e.g., polycyclo $(C_{9-10})$aryl includes indanyl, indenyl, 1,2,3,4-tetrahydronaphthyl, 1,2-dihydronaphthyl, 2,4-dioxo-1,2,3,4-tetrahydronaphthyl, etc.).

"Prodrug derivatives" means derivatives of compounds of Formula I which are converted in vivo to the corresponding non-derivatized form of a compound of Formula I. Suitable prodrug derivatives include those compounds of Formula I in which one or more nitrogen and/or oxygen atoms with an available free valence are substituted with a group which is readily cleavable by in vivo processes. For example, prodrug derivatives of compounds of Formula I may contain one or more N-substituted amino groups (e.g., —NH$_2$(R$^{18}$)) N-substituted nitrogen atoms incorporated into an aliphatic, alicyclic or aromatic structure (e.g., —N(R$^{18}$)—), N-substituted imino or amidino groups (e.g., —C(NR$^{18}$)H, —C(NR$^{18}$)NH$_2$ or —C(NH)NHR$^{18}$), N-substituted guanidino groups (e.g., —NHC(NR$^{18}$)NHR$^{18}$, —NHC(NH) NHR$^{18}$ or —NHC(NR$^{18}$)NH$_2$), and the like, in which R$^{18}$ is (i) —C(O)R$^{19}$ or —CH(R$^{20}$)OC(O)R$^{19}$, wherein R$^{19}$ is $(C_{1-10})$alkyl, $(C_{1-10})$alkyloxy, carbamoyl, $(C_{1-10})$alkylcarbamoyl, di$(C_{1-10})$alkylcarbamoyl, cis-2-$(C_{1-10})$ alkanoyloxyphenylvinyl, 3-$(C_{1-10})$alkanoyloxybutyryl, $(C_{3-10})$cycloalkyl, hetero$(C_{3-10})$cycloalkyl, $(C_{6-10})$aryl or hetero$(C_{5-10})$aryl and R$^{20}$ is hydrogen or $(C_{1-10})$alkyl; (ii) —X$^7$—R$^{21}$, wherein X$^7$ is $(C_{1-10})$alkylene and R$^{21}$ is carboxy; or (iii) —C(O)OCH(R$^{22}$)OC(O)R$^{23}$, wherein R$^{22}$ is hydrogen, $(C_{1-10})$alkyl or $(C_{3-10})$cycloalkyl and R$^{23}$ is $(C_{1-10})$alkyl or $(C_{3-10})$cycloalkyl. In addition, prodrug derivatives of compounds of Formula I may contain one or more N-hydroxylated imino or amidino groups (e.g., —C(NOR$^{24}$)H, —C(NOR$^{24}$)NH$_2$ or —C(NH)NHOR$^{24}$) or N-hydroxylated guanidino groups (e.g., —NHC(NOR$^{24}$) NH$_2$, —NHC(NH)NHOR$^{24}$), in which R$^{24}$ is hydrogen, methyl, —C(O)R$^{25}$ or —CH(R$^{26}$)OC(O)R$^{25}$, wherein R$^{25}$ is $(C_{1-10})$alkyl or $(C_{3-10})$cycloalkyl and R$^{26}$ is hydrogen or $(C_{1-10})$alkyl; N-substituted hydroxy groups (e.g., —OR$^{27}$), in which R$^{27}$ is —C(O)R$^{19}$ or —CH(R$^{20}$)OC(O)R$^{19}$, wherein R$^{19}$ and R$^{20}$ are as defined above; and/or ester derivatives of carboxylic acids (e.g., —C(O)OR$^{28}$) wherein R$^{28}$ is $(C_{1-10})$alkyl or $(C_{3-10})$cycloalkyl.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed. "Protected derivatives" means derivatives of compounds of Formula I in which a reactive site or sites are blocked with protective groups. Protected derivatives of compounds of Formula I are useful in the preparation of compounds of Formula I. Suitable protecting groups for reactive nitrogen atoms include tert-butoxycarbonyl, benzyloxycarbonyl and any other suitable amino protective groups (e.g., see T. W. Greene, *Protective Groups in Organic Synthesis*, John Wiley & Sons, Inc. 1981). In particular, a suitable protected derivative of Formula I is exemplified by the compound 2-[5-(1,3-dioxo-1,3-dihydroisoindol-2-ylmethyl)-1H-benzoimidazol-2-ylmethyl]-4,5,6,7-tetrahydro-1H-benzoimidazole-5-carboxylic acid.

"Therapeutically effective amount" means that amount which, when administered to an animal is effective for treating a disease.

"Treatment" or "treating" refers to any administration of a compound of the present invention and includes:

(1) preventing the disease from occurring in an animal which may be predisposed to the disease but does not yet experience or display the pathology or symptoms of the disease, (2) inhibiting the disease, i.e., arresting development of its pathology and/or symptoms, or (3) ameliorate the disease, i.e., reversing its pathology and/or symptoms.

"Sulfo" means the radical —S(O)OH.

"Uriedo" means the radical —NHC(O)NH$_2$.

The compounds of Formula I and the intermediates and starting materials used in their preparation are named in accordance with IUPAC rules of nomenclature. For example, a compound of Formula I in which:

A together with B comprises 5-guanidino-1H-benzoimidazol-2-yl, C comprises 5-(2-naphth-1-ylethylcarbamoyl)-1H-benzoimidazol-2-yl and X$^3$ is —CH$_2$— is named 2-(5-guanidino-1H-benzoimidazol-2-ylmethyl)—N-(2-naphth-1-ylethyl-1H-benzoimidazole-5-carboxamide;

A together with B comprises 5-guanidino-1H-benzoimidazol-2-yl, C comprises 6-(2-naphth-1-ylethylcarbamoyl)-1-methyl-1H-benzoimidazol-2-yl and X$^3$ is —CH$_2$— is named 2-(5-guanidino-1H-benzoimidazol-2-ylmethyl)-3-methyl—N-(2-naphth-1-ylethyl-3H-benzoimidazole-5-carboxamide;

A together with B comprises 5-guanidino-1H-benzoimidazol-2-yl, C comprises 6-[2-(2-carboxyphenyl)ethylcarbamoyl]-1-(3-sulfopropyl-1H-benzoimidazol-2-yl and X$^3$ is —CH$_2$— is named 2-{2-[2-(5-guanidino-1H-benzoimidazol-2-ylmethyl)-3-(3-sulfopropyl)-3H-benzoimidazol-5-ylcarbonylamino]ethyl}benzoic acid; and A together with B comprises 5-guanidino-1H-benzoimidazol-2-yl, C comprises 6-[2-(2-methoxyphenyl)ethylcarbamoyl]-1-(3-sulfopropyl-1H-benzoimidazol-2-yl and X$^3$ is —CH$_2$— is named 3-{2-(5-guanidino-1H-benzoimidazol-2-ylmethyl)-6-[2-(2-methoxyphenyl)ethylcarbamoyl]benzoimidazol-1-yl}propane-1-sulfonic acid.

Certain compounds of Formula I exist in tautomeric equilibrium. For example, compounds of Formula I in which C comprises 4,5,6,7-tetrahydro-3H-imidazo[4,5-c]pyridin-2-yl exist in equilibrium between tautomers of the following formulae:

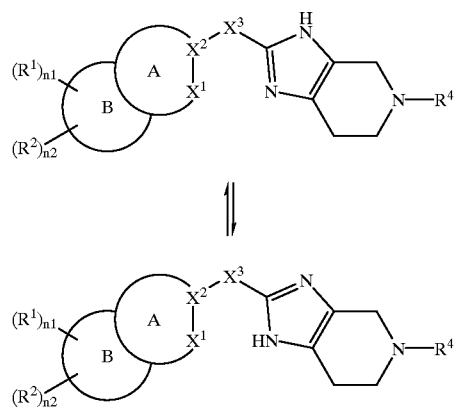

and, hence, while the compounds of this invention may be named, illustrated or otherwise described in this application as one possible tautomer, it is to be understood that all possible tautomers are meant to be encompassed by such names, illustrations and descriptions. Thus, the name ethyl 2-(4-{2-[1-(5-guanidino-1H-benzoimidazol-2-yl)ethyl]-1,4,6,7-tetrahydro-imidazo[4,5-c]pyridin-5-yl}-4-oxobutyl)benzoate is meant to include its tautomers ethyl 2-(4-{2-[1-(5-guanidino-3H-benzoimidazol-2-yl)ethyl]-1,4,6,7-tetrahydro-imidazo[4,5-c]pyridin-5-yl}-4-oxobutyl)benzoate, ethyl 2-(4-{2-[1-(5-guanidino-1H-benzoimidazol-2-yl)ethyl]-3,4,6,7-tetrahydroimidazo[4,5-c]pyridin-5-yl}-4-oxobutyl)benzoate and ethyl 2-(4-{2-[1-(5-guanidino-3H-benzoimidazol-2-yl)ethyl]-3,4,6,7-tetrahydroimidazo[4,5-c]pyridin-5-yl}-4-oxobutyl)benzoate.

Presently Preferred Embodiments

While the broadest definition of this Invention is set forth in the Summary of the Invention, certain aspects of the Invention are preferred. A preferred aspect of the Invention is a compound of Formula I in which A together with B comprises a fused heterobicyclic radical wherein A contains 5 annular members and B contains 6 annular members and X$^4$ and X$^5$ are adjacent members of an oxazol-2-yl, 1H-imidazol-2-yl or thiazol-2-yl ring.

A preferred aspect of the Invention are compounds of Formula II:

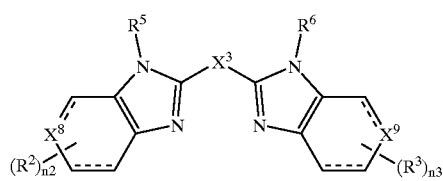

II in which:

the dashed lines independently represent optional bonds;
each R$^2$ independently is (C$_{1-6}$)alkyl, (C$_{1-6}$)alkyloxy, halo or hydroxy;
each R$^3$ independently is (C$_{1-6}$)alkyl, (C$_{1-6}$)alkyloxy, halo or hydroxy;
X$^3$ is C(O)— or R$^7$R$^8$—,
X$^8$ is —CH(R$^1$)$_{n1}$— or —C(R$^1$)$_{n1}$=, wherein R$^1$ is amino(N$_{1-4}$)azolidinyl, amino(N$_{1-4}$)azolyl, (N$_{1-4}$)azolidinyl, (N$_{1-4}$)azolyl, —NHC(NH)NR$^9$R$^9$, —C(NR$^9$)R$^9$, —C(NH)NHR$^{10}$, —C(NH)NR$^{10}$ R$^{10}$ or —(CR$^{11}$R$^{11}$)$_y$NH$_2$, or X$^8$ is —N= or —NH(R$^1$)$_{n1}$—, wherein R$^1$ is —C(NR$^9$)R$^9$, —C(NH)NHR$^{10}$ or —C(NH)NR$^{10}$R$^{10}$, wherein each R$^9$ independently is hydrogen or (C$_{1-6}$)alkyl and each R$^{10}$ independently is (C$_{1-6}$)alkyl; and X$^9$ is —CH(R$^4$)— or —C(R$^4$)=, wherein R$^4$ is —R$^{12}$, —OR$^{12}$, —N(R$^{13}$)R$^{12}$, —SR$^{12}$, —S(O)R$^{12}$, —S(O)$_2$R$^{12}$, —S(O)$_2$O R$^{12}$, —S(O)$_2$N(R$^{13}$)R$^{12}$, —N(R$^{13}$)S(O)$_2$ R$^{12}$, —C(O)R$^{12}$, —C(O)R$^{12}$, —C(O)N(R$^{13}$)R$^{12}$, —N(R$^{13}$)C(O)R$^{12}$, —C(O)N(R$^{13}$)R$^{12}$, —N(R$^{13}$)C(O)OR$^{12}$, —CH$_2$)$_{n4}$N(R$^{13}$)C(O)N(R$^{13}$)R$_{12}$, —OP(O)(OR$^{13}$)O R$^{12}$ or —C(O)N(R$^{14}$)CH(COOH)R$^{12}$, or X$^9$ is —N= or —N(R$^4$)—, wherein R$^4$ is —C(O)R$^{12}$, —C(O)OR$^{12}$, —C(O)N(R$^{13}$)R$^{12}$, —OC(O)N(R$^{13}$)R$^{12}$ or —C(O)N(R$^{14}$)CH(COOH)R$^{12}$, wherein R$^{12}$, R$^{13}$ and R$^{14}$ are as defined in the Summary of the Invention.

A preferred aspect of the invention are compounds of Formula I in which:

R$^5$ is hydrogen or (C$_{1-4}$)alkyl, R$^6$ is hydrogen or (C$_{1-4}$) alkyl, which alkyl optionally is substituted with one to two substituents independently selected from (C$_{1-4}$) alkyloxy, hydroxy and sulfo, R$^7$ is hydrogen or methyl and R$^8$ is hydrogen, methyl or hydroxy;

X$^8$ is —CH(R$^4$)— or —C(R$^1$)$_{n1}$=, wherein R$^1$ is aminomethyl, 1-aminocyclopropyl, 2-aminoimidazol-1-yl, 2-amino-1,1-dimethylethyl, imidazolyl, tetrazolyl, —(CH$_2$)$_x$NHC(NR$^9$)R$^9$, —(CH$_2$)$_x$NHC(NH)NR$^9$R$^9$ and —C(NR$^9$)R$^9$, wherein each R$^9$ independently is hydrogen or methyl, or X$^8$ is —N(R$^1$)$_{n1}$—, wherein R$^1$ is —C(NR$^9$)R$^9$, —C(NH)NHR$^{10}$ or —C(NH)NR$^{10}$R$^{10}$, wherein each R$^9$ independently is hydrogen or methyl and each R$^{10}$ is methyl, wherein any aliphatic or alicyclic moiety comprising R$^1$ optionally is substituted with one to two substituents independently selected from methylsulfonyl and carboxy;

X$^9$ is —C(R$^4$)=, wherein R$^4$ is —R$^{12}$, —OR$^{12}$, —C(O)R$^{12}$, —C(O)OR$^{12}$, —C(O)N(R$^{13}$)R$^{12}$ or —C(O)N(R$^{14}$)CH(COOH)R$^{12}$, wherein R$^{13}$ and R$^{14}$ independently are hydrogen or (C$_{1-6}$)alkyl; R$^{12}$ is —R$^{15}$ or —X$^6$—(R$^{15}$)$_{n15}$, wherein X$^6$ is (C$_{1-10}$)alkylene or hetero(C$_{2-10}$)alkylene and each R$^{15}$ independently is hydrogen, (C$_{6-14}$)aryl, cyclo(C$_{3-14}$)alkyl, polycyclo(C$_{6-14}$)aryl, heteropolycyclo(C$_{6-14}$)aryl, heterocyclo(C$_{3-14}$)alkyl or hetero(C$_{5-14}$)aryl;

any aliphatic and alicyclic moiety comprising R$^4$ optionally is substituted with one to five substituents independently selected from (C$_{1-4}$)alkyloxy, (C$_{1-4}$) alkyloxycarbonyl, amino, carbamoyl, carboxy and hydroxy; and any aromatic moiety comprising R$^{15}$ optionally is substituted with one to three substituents independently selected from (C$_{1-4}$)alkyl, (C$_{1-4}$)alkyloxy, (C$_{1-4}$) alkyloxycarbonyl, carbamoyl, carboxy, cyano, cyclo(C$_{3-6}$)alkyloxy, halo, hetero(C$_{1-8}$)alkyl, hetero(C$_{1-8}$)alkylcarbonyl, hetero(C$_{5-6}$)aryl and trifluoromethyl; and the N-oxide derivatives, prodrug derivatives, protected derivatives, individual isomers, mixtures of isomers and pharmaceutically acceptable salts thereof.

A preferred aspect of the invention are compounds of Formula I in which:

A together with B comprises 4,5,6,7-tetrahydro-1H-imidazo[4,5-c]pyridin-2-yl, wherein n2 is 0 and R$^1$ is —C(NR$^9$)R$^9$, or A together with B comprises 1H-benzoimidazol-2-yl or 4,5,6,7-tetrahydro-1H-benzoimidazol-2-yl, wherein R$^1$ is aminomethyl or guanidino and each R$^2$ independently is halo or hydroxy;

C comprises 4,5,6,7-tetrahydro-1H-imidazo[4,5-c]pyridin-2-yl or 1H-benzoimidazol-2-yl, wherein R$^4$ is —C(O)X$^6$—R$^{15}$, —C(O)OX$^6$—R$^{15}$ or —C(O)NHX$^6$—R$^{15}$, wherein X$^6$ is (C$_{1-4}$)alkylene or hetero(C$_{2-4}$)alkylene and R$^{15}$ is (C$_{6-10}$)aryl, (C$_{6-10}$)aryloxy, polycyclo(C$_{6-10}$)aryl, hetero(C$_{5-10}$)aryl, hetero(C$_{5-10}$)aryloxy or heteropolycyclo(C$_{6-14}$)aryl; and any aromatic moiety comprising R$^{15}$ optionally is substituted with one to three substituents independently selected from (C$_{1-4}$)alkyl, (C$_{1-4}$)alkyloxy, (C$_{1-4}$) alkyloxycarbonyl, carboxy, carbamoyl, halo, hydroxy and tetrazol-1-yl; and the N-oxide derivatives, prodrug derivatives, protected derivatives, individual isomers, mixtures of isomers and pharmaceutically acceptable salts thereof.

A preferred aspect of the invention are compounds of Formula I in which n1 is 0 and each R$^2$ independently is halo or hydroxy, in particular:

2-(2-{2-[1-(4,6,7-trifluoro-1H-benzoimidazol-2-yl) ethyl]-3-methyl-3H-benzoimidazol-5-ylcarbonylamino}ethoxy)benzoic acid;

2-(2-{2-[1-(5,6-difluoro-1H-benzoimidazol-2-yl)ethyl]-3-methyl-3H-benzoimidazol-5-ylcarbonylamino}ethoxy)benzoic acid;

butyl 2-(2-{2-[1-(5-hydroxy-1H-benzoimidazol-2-yl) ethyl]-3-methyl-3H-benzoimidazol-5-ylcarbonylamino}ethoxy)benzoate;

propyl 2-(2-{2-[1-(5-hydroxy-1H-benzoimidazol-2-yl) ethyl]-3-methyl-3H-benzoimidazol-5-ylcarbonylamino}ethoxy)benzoate; and isobutyl 2-(2-{2-[1-(5-hydroxy-1H-benzoimidazol-2-yl) ethyl]-3-methyl-3H-benzoimidazol-5-ylcarbonylamino}ethoxy)benzoate.

A preferred aspect of the invention are compounds of Formula I in which R$^1$ is guanidino of aminomethyl, in particular:

2-(5-guanidino-1H-benzoimidazol-2-ylmethyl)-3-methyl—N-(2-naphth-1-ylethyl)-3H-benzoimidazole-5-carboxamide;

ethyl 2-(4-{2-[1-(5-guanidino-1H-benzoimidazol-2-yl) ethyl]-1,4,6,7-tetrahydroimidazo[4,5-c]pyridin-5-yl}-4-oxobutyl)benzoate;

2-(5-guanidino-1H-benzoimidazol-2-ylmethyl)-3-(2,3-dihydroxy)propyl-N-(2-naphth-1-ylethyl)-3H-benzoimidazole-5-carboxamide;

2-(5-guanidino-1H-benzoimidazol-2-ylcarbonyl)-3-(2,3-dihydroxy)propyl-N-(2-naphth-1-ylethyl)-3H-benzoimidazole-5-carboxamide;

2-(5-guanidino-1H-benzoimidazol-2-ylmethyl)-3-(3-hydroxy)propyl-N-(2-naphth-1-ylethyl)-3H-benzoimidazole-5-carboxamide;

2-(5-guanidino-1H-benzoimidazol-2-ylmethyl)-3-(2-hydroxy)ethyl-N-(2-naphth-1-ylethyl)-3H-benzoimidazole-5-carboxamide;

2-[1-(5-guanidino-1H-benzoimidazol-2-yl)ethyl]—N-[2-(2-carbamoylphenoxy)ethyl]-3-methyl-3H-benzoimidazole-5-carboxamide;

2-[1-(5-guanidino-1H-benzoimidazol-2-yl)ethyl]—N-[2-(2-carbamoyl-4-chlorophenoxy)ethyl]-3-methyl-3H-benzoimidazole-5-carboxamide;

4-chloro-2-[2-({2-[1-(5-guanidino-1H-benzoimidazol-2-yl)ethyl]-3-methyl-3H-benzoimidazol-5-ylcarbonyl}amino)ethoxy]benzoic acid;

5-chloro-2-[2-({2-[1-(5-guanidino-1H-benzoimidazol-2-yl)ethyl]-3-methyl-3H-benzoimidazol-5-ylcarbonyl}amino)ethoxy]benzoic acid;

2-(5-aminomethyl-1H-benzoimidazol-2-ylmethyl)-3-methyl—N-(2-naphth-1-ylethyl)-3H-benzoimidazole-5-carboxamide; and 2-(5-aminomethyl-4,5,6,7-tetrahydro-1H-benzoimidazol-2-ylmethyl)-3-methyl-N-(2-naphth-1-ylethyl)-3H-benzoimidazole-5-carboxamide.

A preferred aspect of this invention are compounds of Formula I in which C comprises 4,5,6,7-tetrahydro-1H-imidazo[4,5-c]pyridin-2-yl and $R^1$ is $C(NH)R^9$, in particular:

2-[2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)ethoxy]benzoic acid;

2-[5-(1-iminoethyl)-4,5,6,7-tetrahydro-1H-imidazo[4,5-c]pyridin-2-ylmethyl]-3-methyl-N-(2-naphth-1-ylethyl)-3H-benzoimidazole-5-carboxamide;

2-[5-(1-iminoethyl)-4,5,6,7-tetrahydro-1H-imidazo[4,5-c]pyridin-2-ylcarbonyl]-3-methyl-N-(2-naphth-1-ylethyl)-3H-benzoimidazole-5-carboxamide;

2-(5-iminomethyl-4,5,6,7-tetrahydro-1H-imidazo[4,5-c]pyridin-2-ylmethyl)-3-methyl-N-(2-naphth-1-ylethyl)-3H-benzoimidazole-5-carboxamide;

2-[5-(1-iminoethyl)-4,5,6,7-tetrahydro-1H-imidazo[4,5-c]pyridin-2-ylmethyl]-3-methyl-N-(2-hydroxy-2-naphth-1-ylethyl)-3H-benzoimidazole-5-carboxamide;

2-[5-(1-iminoethyl)-4,5,6,7-tetrahydro-1H-imidazo[4,5-c]pyridin-2-ylmethyl]-3-methyl-N-[2-(2-hydroxynaphth-1-yl)ethyl]-3H-benzoimidazole-5-carboxamide;

2-[5-(1-iminoethyl)-4,5,6,7-tetrahydro-1H-imidazo[4,5-c]pyridin-2-ylmethyl]-3-methyl-N-[2-(4-hydroxynaphthal-1-yl)ethyl]-3H-benzoimidazole-5-carboxamide;

2-{1-[5-(1-iminoethyl)-4,5,6,7-tetrahydro-1H-imidazo[4,5-c]pyridin-2-yl]ethyl}-3-methyl-N-(2-naphth-1-ylethyl)-3H-benzoimidazole-5-carboxamide;

ethyl 2-[2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)ethoxy]benzoate;

2-[2-(2-{1-[5-(1-iminoethyl)-4,5,6,7-tetrahydro-1H-imidazo[4,5-c]pyridin-2-yl]ethyl}-3-(2-methoxyethyl)-3H-benzoimidazol-5-ylcarbonylamino)ethoxy]benzoic acid;

ethyl 2-[2-(2-{1-[5-(1-iminoethyl)-4,5,6,7-tetrahydro-1H-imidazo[4,5-c]pyridin-2-yl]ethyl}-1,4,6,7-tetrahydroimidazo[4,5-c]pyridin-5-ylcarbonylamino)ethoxy]benzoate; and 2-{1-[5-(1-iminoethyl)-4,5,6,7-tetrahydro-1H-imidazo[4,5-c]pyridin-2-yl]ethyl}-3-methyl-N-[2-(2-tetrazolylphenoxy)ethyl]-3H-benzoimidazole-5-carboxamide.

Pharmacology and Utility

The compounds of this invention are serine protease inhibitors and, as such, are useful in treating diseases associated with increased serine protease activity. In particular, the compounds of this invention are tryptase inhibitors and are useful in treating diseases associated with increased tryptase activity. In vitro protocols for screening potential inhibitors as to their ability to inhibit tryptase are known in the art. See, e.g., Sturzebecher et al. (1992) *Biol. Chem. Hoppe-Seyler* 373:1025–1030. Typically, these assays measure the enzyme-induced hydrolysis of peptide-based chromogenic substances. Details of an exemplary procedure for measuring tryptase inhibitory activity are described below.

In addition, the activity of the compounds of the present invention can be evaluated in vivo in one of numerous animal models of asthma. See, Larson, "Experimental Models of Reversible Airway Obstruction", in THE LUNG: SCIENTIFIC FOUNDATIONS, Crystal, West et al., eds., Raven Press, New York, 1991; Warner et al. (1990) *Am. Rev. Respir. Dis.* 141:253–257. An ideal animal model would duplicate the chief clinical and physiological features of human asthma, including: airway hyper-responsiveness to chemical mediators and physical stimuli; reversal of airway obstruction by drugs useful in human asthma (β-adrenergics, methylxanthines, corticosteroids, and the like); airway inflammation with infiltration of activated leukocytes; and chronic inflammatory degenerative changes, such as basement membrane thickening, smooth muscle hypertrophy, and epithelial damage. Species used as animal models include mice, rats, guinea pigs, rabbits, dogs, and sheep. All have some limitations, and the proper choice of animal model depends upon the question which is to be addressed.

The initial asthmatic response can be evaluated in guinea pigs, and dogs, and particularly, with a basenji-greyhound cross strain which develops nonspecific airway hyper-responsiveness to numerous nonallergenic substances, such as methacholine and citric acid. Certain selected sheep exhibit a dual response after antigen challenge with Ascaris proteins. In dual responding animals, the initial asthmatic response (LAR) is followed by a late asthmatic response (LAR) at 6–8 hours post-exposure. Hypersensitivity to the cholinergic agonist carbachol increases at 24 hours after antigen challenge in those animals which exhibit LAR.

The allergic sheep model (see below) was used to evaluate the potential antiasthmatic effects of the compounds of the present invention. Administration of compositions comprising the compounds of the present invention to allergic sheep in both oral and inhalant or aerosol formulations, prior to or following exposure to specific allergens demonstrates that such compositions substantially lessen or abolish the late asthmatic response and consequent hyper-responsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, conjunctivitis, rheumatoid spondylitis, osteoarthritis, gouty arthritis and other arthritic conditions, inflammatory bowel disease, peptic ulcers and various skin conditions. Further, the compounds of the present invention can be used to treat syncytial viral infections.

The efficacy of the compounds of the present invention for the treatment of the vast majority of immunomediated inflammatory disorders can be evaluated by either in vitro or in vivo procedures. Thus, the anti-inflammatory efficacy of the compounds of the present invention can be demonstrated by assays well known in the art, for example, the Reversed Passive Arthus Reaction (RPAR)-PAW technique (see, e.g., Gangly et al. (1992) U.S. Pat. No. 5,126,352). Assays for determining the therapeutic value of compounds in the treatment of various skin conditions, such as hyperproliferative skin disease, are well known in the art, for example, the Arachidonic Acid Mouse Ear Test (Id.). The compounds of the present invention can be evaluated for their antiulcer activity according to the procedures described in Chiu et al. (1984) *Archives Internationales de Pharmacodynamie et de Therapie* 270:128–140.

The efficacy of the compounds of the present invention in blocking cell fusion caused by a syncytial virus infection can be evaluated by the methods generally set forth in Tidwell, et al., *J. Med. Chem.* 26:294–298 (1983).

Compositions and Admininstration

According to this invention, a therapeutically or pharmaceutically effective amount of a compound of the invention is administered to a patient suffering from an immunomediated inflammatory disorder. According to one embodiment, the compositions of the present invention are useful for preventing or ameliorating asthma. In using the compositions of the present invention in a treatment of asthma, the compounds may be administered prophylactically prior to exposure to allergen or other precipitating factor, or after such exposure. The compounds of the present invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like. In still a further embodiment, the compounds of the present invention are used to treat syncytial viral infections, particularly infections of respiratory syncytial virus.

The compositions containing the compounds can be administered for therapeutic and/or prophylactic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity and course of the disease, previous therapy, the patient's health status and response to the drugs, and the judgment of the treating physician.

In prophylactic applications, compositions containing the compounds of the invention are administered to a patient susceptible to or otherwise at risk of a particular disease in an amount sufficient to prevent or ameliorate the onset of symptoms. Such an amount is defined to be a "prophylactically effective amount or dose." These can be administered orally or by inhalation. In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form.

The composition used in these therapies can be in a variety of forms. These include, for example, solid, semi-solid and liquid dosage forms, such as tablets, enteric-coated tablets, pills, powders, liquid solutions or suspensions, liposomes, injectable and infusible solutions. Inhalable preparations, such as aerosols, are also included. Preferred formulations are those directed to oral, intranasal, topical and parenteral applications, but it will be appreciated that the preferred form will depend on the particular therapeutic application at hand. Especially preferred formulations are oral or aerosol. The methods for the formulation and preparation of therapeutic compositions comprising the compounds of the invention are well known in the art and are described in, for example, REMINGTON'S PHARMACEUTICAL SCIENCES and THE MERCK INDEX 11th Ed., (Merck & Co. 1989).

While it is possible to administer the active ingredient of this invention alone, it is preferable to present it as part of a pharmaceutical formulation. The formulations of the present i5 invention comprise at least one compound described herein in a therapeutically or pharmaceutically effective dose together with a pharmacologically acceptable carrier. The pharmaceutical compositions will thus contain the compounds of the present invention in concentrations sufficient to deliver an appropriate dose. For example, where the appropriate dose is 0.05 mg per day, the concentration of the compound of the invention in the pharmaceutical composition would be 0.05 mg per dose, where one dose per day is used. For inhalant or aerosol compositions, the concentration of the compounds of the present invention in the composition will generally depend upon the amount of the dose. Typical concentrations of the compounds of the present invention in inhalant or aerosol compositions would be from about 0.01 to about 30 mg/mL. The formulation may include other clinically useful compounds, such as β-adrenergics (e.g., albuterol, terbutaline, formoterol, fenoterol, and prenaline) and corticosteroids (e.g., beclomethasome, triamcinolone, flunisolide, and dexamethasone).

Chemistry

Generally, the compounds of the present invention are synthesized using standard techniques and reagents known to and used by those of skill in the art. It will be noted that the linkages between the various functional groups generally comprise carbon linked to the nitrogen of an amide or carbamate, the oxygen of a carbamate or the carbon of a carbonyl. Those of skill in the art will recognize that methods and reagents for forming these bonds are well known and readily available. See, e.g., March, ADVANCED ORGANIC CHEMISTRY, 4th Ed. (Wiley 1992), Larock, COMPREHENSIVE ORGANIC TRANSFORMATIONS (VCH 1989); and Furniss, et al., VOGEL'S TEXTBOOK OF PRACTICAL ORGANIC CHEMISTRY 5th ed. (Longman 1989), each of which is incorporated herein by reference.

Compounds of Formula I in which $X^4$ and $X^5$ are adjacent members of an oxazol-2-yl, 1H-imidazol-2-yl or thiazol-2-yl ring can be prepared by the methods depicted in the following reaction scheme:

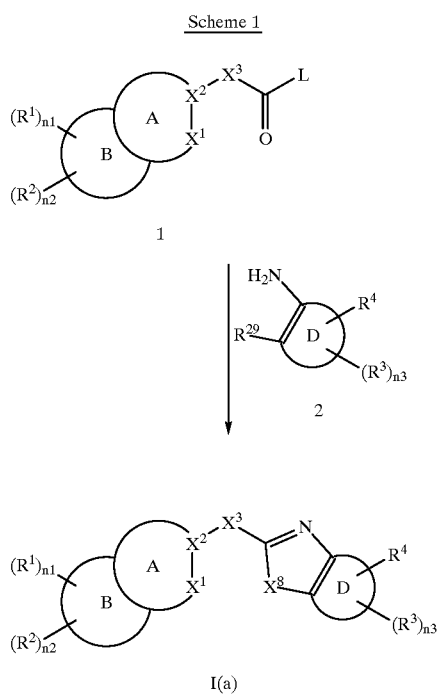

Scheme 1

I(a)

in which L is a leaving group, D together with the vinylene moiety to which it is fused comprises a monocyclic or fused bicyclic divalent radical containing from 5 to 15 annular atoms, wherein each ring contains 5 to 7 annular atoms and each annular atom optionally is a heteroatom, $R^{29}$ is —OH, —$NHR^6$ or —SH, $X^8$ is —O—, —$NR^6$— or —S— and n2, n3, n4, A, B, $X^1$, $X^2$, $X^3$, $X^5$, $R^1$, $R^2$, $R^3$, $R^4$ and $R^6$ are as defined in the Summary of the Invention.

Compounds of Formula I in which $X^4$ and $X^5$ are adjacent members of an oxazol-2-yl, 1H-imidazol-2-yl or thiazol-2-yl ring (Formula 1(a)) can be prepared by reacting a compound of Formula 1, or a protected derivative thereof, with a compound of Formula 2, or a protected derivative thereof, and then deprotecting if necessary. The reaction between the compounds of Formulae 1 and 2 may be carried out neat, but preferably is carried out in the presence of 1,3-dimethyl-3,4,5,6-tetrahydro-2(1H)-pyrimidinone (DMPU) or polyphosphoric acid, at 160 to 200° C., preferably 180–190° C., and requires 1 to 5 hours to complete (e.g., see Examples 4(d), 6(h), 8(k), 9(d) and 10(d), infra.). Deprotection can be effected by any means which removes the protective group and gives the desired product in reasonable yield (e.g., see Example 2(g), infra.).

In a similar fashion, compounds of Formula I in which $X^1$ and $X^2$ adjacent members of an oxazol-2-yl, 1H-imidazol-2-yl or thiazol-2-yl ring can be prepared by the methods depicted in the following reaction scheme:

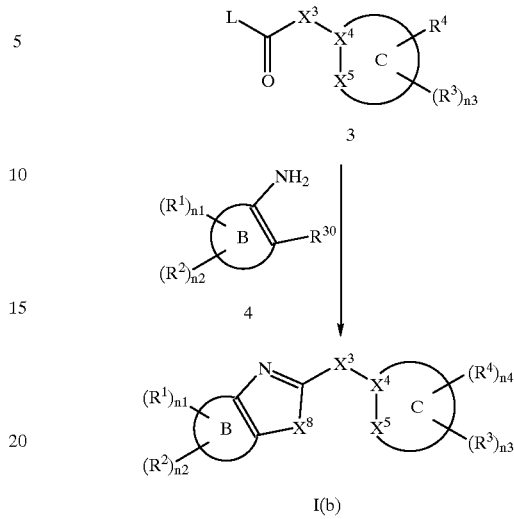

Scheme 2

I(b)

in which L is a leaving group, $R^{30}$ is —OH, —$NHR^5$ or —SH, $X^8$ is —O—, —$NR^6$— or —S— and n2, n3, n4, B, C, $X^1$, $X^3$, $X^4$, $X^5$, $R^1$, $R^2$, $R^3$, $R^4$ and $R^6$ are as defined in the Summary of the Invention (e.g., see Examples 2(e) and 7(h), infra.).

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography (HPLC), or a combination of these procedures. Specific illustrations of suitable separation and isolation procedures can be had by reference to the examples hereinbelow. However, other equivalent separation or isolation procedures can, of course, be used. Nuclear magnetic resonance (NMR) spectra were recorded on a General Electric "QE Plus" spectrometer (300 MHz). Infrared (IR) spectra were recorded on a Perkin-Elmer 1600 Fourier Transform IR (FTIR). Analytical HPLC was performed on a Ultrafast Microprotein Analyzer, Michrom BioResources, Inc. equipped with a PLRP column, 1 mm×150 mm. Preparative HPLC was performed on a Gilson LC using a VYDAC 1×25 cm $C_{18}$ reverse phase (RP) column or a Waters Prep LC2000 system using a Vydac 5×25 cm $C_{18}$ RP column. Mass spectra (MS) were obtained on a Finnigan SSQ 710 with an ESI source by direct infusion or by HPLC MS (Ultrafast Microprotein Analyzer, $C_{18}$ column 2 mm×150 mm). Unless otherwise noted, all reagents and equipment were either prepared according to published procedures or were purchased from commercial sources, such as Aldrich Chemical Co. (Milwaukee, Wis.), Sigma Chemical Co. (St. Louis, Mo.) and ICN Chemical Co. (Irvine, Calif.). The techniques used to perform the syntheses described below will be recognized by those of skill in the art as routine (see, e.g., March, Larock, or Furniss, supra).

Additional Processes for Preparing Compounds of Formula I

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0 to 80° C.

Prodrug derivatives of the compounds of Formula I can be prepared by methods known to those of ordinary skill in the art (e.g., see Example 12, infra.). For further details on prodrugs and their preparation see Saulnier et al. (994), *Bioorganic and Medicinal Chemistry Letters*. 4:1985).

Protected derivatives of the compounds of Formula I can be made by means known to those of ordinary skill in the art. A detailed description of the techniques applicable to the creation of protective groups and their removal can be found in T. W. Greene, *Protective Groups in Organic Synthesis*, John Wiley & Sons, Inc. 1981.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these disimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, Honh Wiley & Sons, Inc. (1981).

In summary, an aspect of this Invention is a process for preparing a compound of Formula I, which process comprises:

(a) reacting a compound of Formula 1:

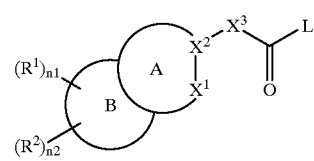

or a protected derivative thereof, with a compound of Formula 2:

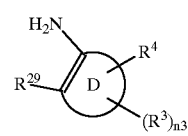

or a protected derivative thereof, in which L is a leaving group, D together with the vinylene moiety to which it is fused comprises a monocyclic or fused bicyclic divalent radical containing from 5 to 15 annular atoms, wherein each ring contains 5 to 7 annular atoms and each annular atom optionally is a heteroatom, $R^{29}$ is —OH, —NHR$^6$ or —SH and n1, n2, n3, A, B, $X^1$, $X^2$, $X^3$, $R^1$, $R^2$, $R^3$, $R^4$ and $R^6$ are as defined in the Summary of the Invention, and then deprotecting if necessary to give a compound of Formula I in which $X^4$ and $X^5$ are adjacent members of an oxazol-2-yl, 1H-imidazol-2-yl or thiazol-2-yl, ring; or (b) reacting a compound of Formula 3:

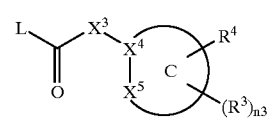

or a protected derivative thereof, with a compound of Formula 4:

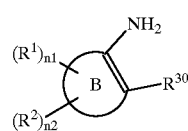

or a protected derivative thereof, in which L is a leaving group, $R^{30}$ is —OH, —NHR$^5$ or —SH and n1, n2, n3, B, C, $X^3$, $X^4$, $X^5$, $R^1$, $R^2$, $R^3$, $R^4$ and $R^5$ are as defined in the Summary of the Invention, and then deprotecting if necessary to give a compound of Formula I in which $X^1$ and $x^2$ are adjacent members of an oxazol-2-yl, 1H-imidazol-2-yl or thiazol-2-yl ring;

(c) optionally further converting a compound of Formula I into a pharmaceutically acceptable salt;

(d) optionally further converting a salt form of a compound of Formula I to non-salt form;

(e) optionally further converting an unoxidized form of a compound of Formula I into a pharmaceutically acceptable N-oxide;

(f) optionally further an N-oxide form of a compound of Formula I its unoxidized form;

(g) optionally further converting a non-derivatized compound of Formula I into a pharmaceutically prodrug derivative; and (h) optionally further converting a prodrug derivative of a compound of Formula I to its non-derivatized form.

EXAMPLES

The following examples are provided merely for the purposes of illustration and are not to be construed in any way as limiting the scope of the present invention. Those skilled in the art will recognize that certain variations and modifications can be practiced within the scope of the invention.

Example 1

2-Naphth-2-ylethylamine

A solution comprising 2-naphth-2-ylethanol (0.5 g, 2.9 mmol) in dry DMF (5 mL) was combined under nitrogen with diphenylphosphoryl azide (0.74 mL, 3.42 mmol) and 1,8-diazaabicyclo[5.4.0]undec-7-ene (0.47 mL. 3.14 mmol). The mixture was heated at 65° C. for 3 hours and then partitioned between water and diethyl ether. The aqueous layer was separated and extracted with diethyl ether. The combined organic layers were washed with 3N hydrochloric acid and then saturated sodium bicarbonate, dried (MgSO$_4$), filtered and concentrated by rotary evaporation. The residue was dissolved in THF (5 mL) and the solution was combined with triphenylphosphine (1 g, 3.81 mmol), stirred for 2 hours at room temperature, diluted with water (0.100 mL), stirred 3 hours, diluted with concentrated hydrochloric acid (0.33 mL) to give a precipitate, treated with ethanol (5 mL) to dissolve the precipitate and treated with diethyl ether, added slowly, to give a white precipitate. The while precipitate was isolated by filtration, washed with diethyl ether and dried under vacuum to provide 2-naphth-2-ylethylamine hydrochloride (0.447 g, 75% yield);

$^1$H-NMR (300 Mhz, DMSO-d$_6$): 8.18 (br s, 3H), 7.82–7.88 (m, 3H), 7.74 (s, 1H), 7.38–7.48 (m, 3H), 3.07 (m, 4H).

Proceeding as in Example 1 the following intermediate amines were prepared:

2-naphth-1-ylethylamine, yield=56%, $^1$H-NMR (300 Mhz, DMSO-d$_6$): 8.26 (br s, 3H), 8.16 (d, 1H, J=8.1 Hz), 7.92 (dd, 1H, J=1.5, 7.8 Hz), 7.81 (dd, 1H, J=1.2, 7.5 Hz), 7.40–7.56 (m, 4H), 3.37 (m, 2H), 3.05 (t, 2H, J=7.4 Hz);

3-cyclohexylpropylamine, yield=40%, 1H-NMR (300 Mhz, CDCL$_3$): 2.68 (t, 2H, J=7.2 Hz), 2.17 (br s, 2H), 1.64–1.71 (m, 5H), 1.46 (m, 2H), 1.18 (m, 6H) 0.87 (m, 2H);

3-phenyl-2-propenylamine, yield=53%, $^1$H-NMR (300 Mhz, DMSO-d$_6$): 8.39 (br s, 3H), 7.26–7.41 (m, 5H), 6.72 (d, 1H, J=16.2 Hz), 6.29 (dt, 1H, J=16.2, 6.6 Hz), 3.56 (d, 2H, J=6.6 Hz);

3-phenyl-2-propynylamine, yield=62%, $^1$H-NMR (300 Mhz, DMSO-d$_6$): 8.67 (br s, 2H), 7.38–7.42 (m, 5H), 3.91 (m, 2H); and 3,3-diphenylpropylamine, yield=50%, $^1$H-NMR (300 Mhz, DMSO-d$_6$): 8.10 (br s, 3H), 7.30 (m, 8H), 7.19 (m, 2H), 4.11 (t, 1H, J=7.9 Hz), 2.62 (m, 2H) 2.33 (m, 2H).

Example 2

2-(5-Aminomethyl-1H-benzoimidazol-2-ylmethyl)-N-(4-phenylbutyl)-1H-benzoimidazole-5-carboxamide trifluoroacetate (Compound 1)

(a) Ethyl cyanoacetate (8 mL, 75 mmol) in anhydrous benzene (100 mL) was combined under nitrogen with anhydrous ethanol (6 mL, 105 mmol). The mixture was cooled to 10° C. (ice/acetone) and bubbled 20 minutes with dry hydrogen chloride gas. The mixture was slowly warmed to room temperature, sealed and stirred for approximately 18 hours. The mixture was diluted with diethyl ether (400 mL) and let stand for 5 hours at room temperature to give a crystalline solid. The solid was isolated by filtration, washed several times with anhydrous diethyl ether and dried to provide ethyl 3-ethoxy-3-iminopropionate (13.2 g, 90% yield) as a colorless, crystalline solid; $^1$H-NMR (300 Mhz, CDCL$_3$): 7.84 (d, 1H, J=10.0 Hz), 7.19–7.36 (m, 5H), 7.00–7.06 (m, 2H), 4.10 (t, 2H, J=5.7 Hz), 2.73 (t, 2H, J=6.5 Hz), 1.89 (m, 4H).

(b) A mixture of 3,4-diaminobenzoic acid (9.4 g, 62 mmol), ethyl 3-ethoxy-3-iminopropionate and glacial acetic acid (15 mL) was stirred 30 minutes at 110° C. under nitrogen. The mixture was poured over crushed ice (50 mL) and stirred 30 minutes to give a dark yellow oil. The mixture was stirred while diethyl ether (25 mL) was added to give a gray precipitate. The precipitate was isolated by filtration, washed several times with diethyl ether and dried under vacuum to provide 2-ethoxycarbonylmethyl-1H-benzoimidazole-5-carboxylic acid (12.6 g, 83% yield); $^1$H-NMR (300 Mhz, DMSO-d$_6$): 12.77 (broad s, 1H), 8.10 (s, 1H), 7.79 (d, 1H, J=8.4 Hz), 7.57 (d, 1H, J=8.4 Hz), 4.11 (q, 2H, J=7.1 Hz), 4.02 (s, 2H), 1.17 (t, 3H, J=7.1 Hz).

(c) A mixture of dinitrophenylmethanol (22 g, 111 mmol), triphenylphosphine (34.5 g, 131 mmol) and phthalimide (17.6 g, 119 mmol) in THF (450 mL) was stirred at −10° C. (ice/acetone) under nitrogen while diethyl azodicarboxylate (20.7 mL, 131 mmol) was added dropwise. The mixture was stirred 2 hours at −10° C. and then diluted with diethyl ether (900 mL) and stored at −20° C. for approximately 18 hours to give a crystalline solid. The solid was isolated by filtration and washed to provide 2-(3,4-dinitrobenzyl)isoindole-1,3-dione (24.6 g, 67% yield) as an off-white crystalline solid; $^1$H-NMR (300 Mhz, DMSO-d6): 7.87–7.94 (m, 5H), 7.74–7.82 (m, 2H), 4.96 (s, 2H).

(d) A mixture of 2-(3,4-dinitrobenzyl)isoindole-1,3-dione (8 g, 24.4 mmol), prepared as in Example 1, and 10% palladium on carbon (300 mg) was combined with anhydrous ethanol (200 mL, anhydrous THF (100 mL) and glacial acetic acid (30 mL) under a continuous stream of nitrogen. The mixture then was stirred vigorously 15 hours at room temperature under hydrogen, filtered and concentrated to a volume of approximately 30 mL by rotary evaporation. The mixture was diluted with water (100 mL) and ammonium hydroxide was added to give an orange precipitate. The precipitate was isolated by filtration and washed several times with water to provide 2-(3,4-diaminobenzyl)isoindole-1,3-dione (6 g, 91% yield); $^1$H-NMR (300 Mhz, DMSO-d$_6$): 7.76–7.85 (m, 4H), 6.31–6.43 (m, 3H), 4.51 (broad s, 4H), 4.47 (s, 2H).

(e) A finely ground mixture of 2-(3,4-diaminobenzyl) isoindole-1,3-dione (2.0 g, 7.5 mmol) and 2-ethoxycarbonylmethyl-1H-benzimidazole-5-carboxylic acid (0.93 g, 3.75 mmol) was heated 1 hour at 185° C. under nitrogen. The mixture was suspended in 1:1 methylene chloride/ethanol (20 mL) and stirred vigorously for 1 hour. The solids were collected by filtration, washed with 1:1 methylene chloride/ethanol (3×20 mL) and dried to provide 2-[5-(1,3-dioxo-1,3-dihydroisoindol-2-ylmethyl)-1H-benzoimidazol-2-ylmethyl]-1H-benzoimidazole-5-carboxylic acid (0.98 g, 29% yield); $^1$H-NMR (300 Mhz, DMSO-$d_6$): 12.45 (broad s, 1H), 8.07 (s, 1H), 7.80–7.83 (m, 6H), 7.51 (d, 1H, J=7.5 Hz), 7.43 (s, 1H), 7.11 (d, 1H, J=7.2 Hz), 4.82 (s, 2H), 4.48 (s, 2H).

(f) 2-[5-(1,3-Dioxo-1,3-dihydroisoindol-2-ylmethyl)-1H-benzoimidazol-2-ylmethyl]-1H-benzoimidazole-5-carboxylic acid (0.05g, 0.111 mmol) was dissolved in anhydrous dimethylformamide (0.5 mL) and the solution was combined with 1-hydroxybenzotriazole hydrate (0.017 g, 0.126 mmol), benzotriazole-1-yloxytrispyrrolidinophosphoniurnhexafluoro-phosphate (0.063 g, 0.121 mmol) and N-methylmorpholine (0.013 mL, 0.118 mmol) at room temperature under an atomosphere of dry $N_2$. After 2 minutes 4-phenylbutylamine (0.02 mL, 0.127 mmol) was added and the mixture was stirred at room temperature for 2 hours. The mixture was transferred to a sparatory funnel containing 20% ethanol/ethyl acetate solution (7 mL), 0.2N HCl (3.5 mL) and saturated aqueous NaCl (3.5 mL). The aqueous phase was extracted once with 20% ethanol/ethyl acetate solution (7 mL) and the combined organic phases were washed with a solution containing 0.2N HCl (3.5 mL) in saturated aqueous NaCl (3.5 mL) followed by a final washing with saturated aqueous sodium bicarbonate solution (7 mL). The organic phase was then dried over anhydrous sodium sulfate, filtered and concentrated to dryness on a rotary evaporator to provide 2-[5-(1,3-dioxo-1,3-dihydroisoindol-2-ylmethyl)-1H-benzoimidazol-2-ylmethyl]-N-(3-phenylpropyl)-1H-benzoimidazole-5-carboxamide as crude material (0.14 g).

(g) 2-[5-(1,3-Dioxo-1,3-dihydroisoindol-2-ylmethyl)-1H-benzoimidazol-2-ylmethyl]-N-(3-phenylpropyl)-1H-benzoimidazole-5-carboxamide (0.14 g, crude material) was dissolved in anhydrous ethanol (0.5 mL) and the solution combined with anhydrous hydrazine (0.15 mL, 0.48 mmol). The mixture was heated at reflux under $N_2$ for 1 hour and then concentrated on a rotary evaporator. The residue was place under vacuum (0.15 torr) for 2 hours to remove excess hydrazine. The residue was diluted with 3 M HCl (0.5 mL) and the mixture was heated at 50° C. for 20 minutes. The reaction mixture was cooled to room temperature and stirred for an additional 20 minutes to give a solid precipitate. The precipitate was isolated by filtration and washed with water (4×1.5 mL). The filtrates were combined and washed with 20% ethanol/ethyl acetate solution (2×7 mL). The combined aqueous phases were lyophilization to give crude product as a hydrochloride salt. The crude material was purified by preparative reverse phase HPLC to provide 2-[5-(1,3-dioxo-1,3-dihydroisoindol-2-ylmethyl)-1H-benzoimidazol-2-ylmethyl]-N-(3-phenylpropyl)-1H-benzoimidazole-5-carboxamide (0.04 g, 0.07 mmol) as a white solid; $^1$H-NMR (300 Mhz, $CD_3OD$): 8.14 (s, 1H), 7.84–7.89 (m, 2H), 7.77 (d, 1H, J=8.1 Hz), 7.71 (d, 1H, J=8.1 Hz), 7.56 (d, 1H, J=8.1 Hz), 7.12–7.27 (m, 5H), 4.29 (s, 2H), 3.43 (t, 2H, J=7.2 Hz), 2,66 (t, 2H, J=7.2 Hz), 1.69 (m, 4H).

Proceeding as in Example 2 the following compounds of the invention were prepared:

2-(5-aminomethyl-1H-benzoimidazol-2-ylmethyl)-N-naphth-1-ylmethyl-1H-benzoimidazole-5-carboxamide (Compound 2), $^1$H-NMR (300 Mhz, $CD_3OD$): 8.13 (m, 2H), 7.88 (m, 2H), 7.80 (m, 2H), 7.73 (d, 1H, J=7.9 Hz), 7.67 (d, 1H, J=7.9 Hz), 7.38–7.54 (m, 5H), 5.01 (s, 2H), 4.26 (s, 2H);

2-(5-aminomethyl-1H-benzoimidazol-2-ylmethyl)-N-benzyl-1H-benzoimidazole-5-carboxamide (Compound 3), $^1$H-NMR (300 Mhz, $CD_3OD$): 8.18 (s, 1h), 7.91 (d, 1H, J=7.9 Hz), 7.82 (s, 1H), 7.76 (d, 1H, J=7.9), 7.72 (d, 1H, J=7.9 Hz), 7.54 (d, 1H, J=7.9 Hz), 7.23–7.38 (m, 5H), 4.60 (s, 2H), 4.28 (s, 2H);

2-(5-aminomethyl-1H-benzoimidazol-2-ylmethyl)-N-(3-phenylpropyl)-1H-benzoimidazole-5-carboxamide (Compound 4), $^1$H-NMR (300 Mhz, $CD_3OD$): 8.14 (s, 1H), 7.87 (d, 1H, J=8.6 Hz), 7.8 (s, 1H), 7.76 (d, 1H, J=8.6 Hz), 7.71 (d, 1H, J=8.6 Hz), 7.54 (d, 1H, J=8.6 Hz), 7.24 (m, 4H), 7.16 (m, 1H), 4.28 (s, 2H), 3.46 (t, 2H, J=7.9 Hz), 2.95 (t, 2H, J=7.9 Hz), 1.62 (quintet, 2H, 7.9 Hz);

2-(5-aminomethyl-1H-benzoimidazol-2-ylmethyl)-N-(2-phenylethyl)-1H-benzoimidazole-5-carboxamide (Compound 5), $^1$H-NMR (300 Mhz, DMSO-$d_6$): 8.12 (s, 1H), 7.83 (m, 2H), 7.78 (d, 1H, J=9.3 Hz), 7.71 (d, 1H, J=9.3 Hz), 7.55 (d, 1H, J=9.3 Hz), 7.29 (m, 4H), 7.22 (m, 1H), 4.29 (s, 2H), 3.65 (t, 2H, J=7.9 Hz), 2.95 (t, 2H, J=7.9 Hz);

2-(5-aminomethyl-1H-benzoimidazol-2-ylmethyl)-N-(3-aminomethyl)benzyl-1H-benzoimidazole-5-carboxamide (Compound 6), 1H-NMR (300 Mhz, DMSO-$d_6$): 9.31 (t, 1H, J=5.7 Hz), 8.58 (br s, 3H), 8.41 (br s, 3H), 8.28 (s, 1H), 7.97 (m, 2H), 7.79 (d, 1H, J=9.3 Hz), 7.75 (d, 1H, J=9.3 Hz), 7.59 (d, 1H, J=9.3 Hz), 7.43 (s, 1H), 7.35 (s, 3H), 5.07 (s, 2H), 4.50 (m, 2H), 4.18 (m, 2H), 3.97 (m, 2H);

2-(5-aminomethyl-1H-benzoimidazol-2-ylmethyl)-N-(2-aminoethyl)-1-methyl-1H-benzoimidazole-5-carboxamide (Compound 7), $^1$H-NMR (300 Mhz, DMSO-$d_6$): 8.86 (br, 1H), 8.50 (br s, 3H), 8.24 (s, 1H), 8.08 (br s, 3H), 7.93 (m, 2H), 7.77 (d, 1H, J=8.7 Hz), 7.55 (d, 1H, J=9.2 Hz), 5.02 (br, s, 2H), 4.16 (m, 2H), 3.94 (s, 2H), 3.50 (m, 2H), 2.96 (m, 2H);

2-(5-aminomethyl-1H-benzoimidazol-2-ylmethyl)-N-(2-aminoethyl)-1H-benzoimidazole-5-carboxamide (Compound 8), $^1$H-NMR (300 Mhz, DMSO-$d_6$): 8.97 (t, 1H, J=4.3 Hz), 8.58 (br s, 3H), 8.31 (s, 1H), 8.16 (br s, 3H), 7.97 (m, 2H), 7.79 (d, 1H, J=10 Hz), 7.73 (d, 1H, J=10 Hz), 7.59 (d, 1H, J=10 Hz), 5.09 (s, 1H), 4.19 (m, 2H), 3.54 (m, 2H), 2.99 (m, 2H);

2-(5-aminomethyl-1H-benzoimidazol-2-ylmethyl)-N-(4-aminobutyl)-1H-benzoimidazole-5-carboxamide (Compound 9), $^1$H-NMR (300 Mhz, DMSO-$d_6$): 8.77 (t, 1H, J=5.7 Hz), 8.61 (br s, 3H), 8.24 (s, 1H), 7.90–8.02 (m, 5H), 7.78 (d, 1H, J=9.3 Hz), 7.74 (d, 1H, J=9.3 Hz), 7.60 (d, 1H, J=9.3 Hz), 5.09 (s, 2H), 4.18, (m, 2H), 3.28 (m, 2H), 2.78 (m, 2H), 1.12 (m, 4H);

2-(5-aminomethyl-1H-benzoimidazol-2-ylmethyl)-N-(3-aminopropyl)-1H-benzoimidazole-5-carboxamide (Compound 10), $^1$H-NMR (300 Mhz, DMSO-$d_6$): 8.9 (t, 1H, J=5.0 Hz), 8.53 (br s, 3H), 8.23 (s, 1H), 7.97 (br s, 3H), 7.94 (s, 1H), 7.89 (d, 1H, J=8.6 Hz), 7.78 (d, 1H, J=8.6 Hz), 7.71 (d, 1H, J=8.6), 7.57 (d, 1H, J=8.6 Hz), 5.03 (s, 2H(, 4,40 (m, 2H), 3,34 (m, 2H), 2.81 (m, 2H), 1.81 (m, 2H); and 2-(5-aminomethyl-1H-benzoimidazol-2-ylmethyl)-N-cyclohexylmethyl-1H-benzoimidazole-5-carboxamide (Compound 11), $^1$H-NMR (300 Mhz, $CD_3OD$): 8.15 (s, 1H), 7.88 (d, 1H, J=7.6 Hz), 7.84 (s, 1H), 7.76 (d, 1H, J=7.6 hz), 7.72 (d, 1H, J=7.6 Hz), 7.54 (d, 1H, J=7.6 Hz), 4.29 (s, 2H), 3.26 (d, 2H, J=7.2 Hz), 1.64–1.86 (m, 6H), 1.20–1.37 (m, 3H), 0.95–1.09 (m, 2H).

Example 3

2-(5-Aminomethyl-1H-benzoimidazol-2-ylmethyl)-N-(3-aminopropyl)-1-methyl-1H-benzoimidazole-5-carboxamide (Compound 12)

(a) A mixture comprising 3-nitro-4-chlorobenzoic acid (1.3 g, 6.45 mmol), 10% methylamine and water (10 mL) in a sealed tube was heated at 100° C. for 11 hours, concentrated to 1 mL and then diluted with concentrated hydrochloric acid to give a yellow precipitate. The precipitate was isolated by filtration, washed with water and then diethyl ether and dried to provide 3-nitro-4-methylaminobenzoic acid (2.1 g, 86% yield); $^1$H-NMR (300 Mhz, CDCL$_3$): 8.56 (d, 1H, J=2.1 Hz), 8.52 (q, 1H, J=8.6 Hz), 7.94 (dd, 1H, 9.3, 2.1 Hz), 7.00 (d, 1H, J=9.3 Hz), 2.97 (d, 3H, J=8.6 Hz).

(b) Ethyl alcohol (100 mL) was added to a flask containing 3-nitro-4-methylaminobenzoic acid (2.09 g, 10.7 mmol) and 10% Pd/C (30 mg) under a steady stream of N$_2$. The mixture was stirred under hydrogen for 16 hours, filtered through a milipore 0.22 μm type GV filter disc and concentrated on a rotary evaporator. The residue was dried under vaccum to provide 3-amino-4-methylaminobenzoic acid (1.1 g, 61% yield).

(c) Ethyl 3-ethoxy-3-iminopropionate, prepared as in Example 2(a), was reacted with 3-amino-4-methylaminobenzoic acid under conditions similar to that set forth in Example 2(b) to provide 2-ethoxycarbonylmethyl-1-methyl-1H-benzoimdazole-5-carboxylic acid (71% yield); $^1$H-NMR (300 Mhz, DMSO-d$_6$): 7.18 (dd, 1H, J=8.1 Hz), 7.11 (d, 1H, J=1.2 Hz), 6.33 (d, 1H, J=8.1 Hz), 5.28 (br s, 1H), 4.67 (br s, 1H), 3.34 (br s, 2H), 2.72 (s, 3H).

(d) 2-(3,4-Diaminobenzyl)isoindole-1,3-dione, prepared as in Example 2(d), was reacted with 2-ethoxycarbonylmethyl-1-methyl-1H-benzoimidazole-5-carboxylic acid under conditions similar to that set forth in Example 2(e) to provide 2-[5-(1,3-dioxo-1,3-dihydroisoindol-2-ylmethyl)-1H-benzoimidazol-2-ylmethyl]-1-methyl-1H-benzoimidazole-5-carboxylic acid (48% yield); $^1$H-NMR (300 Mhz, DMSO-d$_6$): 8.10 (s, 1H), 7.80–7.84 (m, 5H), 7.57 (d, 1H, J=10.0 Hz), 7.40 (br s, 2H), 7.10 (br s, 1H), 4.80 (s, 2H), 4.56 (s, 2H), 3.79 (s, 3H).

(e) 2-[5-(1,3-Dioxo-1,3-dihydroisoindol-2-ylmethyl)-1H-benzoimidazol-2-ylmethyl]-1-methyl-1H-benzoimidazole-5-carboxylic acid (0.05 g, 0.108 mmol), 1-hydroxybenzotriazole (0.016 g, 0.118 mmol), 1-(3-dimethylaminopropyl)-3-ethylcarbodiimide hydrochloride (0.023 g, 0.12 mmol) and the mono-BOC protected derivative of 1,3-diaminopropane were dissolved at 0° C. in methylene chloride (1 mL) and DMF (minimal amount sufficient to effect a solution). The solution was adjusted to pH-8 with N-methylmorpholine and the mixture was allowed to slowly warm to room temperature and then stirred for 20 hours. The mixture was transferred to a separatory finnel, diluted with methylene chloride, washed with 0.1N HCl solution and then saturated NaHCO$_3$ solution, dried over sodium sulfate, filtered and concentrated. The residue was purified by preparatory TLC (10% methanol/ethyl acetate) to provide 2-[6-(1,3-dioxo-1,3-dihydroisoindol-2-ylmethyl)-1H-benzoimidazol-2-ylmethyl]-1-methyl-N-(3-aminopropyl)-1H-benzoimidazole-5-carboxamide (0.02 g, 28% yield); $^1$H-NMR (300 Mhz, CDCL$_3$): 7.75–7.81 (m, 4H), 7.61–7.68 (m, 3H), 7.33 (br s, 1H), 7.27 (d, 1H, J=8.6 Hz), 7.15 (d, 1H, J=9.3 Hz), 5.10 (br t, 1H), 4.90 (br s, 2H), 4.57 (s, 2H), 3.71 (s, 3H), 3.49 (q, 2H, J=7.2 Hz), 3.24 (q, 2H, J=7.2 Hz), 1.72 (m, 2H), 1.41 (s, 9H);

(f) The 2-[6-(1,3-dioxo-1,3-dihydroisoindol-2-ylmethyl)-1H-benzoimidazol-2-ylmethyl]-1-methyl-N-(3-aminopropyl)-1H-benzoimidazole-5-carboxamide was deprotected under conditions similar to that set forth in Example 2(g) to provide 2-(5-aminomethyl-1H-benzoimidazol-2-ylmethyl)-N-(3-aminopropyl)-1-methyl-1H-benzoimidazole-5-carboxamide (20% yield); $^1$H-NMR (300 Mhz, DMSO-d$_6$): 8.85 (t, 1H, J=5.7 Hz), 8.55 (br s, 3H), 8.20 (s, 1H), 8.01 (br s, 3H), 7.74 (m, 2H), 7.80 (d, 1H, J=6.6 Hz), 5.07 (s, 2H), 4.16 (m, 2H), 3.96 (s, 3H), 3.32 (m, 2H), 2.79 (m, 2H), 1.80 (m, 2H).

Proceeding as in Example 3 the following compounds of the invention were prepared:

3-[2-(5-aminomethyl-1H-benzoimidazol-2-ylmethyl)-N-(2-naphth-1-ylethyl)-1H-benzoimidazole-5-carboxamide (Compound 13), $^1$H-NMR (300 Mhz, CD$_3$OD): 8.25 (d, 1H, J=8.1 Hz), 8.09 (s, 1H), 7.67–7.86 (m, 6H), 7.37–7.54 (m, 5H), 4.27 (s, 2H), 3.73 (t, 2H, J=7.4 Hz), 3.41 (t, 2H, J=7.4 Hz);

2-(5-aminomethyl-1H-benzoimidazol-2-ylmethyl)—N-(3,3-diphenylpropyl)-1H-benzoimidazole-5-carboxamide (Compound 14),$^1$H-NMR (300 Mhz, CD$_3$OD): 8.11 (s, 1H), 7.77–7.86 (m, 3H), 7.70 (d, 1H, J=9.3), 7.56 (d, 1H, J=9.3 Hz), 7.23–7.39 (m, 8H), 7.13–7.19 (m, 2H), 4.30 (s, 2H), 4.07 (t, 1H, J=7.2 Hz), 3.40 (t, 2H, J=7.2 Hz), 2,44 (q, 2H, J=7.2 Hz);

2-(5-aminomethyl-1H-benzoimidazol-2-ylmethyl)-N-(2-naphth-2-ylethyl)-1H-benzoimidazole-5-carboxamide (Compound 15),$^1$H-NMR (300 Mhz, CD$_3$OD): 8.10 (s, 1H), 7.67–7.86 (m, 8H), 7.55 (d, 1H, J=10.0 Hz), 7.38–7.44 (m, 3H), 4.28 (s, 2H), 3.72 (t, 2H, J=7.2 Hz), 3.10 (t, 2H, J=7.2 Hz);

2-(1H-benzoimidazol-2-ylmethyl)-N-[2-(1H-indol-3-yl)ethyl]-1H-benzoimidazole-5-carboxamide (Compound 16),$^1$H-NMR (300 Mhz, CD$_3$OD): 8.09 (s, 1H), 7.81–7.84 (m, 2H), 7.74 (d, 1H, J=8.6 Hz), 7.67 (d, 1H, J=8.6 Hz), 7.52–7.58 (m, 2H), 7.30 (d, 1H, J=7.9), 7.01–7.08 (m, 2H), 6.94 (t, 1H, J=7.9 Hz), 4.26 (s, 2H), 3.68 (t, 2H, J=6.8 Hz), 3.06 (t, 2H, J=6.8 Hz);

2-(5-aminomethyl-1H-benzoimidazol-2-ylmethyl)-N-[2-(5-methoxy)indol-3-yl]-1H-benzoimidazole-5-carboxamide (Compound 17),$^1$H-NMR (300 Mhz, CD$_3$OD): 8.10 (s, 1H), 7.81–7.85 (m, 2H), 7.76 (d, 1H, J=8.2 Hz), 7.69 (d, 1H, J=8.2 Hz), 7.54 (d, 1H, J=8.2 Hz), 7.20 (d, 1H, J=8.2 Hz), 7.07 (m, 2H), 6.70 (dd, 1H, J=10.0, 2.2 Hz), 4.27 (s, 2H), 3.65–3.71 (m, 5H), 3.04 (t, 2H, J=7.2 Hz);

2-(5-aminomethyl-1H-benzoimidazol-2-ylmethyl)-N-(2,3,4,5,6-pentahydroxyhexyl)-1H-benzoimidazole-5-carboxamide (Compound 18), $^1$H-NMR (300 Mhz, CD$_3$OD/D$_2$O(1/1)): 8.15 (s, 1H), 7.86–7.90 (m, 2H), 7.83 (d, 1H, J=9.6 Hz), 7.77 (d, 1H, J=9.6 Hz), 7.61 (d, 1H, J=9.6 Hz), 4.32 (s, 2H), 4.01 (m, 1H), 3.62–3.86 (m, 6H), 3.47–3.55 (m, 1H);

2-(5-aminomethyl-1H-benzoimidazol-2-ylmethyl)-N-(2-phenoxyethyl)-1H-benzoimidazole-5-carboxamide (Compound 19),$^1$H-NMR (300 Mhz, CD$_3$OD): 8.16 (s, 1H), 7.88 (d, 1H, J=9.3 Hz), 7.84 (s, 1H), 7.76 (d, 1H, J=9.3 Hz), 7.71 (d, 1H, J=9.3 Hz), 7.55 (d, 1H, J=9.3

Hz), 7.23 (2H, J=7.9 Hz), 6.85–6.96 (m, 3H), 4.27 (s, 2H), 4.16 (t, 2H, J=6.1 Hz), 3.78 (t, 2H, J=6.1 Hz);

2-(5-aminomethyl-1H-benzoimidazol-2-ylmethyl)-N-(3-phenylprop-2-ynyl)-1H-benzoimidazole-5-carboxamide (Compound 20), $^1$H-NMR (300 Mhz, CD$_3$OD): 8.18 (s, 1H), 7.91 (d, 1H, J=9.3 Hz), 7.84 (s, 1H), 7.76 (d, 1H, J=9.3), 7.71 (d, 1H, J=9.3 Hz), 7.55 (d, 1H, J=9.3 Hz), 7.38–7.43 (m, 2H), 7.28–7.32 (m, 3H), 4.40 (s, 2H), 4.27 (s, 2H);

2-(5-aminomethyl-1H-benzimidazol-2-ylmethyl)-N-(E-3-phenylallyl)-1H-benzimidazole-5-carboxamide (Compound 21), $^1$H-NMR (300 Mhz, CD$_3$OD): 8.19 (s, 1H), 7.92 (d, 1H, J=9.3 Hz), 7.86 (s, 1H), 7.76 (d, 1H, J=9.3 Hz), 7.71 (d, 1H, J=9.3 Hz), 7.55 (d, 1H, J=9.3 Hz), 7.33–7.39 (m, 2H), 7.18–7.30 (m, 3H), 6.60 (d, 1H, J=15.8 Hz), 6.34 (dt, 1H, J=15.8, 6.1 Hz), 4.27 (s, 2H), 4.17 (d, 2H, J=6.1 Hz);

2-(5-aminomethyl-1H-benzoimidazol-2-ylmethyl)-N-(3-cyclohexylpropyl)-1H-benzoimidazole-5-carboxamide (Compound 22), 1H-NMR (300 Mhz, CD$_3$OD): 8.13 (s, 1H), 7.86 (d, 1H, J=9.3 Hz), 7.81 (s, 1H), 7.74 (d, 1H, J-9.3 Hz), 7.69 (d, 1H, J=9.3 Hz), 7.53 (d, 1H, J=9.3 Hz), 4.27 (s, 2H), 3.36 (t, 2H, J=7.2 Hz), 1.61–1.78 (m, 7H), 1.19–1.32 (m, 6H). 0.90 (m, 2H);

3-[2-(5-aminomethyl-1H-benzoimidazol-2-ylmethyl)-N-oct-1-yl-1H-benzimidazole-5-carboxamide (Compound 23), $^1$H-NMR (300 Mhz, CD$_3$OD): 8.13 (s, 1H), 7.86 (d, 1H, J=9.7 Hz), 7.82 (s, 1H), 7.74 (d, 1H, J=9.7 Hz), 7.69 (d, 1H, J=9.7), 7.49 (d, 1H, J=9.7 Hz), 4.27 (s, 2H), 3.39 (t, 2H, J=7.2 Hz), 1.64 (m, 2H), 1.26–1.43 (m, 11 H), 0.88 (m, 2H);

2-(5-aminomethyl-1H-benzoimidazol-2-ylmethyl)-N-methyl-N-(2-phenylethyl)-1H-benzimidazole-5-carboxamide (Compound 24), $^1$H-NMR (300 Mhz, CD$_3$OD): 7.76 (s), 7.69 (d), 7.63 (d), 7.44–7.55 (m), 7.20–7.28 (m), 7.09–7.14 (m), 6.97 (d), 6.85 (br s), 4.19 (s), 3.72 (t), 3.47 (t), 3.22 (s), 3.08 (s), 2.87 (t), 2.76 (t); and 2-(5-aminomethyl-1H-benzoimidazol-2-ylmethyl)-N-(1-methyl-3-phenylpropyl)-1H-benzoimidazole-5-carboxamide (Compound 25), $^1$H-NMR (300 Mhz, CD$_3$OD): 8.05 (s, 1H), 7.79 (d, 1H, J=9.3 Hz), 7.75 (s, 1H), 7.68 (d, 1H, J=9.3 Hz), 7.63 (d, 1H, J=9.3 Hz), 7.46 (d, 1H, J=9.3 Hz), 7.09–7.17 (m, 4H), 7.03 (m, 1H), 4.43 (s, 2H), 4.08 (m, 1H), 2.61 (t, 2H, J=7.9 Hz), 1.17–1.93 (m, 2H), 1.18 (d, 3H, J=7.2 Hz).

Example 4

C-{2-[5-(4-phenylbutoxy)-1H-benzoimidazol-2-ylmethyl]-1H-benzoimidazol-5-yl}methylamine (Compound 26)

(a) 4-Phenyl-1-butanol (1 mL, 6.49 mmol) in THF (3 mL) was combined under dry nitrogen with sodium hydride (0.26 g, 6.5 mmol) in a 60% mineral oil dispersion. The mixture was stirred vigorously for 5 minutes, combined with 3,4-dinitrochlorobenzene (1.3 g, 6.42 mmol) and then stirred 10 hours at room temperature. The mixture was partitioned between diethyl ether and 3N hydrochloric acid. The aqueous layer was separated and extracted several times with diethyl ether. The combined organic layers were dried (MgSO$_4$), filtered and concentrated by rotary evaporation. The residue was purfied by flash chromatography (9:1 hexanes/diethyl ether) to provide 4-(4-phenylbutoxy)-1,2-dinitrobenzene (1.16 g, 72% yield); $^1$H-NMR (300 Mhz, CDCL$_3$): 7.84 (d, 1H, J=10.0 Hz), 7.19–7.36 (m, 5H), 7.00–7.06 (m, 2H), 4.10 (t, 2H, J=5.7 Hz), 2.73 (t, 2H, J=6.5 Hz), 1.89 (m, 4H).

(b) Ethyl 3-ethoxy-3-iminopropionate, prepared as in Example 2(a), was reacted with 2-(3,4-diaminobenzyl)isoindole-1,3-dione under conditions similar to that set forth in Example 2(b) to provide ethyl 5-(1,3-dioxo-1,3-dihydroisoindol-2-ylmethyl)-1H-benzoimidazol-2-ylacetate (71% yield); $^1$H-NMR (300 Mhz, DMSO-d$_6$): 7.78–7.9 (m, 4H), 7.43–7.47 (m, 2H), 7.12 (d, 1H, J=9.43 Hz), 4.82 (s, 2H), 4.07 (q, 2H, J=7.2 Hz), 3.44 (s, 2H), 1.38 (t, 3H, J=7.2 Hz).

(c) 4-(4-Phenylbutoxy)-1,2-dinitrobenzene was reduced under conditions similar to that set forth in Example 3(b) to provide 4-(4-phenylbutoxy)benzene-1,2-diamine (86% crude yield).

(d) A mixture of 5-(4-phenylbutoxy)benzene-1,2-diamine (0.06 g, 0.234 mmol) and ethyl 5-(1,3-dioxo-1,3-dihydroisoindol-2-ylmethyl)-1H-benzoimidazol-2-ylacetate (0.1 g, 0.234 mmol) was heated 1 hour at 185° C. under nitrogen. The mixture was suspended in diethyl ether, stirred vigorously for 1 hour. The solids were collected by filtration, washed with diethyl ether and dried to provide 2-{2-[5-(4-phenylbutoxy)-1H-benzoimidazol-2-ylmethyl]-3H-benzoimidazol-5-ylmethyl}isoindole-1,3-dione (0.1 g, 0.18 mmol).

(e) The 2-{2-[5-(4-phenylbutoxy)-1H-benzoimidazol-2-ylmethyl]-3H-benzoimidazol-5-ylmethyl}isoindole-1,3-dione was deprotected under conditions similar to that set forth in Example 2(g) to provide C-{2-[5-(4-phenylbutoxy)-1H-benzoimidazol-2-ylmethyl]-1H-benzoimidazol-5-yl}methylamine (0.05 g, 55% yield); $^1$H-NMR (300 Mhz, CD$_3$OD): 7.83 (d, 1H, J=8.6 Hz), 7.76 (s, 1H), 7.69 (d, 1H, J=10.0 Hz), 7.48 (d, 1H, J=8.6 Hz), 6.99–7.16 (m, 5H), 6.92 (d, 1H, J=10.0 Hz), 6.80 (t, 1H, J=7.2 Hz), 4,44 (s, 2H), 3.93 (t, 2H, J=6.5 Hz), 2.56 (t, 2H, J=7.2 Hz), 1.72 (m, 2H).

Example 5

2-Phenylethyl 2-(5-aminomethyl-1H-benzoimidazol-2-ylmethyl)-1H-benzoimidazole-5-carbamate trifluoroacetate (Compound 27)

2-[5-(1,3-Dioxo-1,3-dihydroisoindol-2-ylmethyl)-1H-benzoimidazol-2-ylmethyl]-1H-benzoimidazole-5-carboxylic acid (0.060 g, 0.133 mmol) in phenethanol (0.160 mL, 1.34 mmol) was combined with diphenylphosphoryl azide (0.034 mL, 0.158 mmol) and triethylamine (0.022 mL, 0.158 mmol) at room temperature under nitrogen. The mixture was stirred 1 hour at 120° C., cooled to room temperature and combined with ethanol (0.5 mL) and hydrazine (0.020 mL, 0.637 mmol). The mixture was stirred 45 minutes at 95° C., cooled to room temperature and diluted with with 3N hydrochloric acid (0.5 mL). The mixture was stirred 20 minutes at 55° C. and then filtered. The filtered solids were washed with 3N hydrochloric acid and the combined filtrates were washed with ethyl acetate (15 mL) and lyophilized. The residue was purified by preparative reverse phase HPLC to provide the desired product (0.008 g, 11% yield); $^1$H-NMR (300 Mhz, CD$_3$OD): 8.10 (s, 1H), 7.75 (s, 1H), 7.68 (d, 1H, J=9.3 Hz), 7.63 (d, 1H, J=9.3 Hz), 7.38–7.44 (m, 2H), 7.19–7.32 (m, 5H), 4.36 (t, 2H, J=6.8 Hz), 4.23 (s, 2H), 1.98 (t, 2H, J=6.8 Hz).

Example 6

2-(5-Guanidino-1H-benzoimidazol-2-ylmethyl)-N-(2-naphthalen-1-ylethyl)-3-methyl-3H-benzoimidazole-5-carboxyamide (Compound 28)

(a) A solution comprising 2-nitro-1,4-phenylenediamine (21.0 g, 137 mmol) in ethanol (350 mL) and 4.0M hydrogen chloride in dioxane (30.8 mL, 123 mmol) was stirred at room temperature for 15 minutes and then diethyl ether (1 L) was added to give a precipitate. The precipitate was collected by filtration, washed with additional diethyl ether and dried in vacuo to provide 2-nitro-1,4-phenylenediamine hydrochloride (23.3 g, 100% yield).

(b) A mixture comprising 2-nitro-1,4-phenylenediamine hydrochloride (15.0 g, 79.1 mmol) cyanamide (25.0 g, 595 mmol) and water (5 mL) was heated at 60° C. and stirred for 1.5 hours, allowed to cool to room temperature and then excess diethyl ether was slowly added to give a precipitate. The precipitate was collected by filteration, washed with additional diethyl ether and dried in vacuo to provide N-(4-amino-3-nitrophenyl)guanidine hydrochloride (18.0 g, 98% yield); $^1$H-NMR (300 MHz, DMSO-$d_6$): 9.7 (s), 7.8 (s), 7.6 (s), 7.5 (s), 7.3 (d), 7.1 (d).

(c) A mixture comprising N-(4-amino-3-nitrophenyl) guanidine hydrochloride (12.0 g, 51.8 mmol), 10% palladium on carbon (1.0 g), tetrahydrofuran (100 mL) and methanol (100 mL) was hydrogenated at one atmosphere, filtered and concentration in vacuo to provide N-(3,4-diaminophenyl)guanidine hydrochloride (10.3 g, 98% yield) as a dark solid; $^1$H-NMR (300 MHz, DMSO-$d_6$): 9.4 (s), 7.2 (s), 6.5 (d), 6.3 (s), 6.2 (d), 4.7 (s).

(d) A mixture comprising N-(3,4-diaminophenyl) guanidine hydrochloride (9.9 g, 49 mmol), ethoxycarbonimidoylacetic acid ethyl ester hydrochloride (12.4 g, 59 mmol) and acetic acid (20 mL) was heated in an oil bath at 110° C. and stirred for 1.5 hours, cooled to room temperature and concentrated in vacuo. The residue was dissolved in ethanol (15 mL) and then ethyl acetate (10 mL) was added to the solution to give a precipitate in suspension. The suspension was filtered and an excess of ethyl ether was added to the filtrate to give a second precipitate. The precipitate was collected by filtration, washed with additional ethyl ether and dried in vacuo to provide ethyl 5-guanidino-1H-benzoimidazol-2-ylacetate hydrochloride (14.1 g, 94% yield) as an off white solid; $^1$H-NMR (300 MHz, DMSO-$d_6$): 10.2 (s), 7.8 (d), 7.7 (m), 7.3 (d), 4.5 (s), 4.2 (q), 1.2 (t).

(e) A mixture comprising 4-nitro-3-methoxybenzoic acid (5.0 g, 25.4 mmol) and aqueous methylamine (40%, 15 mL) is a sealed tube was heated in an oil bath at 100° C. for 12 hours, allowed to cool to room temperature, and then poured into a stirring slurry of 1M aqueous hydrochloric acid and ice to give an orange precipitate. The precipitate was collected by filtration, rinsed with water and recrystallized from hot ethanol to provide 3-methylamino-4-nitrobenzoic acid as a bright red crystalline solid (3.6 g, 73% yield); $^1$H-NMR (300 MHz, DMSO-$d_6$): 13.5 (s), 8.3 (q), 8.2 (d), 7.4 (s), 7.1 (d), 3.0 (d).

(f) A mixture comprising 3-methylamino-4-nitrobenzoic acid (13.0 g, 66.3 mmol), PyBOP (38.0 g, 73.0 mmol), hydroxybenztriazole hydrate (9.9 g, 73.0 mmol), dimethylformamide (100 mL) and N-methylmorpholine (18.3 mL) was stirred at room temperature for 15 minutes and then 2-naphthylene-1-ylethylamine (13.8 g, 66.3 mmol) was added. The mixture was stirred for an additional 30 minutes and concentrated in vacuo. The residue was portioned between water and ethyl acetate and the organic layer was washed with water, 0.1M aqueous hydrochloric acid, saturated aqueous sodium hydrogencarbonate and then saturated aqueous sodium chloride, dried (magnesium sulfate), filtered and concentrated in vacuo. The residue was purified by recrystallization from hot ethanol to give 3-methylamino—N-(2-naphthalene-1-yl-ethyl)-4-nitrobenzamide as a bright red crystalline solid (21.3 g, 92% yield); $^1$H-NMR (300 MHz, DMSO-$d_6$): 8.8 (t), 8.3 (d), 8.2 (q), 8.1 (d), 7.9 (d), 7.8 (d), 7.6–7.3 (m), 7.2 (s), 7.0 (d), 3.6 (q), 3.3 (t), 3.0 (d).

(g) A mixture comprising 3-methylamino—N-(2-naphth-1-ylethyl)-4-nitrobenzamide (21.3 g, 61 mmol), 10% palladium on carbon (1.0 g), tetrahydrofuran (100 mL) and methanol (100 mL) was hydrogenated at one atmosphere, filtered and concentration in vacuo to provide 4-amino-3-methylamino-N-(2-naphth-1-ylethyl)-4-benzamide (18.4 g, 95% yield) as a discolored amorphous solid; 1H-NMR (300 MHz, DMSO-$d_6$): 8.3 (d), 8.2 (t), 7.9 (d), 7.8 (d), 7.6–7.4 (m), 7.1 (d), 6.9 (s), 6.5 (d), 5.0 (s), 3.5 (q), 3.2 (t), 2.7 (s).

(h) A mixture comprising ethyl 5-guanidino-1H-benzoimidazol-2-ylacetate hydrochloride (0.5 g, 1.7 mmol), 4-amino-3-methylamino-N-(2-naphth-1-ylethyl)-4-benzamide (0.5 g, 1.7 mmol) and dimethylformamide (2 mL) heated in an oil bath at 185° C. and stirred under a nitrogen atmosphere for 3.5 hours, cooled to room temperature and poured into stirring acetonitrile (150 mL) to give a precipitate. The precipitate was washed with additional acetonitrile and diethyl ether ( 150 mL), collected by filtration and dried in vacuo to give an off white solid. The solid was purified by preparative reverse phase HPLC to provide of 2-(5-guanidino-1H-benzoimidazol-2-ylmethyl)-N-(2-naphth-1-ylethyl)-3-methyl-3H-benzoimidazole-5-carboxamide as a white solid (0.5 g, 57%); LRMS(ESI): Calculated for $C_{30}H_{28}N_8O$: 516.6; Found (MH$^+$): 517.2.

Example 7

Ethyl 2-(4-{2-[1-(5-guanidino-1H-benzoimidazol-2-yl)ethyl]-1,4,6,7-tetrahydroimidazo[4,5-c]pyridin-5-yl}-4-oxobutyl)benzoate (Compound 29)

(a) A solution comprising ethyl 2-cyanopropionate (100 g, 0.29 mol.) in ethanol (65 mL) was cooled to 0° C. and then saturated with dry hydrogen chloride gas. The mixture was allowed to warm to room temperature, stirred for 24 hours, cooled to 0° C. and saturated with hydrogen chloride gas. The mixture was allowed to warm to room temperature and stirred another 24 hours. Ethyl ether:hexane (1:1), was added to the mixture to give a precipitate. The precipitate was isolated by filtration and dried in vacuo to provide ethyl 2-(N-ethoxyamidino)propionate hydrochloride (119.6 g, 73% yield) as a white solid; $^1$H NMR (300 MHz, DMSO-$d_6$): 12.05 (br s, 2H), 4.50 (q, 2H), 4.15 (m, 3H), 1.30 (m, 6H), 1.20 (tr, 3H).

(b) A mixture comprising 3,4-diaminopyridine (51.7 g, 0.46 mol), ethyl 2-(N-ethoxyamidino)propionate hydrochloride (125 g, 0.69 mol) and glacial acetic acid (200 mL) was heated at 85° C. and stirred for 18 hours and then heated at 120° C. and stirred for an additional hour. The mixture was cooled to room temperature and concentrated in vacuo. The residue was neutralized by addition of an excess of 5M aqueous ammonium hydroxide and the mixture was extracted with ethyl acetate. The organic layer was washed with saturated aqueous sodium hydrogen carbonate and then saturated aqueous sodium chloride, dried (MgSO$_4$), filtered and concentrated in vacuo to provide ethyl 1H-imidazo[4, 5-c]pyridine-2-carboxylate (60.4 g, 58% yield); $^1$H NMR (300 MHz, CDCl$_3$): 9.00 (s, 1H), 8.45 (d, 1H), 7.50 (d, 1H), 4.25 (q, 2H), 3.90 (q, 1H), 1.75 (d, 3H), 1.25 (tr, 3H).

(c) A mixture comprising ethyl 1H-imidazo[4,5-c] pyridine-2-carboxylate (34.7 g, 158 mmol), trifluoroacetic acid (50 mL) and platinum oxide (2.5 g) in a Parr hydrogenation apparatus was hydrogenated at 50 psi for 24 hours, filtered and concentrated in vacuo. The oily residue was dissolved in a minimum of ethanol and dry hydrogen chloride in dioxane solution (4M, 120 mL, 475 mmol) was added to the solution. An excess of ethyl ether was added to the solution to give a precipitate. The precipitate was collected by filtration and dried in vacuo to provide ethyl 1,4,6,7-tetrahydro-1H-imidazo[4,5-c]pyridine-2-carboxylate dihydrochloride (30.7 g, 66% yield); $^1$H NMR (300 MHz, DMSO-$d_6$): 10.00 (br s, 2H), 4.35 (q, 1H), 4.20 (br s, 2H), 4.10 (m, 2H), 3.35 (m, 2H), 2.90 (br s, 2H), 1.55 (d, 3H), 1.15 (tr, 3H).

(d) A mixture comprising ethyl 1,4,6,7-tetrahydro-1H-imidazo[4,5-c]pyridine-2-carboxylate dihydrochloride (60.2 g, 0.20 mol), acetonitrile (500 mL) and diisopropylethylamine (100 mL, 0.60 mol) was cooled to 0° C. and stirred while benzylchloroformate (58 mL, 0.40 mol) was added slowly. The mixture was slowly warmed to room temperature, stirred an additional 16 hours and concentrated in vacuo. The residue was dissolved in ethyl ether (500 mL) and the solution was washed with 0.1M aqueous hydrochloric acid, saturated aqueous sodium hydrogencarbonate and saturated aqueous sodium chloride, dried over anhydrous sodium sulfate, filtered and concentrated in vacuo to provide a colorless oil. The residue was dissolved in ethanol (320 mL) and the solution was cooled to 0° C. and then sodium ethoxide in ethanol solution (2.6M, 85 mL, 0.22 mol.) was slowly added. The mixture was stirred for one hour at 0° C. and then hydrogen chloride solution in dioxane (4M, 50 mL) was added. The mixture was concentrated in vacuo and the residue was dissolved in ethyl acetate (250 mL) and saturated aqueous sodium hydrogen carbonate. The organic layer was separated and washed with saturated aqueous sodium chloride, dried over anhydrous sodium sulfate, filtered and concentrated in vacuo to provide 5-benzyl 2-ethyl 1,4,6,7-tetrahydroimidazo[4,5-]pyridine-2,5-dicarboxylate as a yellow amorphous material (52 g, 72% yield); $^1$H NMR (300 MHz, DMSO-d6): 11.75 (br s, 1H), 7.30 (s, 5H), 5.10 (s, 2H), 4.40 (br s, 2H), 4.05 (m, 2H), 3.75 (q, 1H), 3.65 (br s, 2H), 1.40 (d, 3H), 1.15 (tr, 3H).

(e) A mixture comprising 4-chlorobutyryl chloride (12.6 g, 89.2 mmol), tert-butanol (25 mL), pyridine (6.9 g, 86.5 mmol) and 4-dimethylaminopyridine (1.0 g, 8.2 mmol) was heated at 50° C. under an atmosphere of dry nitrogen for 12 hours to give a white suspension. The suspension was partitioned between ethyl ether (250 mL) and water and the organic layer was separated and washed repeatedly with water then 0.1M aqueous hydrochloric acid, saturated aqueous sodium carbonate and saturated aqueous sodium chloride, dried over anhydrous magnesium sulfate, filtered and concentrated in vacuo to a colorless oil. The oil was distilled at 0.5 mmHg (51° C.) to provide tert-butyl 4-chlorobutyrate as a colorless liquid (11.27 g, 73% yield); $^1$H NMR (300 MHz, CDCl$_3$): 3.60 (tr, 2H), 2.40 (tr, 2H), 2.10 (m, 2H), 1.45 (s, 9H).

(f) A mixture comprising ethyl salicylate (3.14 g, 18.9 mmol) and cesium carbonate (6.2 g, 18.9 mmol), dimethylformamide (25 mL) and tert-butyl 4-chlorobutyrate (4.08 g, 22.8 mmol) was heated at 70° C. and stirred for 12 hours. The mixture was partitioned between ethyl ether (100 mL) and water and the organic layer was separated and washed with additional water (3x) and saturated aqueous sodium chloride, dried over anhydrous magnesium sulfate, filtered and concentrated in vacuo to afford a colorless oil. The residue was purified by silica gel flash chromatography using pure hexane to (10:1) hexane:ethyl acetate to provide ethyl 2-(3-tert-butoxycarbonylpropoxy)benzoate (3.6 g, 62% yield) as a colorless oil; $^1$H NMR (300 MHz, CDCl$_3$): 7.80 (d, 1H), 7.49 (tr, 1H), 7.00 (m, 2H), 4.40 (q, 2H), 4.10 (tr, 2H), 2.50 (tr, 2H), 2.10 (m, 2H), 1.45 (s, 9H), 1.40 (tr, 3H).

(g) Ethyl 2-(3-tert-butoxycarbonylpropoxy)benzoate (3.60 g, 11.7 mmol) was treated with an excess of trifluoroacetic acid at room temperature over one hour. The solution was concentrated in vacuo and the oily residue purified by silica gel flash chromatography using (10:1) hexane:ethyl acetate to pure ethyl ether to provide 4-(2-ethoxycarbonylphenoxy)butyric acid as a colorless crystalline solid (2.81 g, 95% yield); $^1$H NMR (300 MHz, CDCl$_3$): 7.80 (d, 1H), 7.50 (tr, 1H), 7.00 (m, 2H), 4.40 (q, 2H), 4.15 (tr, 2H), 2.65 (tr, 2H), 2.20 (m, 2H), 1.40 (tr, 3H).

(h) A mixture comprising benzyl 2-ethoxycarbonylmethyl-1,4,6,7-tetrahydroimidazo[4,5-c]pyridine-5-carboxylate (1.7 g, 4.8 mmol), N-(3,4-diaminophenyl)guanidine hydrochloride (0.8 g, 4.0 mmol) and dimethylformamide (2 mL) heated in an oil bath at 185° C. and stirred under a nitrogen atmosphere for 2.5 hours. The mixture was cooled to room temperature and poured into stirring acetonitrile (150 mL) to give a precipitate. The precipitate was washed with additional acetonitrile and diethyl ether (150 mL), collected by filtration and dried in vacuo to give an off white solid. The solid was purified by preparative reverse phase HPLC to provide benzyl 2-[1-(5-guanidino-1H-benzoimidazol-2-yl)ethyl]-1,4,6,7-tetrahydroimidazo[4,5-c]pyridine-5-carboxylate as a white solid (1.0 g, 55% yield); LRMS(ESI): Calculated for $C_{24}H_{26}N8O_2$: 458.5; Found (MH$^+$): 459.2.

(i) A mixture comprising benzyl 2-[1-(5-guanidino-1H-benzoimidazol-2-yl)ethyl]-1,4,6,7-tetrahydroimidazo[4,5-c]pyridine-5-carboxylate (1.0 g, 2.2 mmol), 10% palladium on carbon (0.5 g), tetrahydrofuran (50 mL) and methanol (50 mL) was hydrogenated at one atmosphere, filtered and concentrated in vacuo to provide N-{2-[1-(4,5,6,7-tetrahydroimidazo[4,5-c]pyridine-2-yl)ethyl]-1H-benzoimidazol-5-yl)-guanidine (0.69 g, 97% yield); LRMS (ESI): Calculated for $C_{16}H_{20}N_8$: 324.4; Found (MH$^+$): 325.2.

(j) A mixture comprising 4-(2-ethoxycarbonylphenoxy)butyric acid (155 mg, 0.61 mmol), PyBOP (360 mg, 0.69 mmol), hydroxybenztriazole hydrate (87 mg, 0.64 mmol), N-methylmorpholine (0.16 mL, 0.92 mmol) and dimethylformamide (2.5 mL) was stirred at room temperature for 10 minutes and then N-{2-[1-(4,5,6,7-tetrahydroimidazo[4,5-c]pyridin-2-yl)ethyl]-3H-benzimidazol-5-yl }guanidine (203 mg, 0.63 mmol) was added. The mixture was stirred for 3 hours at room temperature and concentrated in vacuo. The residue was dissolved in 5% aqueous acetonitrile and the product purified by preparative reverse phase HPLC. The combined pure fractions were then lyophillized to provide ethyl 2-(4-{2-[1-(5-guanidino-1H-benzoimidazol-2-yl)ethyl]-1,4,6,7-tetrahydroimidazo[4,5-c]pyridin-5-yl}-4-oxobutyl)benzoate; LRMS (BioIon): calculated for $C_{29}H_{34}N_8O_4$: 558.6; Found: 559.3.

Example 8

2-[1-(5-Hydroxy-1H-benzoimidazol-2-yl)ethyl]-N-[2-(2-methoxyphenoxy)ethyl]-3-methyl-3H-benzoimidazole-5-carboxamide (Compound 30)

(a) A solution of tert-butyl 2-hydroxyethylcarbamate (25 mL, 161.6 mmol) in dichloromethane (60 mL) was cooled to 0° C. and stirred while first diisopropylethylamine (33.8 mL, 193.9 mmol) was added and then mesyl chloride (13.7 mL, 177.8 mmol) then was added dropwise. The mixture was allowed to warm to 23° C., stirred for 18 hours, poured into dichloromethane (200 mL) and washed with aqueous hydrochloric acid (3M, 3×25 mL) and saturated aqueous sodium hydrogencarbonate (2×25 mL). The organic layer was separated, dried (MgSO$_4$) and concentrated in vacuo to provide tert-butyl 2-methylsulfonyloxyethylcarbamate (37.39 g, 97% yield) as a brown oil; MS (PB-PCI) C$_8$H$_{17}$NO$_5$S m/e calc 239.08; found 240 (MH$^+$).

(b) Lithium bromide (136 g, 1.56 mol.) was dissolved in tetrahydrofuran (600 mL) at 0° C. The mixture was allowed to warm to 23° C. and then tert-butyl 2-methylsulfonyloxyethylcarbamate (37.39 g, 156 mmol) was added dropwise. The mixture was stirred at 23° C. for 18 hours and concentrated in vacuo. The residue was dissolved in hexanes and the organic layer was washed with water and brine, dried (Na$_2$SO$_4$) and concentrated in vacuo to provide tert-butyl 2-bromoethylcarbamate (33.48 g, 96% yield) as a brown oil; MS (PB-PCI) C$_7$H$_{14}$BrNO$_2$ m/e calc 224.10; found 225 (MH$^+$).

(c) A mixture of 2-methoxyphenol (9.8 mL, 89.3 mmol), dimethylformamide (100 mL) and potassium carbonate (61.5 g, 445 mmol) was stirred at 23° C. while as tert-butyl 2-bromoethylcarbamate (20 g, 89.3 mmol) was added. The mixture was stirred for 24 hours and then poured into ethyl ether:hexanes (1:1, 400 mL) and was washed with water (5×50 mL). The aqueous layer was extracted with ethyl ether:hexanes (1:1, 3×40 mL) and the combined organic layers were dried (Na$_2$SO$_4$) and concentrated in vacuo to provide tert-butyl 2-(2-methoxyphenoxy)ethylcarbamate (23.22 g, 97% yield) as a yellow oil; MS (PB-PCI) C$_{14}$H$_{21}$NO$_4$ m/e calc 267.32; found 268 (MH$^+$).

(d) tert-Butyl 2-(2-methoxyphenoxy)ethylcarbamate (23.8 g, 89 mmol) was cooled to 0° C. and stirred as a mixture of trifluoroacetic acid:dichloromethane (1:1, 40 mL) was added dropwise. The mixture was allow to warm to 23° C., stirred for 2 hours and concentrated in vacuo. The residue was taken back up in dichloromethane (100 mL) and the solution was washed with saturated aqueous sodium hydrogen carbonate (3×20 mL) and sodium hydroxide (10%, 3×20 mL), dried (Na$_2$SO$_4$), filtered and concentrated in vacuo to provide 2-(2-methoxyphenoxy)ethylamine (13 g, 88% yield) a light yellow solid; MS (PB-PCI) C$_9$H$_{13}$NO$_2$ m/e calc 167.21; found 168 (MH$^+$).

(e) A heterogeneous mixture comprising 3-methoxy-4-nitrobenzoic acid (15.42 g, 78.2 mmol) and thionyl chloride (70 mL, 391 mmol) was heated at reflux for one hour. The excess thionyl chloride was removed by distillation and the residue was concentrated in vacuo to provide 3-methoxy-4-nitrobenzoyl chloride (16.8 g, 99% yield) as a light yellow solid; MS (PB-PCI) C$_8$H$_6$ClNO$_4$ m/e calc 215.59; found 216 (MH$^+$).

(f) A mixture comprising 2-(2-methoxyphenoxy)ethylamine (10 g, 59.9 mmol), diisopropylethylamine (13.9 mL, 81.6 mmol) and dichloromethane (80 mL) was cooled to 0° C. and then a solution of 3-methoxy-4-nitrobenzoyl chloride (11.76 g, 54.4 mmol) in dichloromethane (50 mL) was added dropwise. The mixture was allowed to warm to 23° C. over two hours, quenched with aqueous hydrochloric acid (3M, 20 mL), washed with water (3×20 mL), dried (Na$_2$SO$_4$) and concentrated in vacuo to provide N-[2-(2-methoxyphenoxy)ethyl]-3-methoxy-4-nitrobenzamide (14 g, 74% yield) an off white solid; MS (PB-PCI) C$_{17}$H$_{18}$N$_2$O$_6$ m/e calc 346.34; found 347 (MH$^+$).

(g) A mixture comprising N-[2-(2-methoxyphenoxy)ethyl]-3-methoxy-4-nitrobenzamide (4.0 g, 11.6 mmol), aqueous methylamine (40%, 10 mL) and DMSO (2 mL) in a sealed tube was heated at 110° C. for 4 hours, cooled and then poured into water (25 mL). The dilution was treated with 3M aqueous hydrochloric acid to give an orange solid. The solid was isolated by filtration to provide N-[2-(2-methoxyphenoxy)ethyl]-3-methylamino-4-nitrobenzamide (3.56 g, 89% yield); MS (PB-PCI) C$_{17}$H$_{19}$N$_3$O$_5$ m/e calc 345.35; found 346 (MH$^+$).

(h) A mixture comprising N-[2-(2-methoxyphenoxy)ethyl]-3-methylamino-4-nitrobenzamide (3.56 g, 10.3 mmol), suspended palladium on carbon (10%, 0.5 g) in methanol (100 mL) and tetrahydrofuran (50 mL) was stirred under a hydrogen atmosphere at ambient pressure for 2.5 hours. The mixture was filtered and the solution concentrated in vacuo to provide 4-amino-N-[2-(2-methoxyphenoxy)ethyl]-3-methylaminobenzamide (3.37 g, 100% yield) as a green foam; MS (PB-PCI) C$_{17}$H21N$_3$O$_3$ m/e calc 315.37; found 316 (MH$^+$).

(i) A mixture comprising 4-amino-3-nitrophenol (5.0 g, 32.4 mmol), palladium on carbon (10%, 1.0 g) and methanol (50 mL) in a Parr apparatus was hydrogenated at 50 psi for 3 hours, filtered through celite and concentrated in vacuo to provide 3,4-diaminophenol (4.02 g, 91% yield) as a dark solid; MS (PB-PCI) C$_6$H$_8$N$_2$O m/e calc 124.16; found 125 (MH$^+$).

(j) A mixture comprising of 3,4-diaminophenol (3.661 g, 29.5 mL), ethyl 2-(N-ethoxyamidino)propionate (7.423 g, 38.4 mmol) and ethanol (30 mL) was heated at reflux for 6 hours and concentrated in vacuo. The residue was dissolved in ethyl acetate (200 mL) and the solution was washed with saturated aqueous sodium hydrogencarbonate (3×20 mL) and brine (1×20 mL), dried (MgSO$_4$) and concentrated in vacuo to provide ethyl 2-(5-hydroxy-1H-benzoimidazol-2-yl)propionate (6.3 g, 91% yield) as a dark solid. The solid was further purified by silica gel flash chromatography (100% ethyl acetate); MS (PB-PCI) C$_{12}$H$_{14}$N$_2$O$_3$ m/e calc 234.28; found 235 (MH$^+$).

(k) A mixture comprising ethyl 2-(5-hydroxy-1H-benzoimidazol-2-yl)propionate (148 mg, 0.63 mmol), 4-amino-N-[2-(2-methoxyphenoxy)ethyl]-3-methylaminobenzamide (200 mg, 0.63 mmol) and 1,3-dimethyl-3,4,5,6-tetrahydro-2(1H)-pyrimidone (0.5 mL) was stirred at room temperature until homogeneous, degassed under vacuum and concentrated by heating at 170° C. for 2 hours under a stream of N$_2$. The residue was cooled to room temperature and rinsed with an excess of ethyl ether. The resulting amorphous material was taken up in 50% aqueous acetonitrile and purified by preparative reverse phase HPLC (2–50% CH$_3$CN/H$_2$O) to provide 2-[1-(5-hydroxy-1H-benzoimidazol-2-yl)ethyl]-N-[2-(2-methoxyphenoxy)ethyl]-3-methyl-3H-benzoimidazole-5-carboxamide (40 mg, 13% yield) as a light pink solid; MS (BioIon) C$_{27}$H$_{27}$N$_5$O$_4$ m/e calc 485.59; found 486.5 (MH$^+$).

Proceeding as in Example 8 the following compounds of the invention were prepared:

methyl 2-(2-{2-[1-(5-fluoro-1H-benzoimidazol-2-yl)ethyl]-3-methyl-3H-benzoimidazol-5-ylcarbonylamino}ethoxy)benzoate (Compound 31), MS (BioIon) C$_{28}$H$_{26}$N$_5$O$_4$F m/e calc 515.54; found 516 (MH$^+$);

2-(2-{2-[1-(5-fluoro-1H-benzoimidazol-2-yl)ethyl]-3-methyl-3H-benzoimidazol-5-ylcarbonylamino}ethoxy)benzoic acid (Compound 32) MS (BioIon) C$_{27}$H$_{24}$N$_5$O$_4$F m/e calc 501.52; found 502.1 (MH$^+$);

ethyl 2-(2-{2-[1-(5-hydroxy-1H-benzoimidazol-2-yl)ethyl]-3-methyl-3H-benzoimazol-5-ylcarbonylamino}ethoxy)benzoate (Compound 33), MS (BioIon) $C_{29}H_{29}N_5O_5$ m/e calc 527.58; found 528.1 (MH$^+$);

2-(2-{2-[1-(5-hydroxy-1H-benzoimidazol-2-yl)ethyl]-3-methyl-3H-benzoimazol-5-ylcarbonylaminoethoxy)benzoic acid (Compound 34), MS (BioIon) $C_{27}H_{25}N_5O_5$ m/e calc 499.53; found 500.1 (MH$^+$);

N-ethyl-2-[1-(5-hydroxy-1H-benzoimidazol-2-yl)ethyl]-3-methyl-3H-benzoimidazole-5-carboxamide (Compound 35), MS (BioIon) $C_{20}H_{21}N_5O_2$ m/e calc 363.42; found 364.1 (MH$^+$);

2-[1-(5-hydroxy-1H-benzoimidazol-2-yl)ethyl]-N-(2-methoxyethyl)-3-methyl-3H-benzoimidazole-5-carboxamide (Compound 36), MS (BioIon) $C_{21}H_{23}N_5O_3$ m/e calc 393.45; found 394.1 (MH$^+$);

butyl 2-(2-{2-[l-(5-hydroxy-1H-benzoimidazol-2-yl)ethyl]-3-methyl-3H-benzoimidazol-5-ylcarbonylamino}ethoxy)benzoate (Compound 37), MS (BioIon) $C_{31}H_{33}N_5O_5$ m/e calc 555.64; found 555.7 (MH$^+$);

3-{2-[1-(5-guanidino-1H-benzoimidazole-2-yl)ethyl]-6-[2-(2-methoxyphenoxy)ethylcarbamoyl]benzimidazol-1-yl}propane-1-sulfonic acid (Compound 38), MS (LCMS) $C_{30}H_{35}N_8O_6S$ m/e calc 635.72; found 635.4 (MH$^+$);

N-[2-(2-ethoxyphenoxy)ethyl]-2-[1-(5-hydroxy-1H-benzoimidazol-2-yl)ethyl]-3-methyl-3H-benzoimidazole-5-carboxamide (Compound 39), MS (BioIon) $C_{28}H_{29}N_5O_4$ m/e calc 499.58; found 500.4 (MH$^+$);

2-[1-(5-hydroxy-1H-benzoimidazol-2-yl)ethyl]-N-[2-(2-isopropoxyphenoxy)ethyl]-3-methyl-3H-benzoimidazole-5-carboxamide (Compound 40), MS (BioIon) $C_{29}H_{31}N_5O_4$ m/e calc 513.61; found 514.5 (MH$^+$);

102-[1-(5-hydroxy-1H-benzoimidazol-2-yl)ethyl]-3-methyl-N-[2-(2-propoxyphenoxy)ethyl]-3H-benzoimidazole-5-carboxamide (Compound 41), MS (BioIon) $C_{29}H_{31}N_5O_4$ m/e calc 513.61; found 514.2 (MH$^+$);

propyl 2-(2-{2-[1-(5-hydroxy-1H-benzoimidazol-2-yl)ethyl]-3-methyl-3H-benzoimidazol-5-ylcarbonylamino}ethoxy)benzoate (Compound 42), MS (ESI) $C_{30}H_{31}N_5O_5$ m/e calc 541.61; found 542.2 (MH$^+$);

isobutyl 2-(2-{2-[1-(5-hydroxy-1H-benzoimidazol-2-yl)ethyl]-3-methyl-3H-benzoimidazol-5-ylcarbonylamino}ethoxy)benzoate (Compound 43), MS (BioIon) $C_{31}H_{33}N_5O_5$ m/e calc 555.64; found 556.3 (MH$^+$);

ethyl 4-{2-[1-(5-hydroxy-1H-benzoimidazol-2-yl)ethyl]-3-methyl-3H-benzoimidazol-5-ylcarbonylaminobutyrate (Compound 44), MS (BioIon) $C_{24}H_{27}N_5O_4$ m/e calc 449.51; found 449.9 (MH$^+$);

4-{2-[1-(5-hydroxy-1H-benzoimidazol-2-yl)ethyl]-3-methyl-3H-benzoimidazol-5-ylcarbonylamino}butyric acid (Compound 45), MS (BioIon) $C_{22}H_{23}N_5O_4$ m/e calc 421.46; found 422.1 (MH$^+$);

isopropyl 2-(2-{2-[1-(5-hydroxy-1H-benzoimidazol-2-yl)ethyl]-3-methyl-3H-benzoimidazol-5-ylcarbonylamino}ethoxy)benzoate (Compound 46), MS (ESI) $C_{30}H_{31}N_5O_5$ m/e calc 541.61; found 542.2 (MH$^+$);

N-{2-[2-(1-ethylpropoxy)phenoxy]ethyl}-2-[1-(5-hydroxy-1H-benzoimidazol-2-yl)ethyl]-3-methyl-3H-benzoimidazole-5-carboxamide (Compound 47), MS (BioIon) $C_{31}H_{35}N_5O_4$ m/e calc 541.65; found 542.5 (MH$^+$);

ethyl 2-(2-{2-[1-(5-fluoro-1H-benzoimidazol-2-yl)ethyl]-3-methyl-3H-benzoimidazol-5-ylcarbonylamino}ethoxy)benzoate (Compound 48), MS (BioIon) $C_{29}H_{28}N_5O_4F$ m/e calc 529.57; found 529.5 (MH$^+$);

2-methoxyethyl 2-(2-{2-[1-(5-hydroxy-1H-benzoimidazol-2-yl)ethyl]-3-methyl-3H-benzoimidazol-5-ylcarbonylamino}ethoxy)benzoate (Compound 49), MS (BioIon) $C_{30}H_{31}N_5O_6$ m/e calc 557.61; found 58.2 (MH$^+$);

N-(3-methoxypropyl)-2-[1-(5-hydroxy-1H-benzoimidazol-2-yl)ethyl]-3-methyl-3H-benzoimidazole-5-carboxamide (Compound 50), MS (BioIon) $C_{22}H_{25}N_5O_3$ m/e calc 407.47; found 408.0 (MH$^+$);

2-[1-(5-hydroxy-1H-benzoimidazol-2-yl)ethyl]-N-[2-(2-methoxymethylphenoxy)ethyl]-3-methyl-3H-benzoimidazole-5-carboxamide (Compound 51), MS (BioIon) $C_{28}H_{29}N_5O_4$ m/e calc 499.57; found 499.8 (MH$^+$);

N-[2-(2-ethoxymethylphenoxy)ethyl]-2-[1-(5-hydroxy-1H-benzoimidazol-2-yl)ethyl]-3-methyl-3H-benzoimidazole-5-carboxamide (Compound 52), MS (BioIon) $C_{29}H_{31}N_5O_4$ m/e calc 513.60; found 514.1 (MH$^+$);

ethyl 2-(2-{2-[1-(6-fluoro-5-hydroxy-1H-benzoimidazol-2-yl)ethyl]-3-methyl-3H-benzoimidazol-5-ylcarbonylamino}ethoxy)benzoate (Compound 53), MS (ESI) $C_{29}H_{28}N_5O_5F$ m/e calc 545.57; found 546.3 (MH$^+$);

ethyl 2-(2-{2-[1-(5-hydroxy-1H-benzoimidazol-2-yl)ethyl]-3-methyl-3H-benzoimidazol-5-ylcarbonylamino}ethoxy)cyclohexanecarboxyate (Compound 54), MS (BioIon) $C_{29}H_{35}N_5O_5$ m/e calc 533.63; found 534 (MH$^+$);

2-[1-(5-hydroxy-1H-benzoimidazol-2-yl)ethyl]-3-methyl-N-[2-(2-propoxymethylphenoxy)ethyl]-3H-benzoimidazole-5-carboxamide (Compound 55), MS (BioIon) $C_{30}H_{33}N_5O_4$ m/e calc 527.62; found 527.6 (MH$^+$);

2-[1-(5-hydroxy-1H-benzoimidazol-2-yl)ethyl]-N-[2-(2-isopropoxymethylphenoxy)ethyl]-3-methyl-3H-benzoimidazole-5-carboxamide (Compound 56), MS (BioIon) $C_{30}H_{33}N_5O_4$ m/e calc 527.62; found 527.9 (MH$^+$);

2-[1-(5-hydroxy-1H-benzoimidazol-2-yl)ethyl]-N-{2-[2-(2-methoxyethoxymethyl)phenoxy]ethyl}-3-methyl-3H-benzoimidazole-5-carboxamide, (Compound 57), MS (BioIon) $C_{30}H_{33}N_5O_5$ m/e calc 543.62; found 543.4 (MH$^+$);

2-[1-(1H-benzoimidazol-2-yl)ethyl]-N-[2-(2-methoxymethylphenoxy)ethyl]-3-methyl-3H-benzoimidazole-5-carboxamide (Compound 58), MS (BioIon) $C_{28}H_{29}N_5O_3$ m/e calc 483.57; found 484 (MH$^+$);

N-[2-(2-ethoxymethylphenoxy)ethyl]-2-[1-(1H-benzoimidazol-2-yl)ethyl]-3-methyl-3H-benzoimidazole-5-carboxamide (Compound 59), MS (BioIon) $C_{29}H_{31}N_5O_3$ m/e calc 497.6; found 498.3 (MH$^+$);

2-[1-(1H-benzoimidazol-2-yl)ethyl]-3-methyl-N-[2-(2-propoxymethylphenoxy)ethyl]-3H-benzoimidazole-5-carboxamide (Compound 60), MS (BioIon) $C_{31}H_{33}N_5O_3$ m/e calc 511.62; found 511.5 (MH$^+$);

2-[1-(1H-benzoimidazol-2-yl) ethyl]-N-[2-(2-isopropoxymethylphenoxy) ethyl]-3-methyl-3H-benzoimidazole-5-carboxamide (Compound 61), MS (BioIon) $C_{30}H_{33}N_5O_3$ m/e calc 511.62; found 511.6 (MH$^+$);

2-[1-(1H-benzoimidazol-2-yl)ethyl]-N-{2-[2-(2-methoxyethoxymethyl)phenoxy]ethyl}-3-methyl-3H-benzoimidazole-5-carboxamide (Compound 62), MS (BioIon) $C_{31}H_{33}N_5O_4$ m/e calc 527.62; found 527.7 (MH$^+$);

2-[1-(5-hydroxy-1H-benzoimidazol-2-yl)ethyl]-3-methyl-N-[2-(2-morpholin-4-ylphenoxy)ethyl]-3H-benzoimidazole-5-carboxamide (Compound 63), MS (BioIon) $C_{30}H_{32}N_6O_4$ m/e calc 540.73; found 541.8 (MH$^+$);

N-(2-phenylsulfonylethyl)-2-[1-(5-hydroxy-1H-benzoimidazol-2-yl)ethyl]-3-methyl-3H-benzoimidazole-5-carboxamide (Compound 64), MS (BioIon) $C_{26}H_{25}N_5O_4S$ m/e calc 503.59; found 504.2 (MH$^+$);

2-(2-{2-[1-(6-fluoro-5-hydroxy-1H-benzoimidazol-2-yl)ethyl]-3-methyl-3H-benzoimidazol-5-ylcarbonylamino}ethoxy]benzoic acid (Compound 65), MS (ESI) $C_{27}H_{24}N_5O_5F$ m/e calc 517.52; found 518.2 (MH$^+$);

ethyl 2-hydroxy-5-{2-[1-(5-hydroxy-1H-benzoimidazol-2-yl)ethyl]-3-methyl-3H-benzoimidazol-5-ylcarbonylamino}benzoate (Compound 66), MS (BioIon) $C_{27}H_{25}N_5O_5$ m/e calc 499.52; found 500.2 (MH$^+$);

2-[1-(5-fluoro-1H-benzoimidazol-2-yl)ethyl]-3-methyl-N-[2-(2-morpholin-4-ylphenoxy)ethyl]-3H-benzoimidazole-5-carboxamide (Compound 67), MS (BioIon) $C_{30}H_{31}N_6O_3F$ m/e calc 542.62; found 543.4 (MH$^+$);

N-(2-phenylsulfonylethyl)-2-[1-(5-fluoro-1H-benzoimidazol-2-yl)ethyl]-3-methyl-3H-benzoimidazole-5-carboxamide (Compound 68), MS (BioIon) $C_{26}H_{24}N_5O_3FS$ m/e calc 505.58; found 506.5 (MH$^+$);

ethyl 2-(-2-{2-[1-(4,6-difluoro-5-hydroxy-1H-benzoimidazol-2-yl)ethyl]-3-methyl-3H-benzoimidazol-5-ylcarbonylamino}ethoxy)benzoate (Compound 69), MS (BioIon) $C_{29}H_{27}N_5O_5F_2$ m/e calc 563.52; found 563.4 (MH$^+$);

2-(2-{2-[1-(4,6-difluoro-5-hydroxy-1H-benzoimidazol-2-yl)ethyl]-3-methyl-3H-benzoimidazol-5-ylcarbonylamino}ethoxy)benzoic acid (Compound 70), MS (BioIon) $C_{27}H_{23}N_5O_5F_2$ m/e calc 536.51; found 563 (MH$^+$);

ethyl 2-(-2-{2-[1-(4,6-difluoro-5-imidazol-1-yl-1H-benzoimidazol-2-yl)ethyl]-3-methyl-3H-benzoimidazol-5-ylcarbonylamino}ethoxy)benzoate (Compound 71), MS (BioIon) $C_{32}H_{29}N_7O_4F_2$ m/e calc 613.62; found 614.3 (MH$^+$);

2-[1-(5-guanidino-1H-benzoimidazol-2-yl)ethyl]-3-methyl-N-{2-[2-(3-methyl-[1,2,4]oxadiazol-5-yl)phenoxy]ethyl}-3H-benzoimidazole-5-carboxamide (Compound 72), MS (BioIon) $C_{30}H_{30}N_{10}O_3$ m/e calc 578.63; found 579.4 (MH$^+$); and 2-[1-(5-imidazol-1-yl-1H-benzoimidazol-2-yl)ethyl]-3-methyl-N-{2-[2-(3-methyl[1,2,4]oxadiazol-5-yl)phenoxy]ethyl}-3H-benzoimidazole-5-carboxamide (Compound 73), MS (BioIon) $C_{32}H_{29}N_9O_3$ m/e calc 587.64; found 588.2 (MH$^+$).

Example 9

2-[2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)ethoxy]benzoic acid (Compound 74)

(a) A solution comprising 3,4-diaminopyridine ((51.7 g, 0.46 mol) in acetic acid (400 mL) was heated to 85° C. and then diethyl methyl-1-iminomalonate (125 g, 0.60 mol) was added in 3 equivalent portions over 6 hours. The mixture was heated at 85° C. for 12 hours and at 120° C. for another hour, cooled and concentrated under reduced pressure. The residue was cooled to 0° C. and neutralized with 5 N ammonium hydroxide. The aqueous layer was extracted with several portions of ethyl acetate and the combined extracts were washed successively with sodium bicarbonate and sodium chloride, dried ($Na_2SO_4$), filtered and concentrated under reduced pressure to provide ethyl$^2$-(1H-imidazo[4,5-c]pyridin-2-yl)propionate (60.4 g, 58%) as an amber solid. $^1$H-NMR (300 MHz, CDCl$_3$) d ppm: 9.00 (s, 1H), 8.35 (d, 1H, J=9.4 Hz), 7.50 (d, 1H, J=9.4 Hz), 4.25 (m, 3H), 1.78 (d, 3H, J=7.8 Hz), 1.30 (t, 3H, J=4.7 Hz).

(b) A solution comprising ethyl 2-(1H-imidazo[4,5-c]pyridin-2-yl)propionate (60.4 g, 0.28 mol) in trifluoroacetic acid (100 mL) was hydrogenation at 50 psi in the presence of platinum (IV) oxide (5 g) for 2 days. The mixture was filtered and concentrated under reduced pressure. The residue was cooled to 0° C., treated with 4M HCl/dioxane, suspended in ether, isolated by filtration and dried. Solutions comprising the residue (15–20 g each) in fresh trifluoroacetic acid (50 mL each) were hydrogentated at 50 psi in the presenced of platinum (IV) oxide (5 g each) for 24 hours. The mixtures were filtered and concentrated under reduced pressure. The residues were azeotropically dried with a mixture of toluene/ethanol ~1:1, with 4 M HCl/dioxane, suspended in ether, isolated by filtration and dried on the vacuum line to provide ethyl 2-(4,5,6,7-tetrahydroimidazo[4,5-c]pyridin-2-yl)propionate dihydrochloride (61.80 g, 75% yield); $^1$H-NMR (300 MHz, DMSO-d$_6$) d ppm: 10.00 (br s, 2H), 4.35 (q, 1H, J=7.1 Hz), 4.25 (br s, 2H), 4.15 (m, 2H), 3.35 (m, 2H), 2.90 (br s, 2H), 1.60 (d, 3H, J=7.1 Hz), 1.20 (t, 3H, J=6.9 Hz).

(c) A solution comprising ethyl 2-(4,5,6,7-tetrahydroimidazo[4,5-c]pyridin-2-yl)propionate dihydrochloride (60.2 g, 0.20 mol) in acetonitrile (400 mL) was cooled to 0° C. under nitrogen, treated with N,N-diisopropylethylamine (35 mL, 0.20 mol), further cooled to ~–5° C. (ice/acetone) and then treated with benzyl chloroformate (58 mL, 0.41 mol) and N,N-diisopropylethylamine (70 mL, 0.40 mol) in alternating portions over 30 minutes. The mixture was cooled at –5° C. for 1 hour and allowed to warm to 20° C. and, after 16 hours, concentrated under reduced pressure. The residue was suspended in ether and the suspension was washed successively with sodium bicarbonate, sodium chloride, 0.1M hydrochloric acid and sodium chloride, dried ($Na_2SO_4$), filtered and concentrated under reduced pressure. The residue was dissolved in ethanol (320 mL) and the solution was cooled to –5° C. under nitrogen and then sodium ethoxide (21 wt %, 85 mL, 0.22 mol) was added dropwise over 1 hour while the reaction temperature was maintained below 0° C. The mixture was cooled at −5° C. for 1 hour, adjusted to neutral pH with 50 mL of 4M hydrochloric acid and concentrated under reduced pressure. The residue was dissolved in ethyl acetate and the solution was washed with sodium bicarbonate and sodium chloride, dried ($Na_2SO_4$), filtered and concentrated under reduced pressure. The residue was purified by silica gel chromatography (hexanes/ethyl acetate) to provide benzyl 2-(1-ethoxycarbonylethyl)-1,4,6,7-tetrahydroimidazo[4,5-c]pyridine-5-carboxylate (52 g, 72%) as a pale yellow oil; $^1$H-NMR (300 MHz, DMSO-$d_6$) d ppm: 11.72 (br s, 1H), 7.32 (s, 5H), 5.07 (s, 2H), 4.32 (br s, 2H), 4.02 (q, 2H, J=9.3 Hz), 3.77 (q, 1H, J=8.3 Hz), 3.66 (s, 2H), 2.55 (s, 2H), 1.38 (d, 3H, J=8.3 Hz), 1.13 (t, 3H, J=9.3 Hz).

(d) A mixture comprising benzyl 2-(1-ethoxycarbonylethyl)-1,4,6,7-tetrahydroimidazo[4,5-c]pyridine-5-carboxylate (6.37 g, 0.018 mol), 4-amino-3-(N-methylamino)benzoic acid (2.70 g, 0.016 mol) and DMPU (20 mL) was degassed briefly on a vacuum line, heated heated at 185° C. under nitrogen for 4 hours, cooled and combined with an equivalent volume of benzene. Ether was then added to the mixture to give a precipitate. The precipitate was isolated by filtration, dried briefly on a vacuum line and further purified by a reprecipitation from hot ethanol/water. The precipitate was isolated recovered by filtration and dried to provided 2-[1-(5-benzyloxycarbonyl-4,5,6,7-tetrahydro-1H-imidazo[4,5-c]pyridin-2-yl)ethyl]-3-methyl-3H-benzoimidazole-5-carboxylic acid (4.73 g, 58%); $^1$H-NMR (300 MHz, DMSO-$d_6$) d ppm: 12.70 (br s, 1H), 11.80 (s, 1H), 8.15 (s, 1H), 7.78 (d, 1H, J=8.3 Hz), 7.64 (d, 1H, J=8.3 Hz), 7.31 (s, 5H), 5.09 (s, 2H), 4.66 (q, 1H, J=5.2 Hz), 4.32 (br s, 2H), 3.78 (s, 3H), 3.65 (br s, 2H), 2.52 (br s, 2H), 1.73 (d, 3H, J=5.2 Hz).

(e) A mixture comprising 2-[1-(5-benzyloxycarbonyl-4,5,6,7-tetrahydro-1H-imidazo[4,5-c]pyridin-2-yl)ethyl]-3-methyl-3H-benzoimidazole-5-carboxylic acid (0.75 g, 1.6 mmol), DMF (6.5 mL), methyl 2-(2-aminoethoxy)benzoate (0.38 g, 1.6 mmol) and HOBT (0.22 g, 1.6 mmol) was cooled under nitrogen to −40° C., treated with EDC (0.32 g, 1.6 mmol) and N,N-diisopropylethylamine (0.29 mL, 1.6 mmol) and 15 minutes later with additional N,N-diisopropylethylamine (0.29 mL), allowed to warm to 20° C. and stirred for 16 hours. The mixture then was cooled to −40° C., treated with additional EDC (0.080 g) and N,N-diisopropylethylamine (0.050 mL), stirred for 15 minutes at −40° C. and 2 hours at 20° C. and concentrated by shortpath distillation. The residue was partitioned between chloroform and sodium bicarbonate and the organic layer was washed with sodium chloride, 0.5M potassium sulfate and sodium chloride, dried ($Na_2SO_4$), filtered and concentrated under reduced pressure. The residue was purified by silica gel chromatography ($CHCl_3$/MeOH/AcOH: 95/5/1) to provide benzyl 2-(1-{6-[2-(2-methoxycarbonylphenoxy)ethylcarbamoyl]-1-methyl-1H-benzoimidazol-2-yl}ethyl)-1,4,6,7-tetrahydroimidazo[4,5-c]pyridine-5-carboxylate (0.69 g, 66%) as a glassy brown foam; $^1$H-NMR (300 MHz, DMSO-$d_6$) d ppm: 11.92 (s, 1H), 8.49 (t, 1H, J=5.0 Hz), 8.02 (s, 1H), 7.69 (d, 1H, J=9.9 Hz), 7.60 (m, 2H), 7.50 (t, 1H, J=8.3 Hz), 7.30 (m, 5H), 7.19 (d, 1H, J=9.9 Hz), 6.99 (t, 1H, J=8.3 Hz), 5.04 (s, 2H), 4.61 (q, 1H, J=8.8 Hz), 4.30 (br s, 2H), 4.20 (t, 2H, J=5.0 Hz), 3.74 (s, 3H), 3.68 (s, 3H), 3.63 (m, 4H), 2.55 (br s, 2H), 1.67 (d, 3H, J=8.8 Hz).

(f) A solution comprising benzyl 2-(1-{6-[2-(2-methoxycarbonylphenoxy)ethylcarbamoyl]-1-methyl-1H-benzoimidazol-2-yl}ethyl)-1,4,6,7-tetrahydroimidazo[4,5-c]pyridine-5-carboxylate (0.69 g, 1.1 mmol) in THF (2 mL) and water (2 mL) was cooled to 0° C. under nitrogen, treated with 2N lithium hydroxide (1.1 mL, 2.2 mmol), allowed to warm to 20° C. and stirred for 8 hours. The mixture then was cooled to 0C, treated with additional 2N lithium hydroxide (1.1 mL), allowed to warm to 20° C., stirred for 6 hours, cooled to 0° C., adjusted to pH 7 with 1M hydrochloric acid and concentrated under reduced pressure. The residue was carefully washed with cold sodium chloride and water and then dried on the vacuum line to provide 5-benzyloxycarbonyl-2-(2-{3-methyl-2-[1-(4,5,6,7-tetrahydro-1H-imidazo[4,5-c]pyridin-2-yl)ethyl]-3H-benzoimidazol-5-ylcarbonylaminoethoxy)benzoic acid (0.56 g, 83%) as a glassy residue; $^1$H-NMR (300 MHz, DMSO-$d_6$) d ppm: 11.87 (br s, 1H), 9.74 (s, 1H), 8.45 (s, 1H), 7.84 (d, 1H, J=9.7 Hz), 7.56 (d, 1H, J=9.7 Hz), 7.42 (d, 1H, J=7.7 Hz), 7.32 (s, 5H), 7.23 (t, 1H, J=7.7 Hz), 7.06 (d, 1H, J=7.7 Hz), 6.90 (t, 1H, J=7.7 Hz), 5.08 (s, 2H), 4.63 (q, 1H, J=7.7 Hz), 4.32 (s, 2H), 4.19 (m, 2H), 3.84 (s, 3H), 3.64 (m, 4H), 2.55 (s, 2H), 1.71 (d, 3H, J=7.7 Hz).

(g) A solution comprising 5-benzyloxycarbonyl-2-(2-{3-methyl-2-[1-(4,5,6,7-tetrahydro-1H-imidazo[4,5-c]pyridin-2-yl)ethyl]-3H-benzoimidazol-5-ylcarbonylamino}ethoxy) benzoic acid (0.561 g, 0.90 mmol) in glacial acetic acid (2 mL) was heated under nitrogen in a water bath to 10° C., treated with hydrogen bromide in acetic acid (2 mL of a 30% solution) and allowed to warm to 20° C. and, one hour later, concentrated with a stream of nitrogen. The residue was dissolved in a small quantity of ethanol and the solution was added dropwise to stirring ether to give a pale brown precipitate. The precipitate was isolated by filtration and dried to provide 2-(2-{3-methyl-2-[4,5,6,7-tetrahydro-1H-imidazo[4,5-c]pyridin-2-yl)ethyl]-3H-benzoimidazol-5-ylcarbonylamino}ethoxy)benzoic acid hydrobromide (0.651 g); $^1$H-NMR (300 MHz, DMSO-$d_6$) d ppm: 9.31 (br s, 2H), 8.63 (m, 1H), 8.24 (s, 1H), 7.79 (d, 1H, J=7.9 Hz), 7.63 (m, 2H), 7.47 (t, 1H, J=7.9 Hz), 7.21 (d, 1H, J=7.9 Hz), 7.00 (t, 1H, J=7.9 Hz), 5.21 (q, 1H, J=6.3 Hz), 4.29 (s, 2H), 4.21 (s, 2H), 3.91 (s, 3H), 3.68 (m, 2H), 3.43 (m, 2H), 2.89 (s, 2H), 1.79 (d, 3H, J=6.3 Hz).

(h) A solution comprising 2-(2-{3-methyl-2-[4,5,6,7-tetrahydro-1H-imidazo[4,5-c]pyridin-2-yl)ethyl]-3H-benzoimidazol-5-ylcarbonylamino}ethoxy)benzoic acid hydrobromide (0.30 g, 0.46 mmol) in DMF (1.5 mL) was cooled under nitrogen to 0° C., treated with ethyl acetimidate (0.12 g, 0.92 mmol) and N,N-diisopropylethylamine (0.25 mL, 1.4 mmol), cooled at 0° C. for 30 minutes and then allowed to warm to 20° C. and stirred for 20 hours. The mixture then was cooled to 0° C., treated with additional ethyl acetimidate (0.06 g) and of N,N-diisopropylethylamine (0.16 mL), allowed to warm to 20° C. and stirred for 2 hours. The mixture was cooled to 0° C., treated with additional ethyl acetimidate (0.03 g), allowed to warm to 20° C. and stirred for 2 hours. The mixture then was added dropwise to stirring ether to give a precipitate. The precipitate was isolated by decantating away the solvent and dried on a vacuum line. The residue was precipitated from ethanol/ether and purified by preparative RP-HPLC: 250% MeCN/H2O (20 mM HCl) over 50 minutes. The fractions were lyophilized to provide 2-[2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)ethoxy] benzoic acid (0.145 g, 52%); $^1$H-NMR (300 MHz, DMSO-$d_6$) d ppm: 9.77 (s, 1H), 9.34 (2s, 1H), 8.81 (m, 1H), 8.36 (s, 1H), 7.89 (d, 1H, J=8.6 Hz), 7.71 (d, 1H, J=8.6 Hz), 7.60 (d, 1H, J=7.7 Hz), 7.49 (t, 1H, J=7.7 Hz), 7.21 (d, 1H, J=7.7 Hz), 6.99 (t, 1H, J=7.7 Hz), 5.37 (m, 1H), 4.71 (2s, 2H), 4.23 (s, 2H), 3.97 (s, 3H), 3.82 (s, 1H), 3.66 (m, 2H), 2.83 (m, 2H), 2.49 (s, 1H), 2.40 (d, 3H, J=3.5 Hz), 1.85 (d, 3H, J=5.1 Hz). MS (ESI) $C_{28}H_{31}N_7O_4$ m/e calcd. 529.61, observed 530.3 ($MH^+$).

Example 10 ethyl 2-(2-{2-[1-(4,6,7-trifluoro-1H-benzoimidazol-2-yl)ethyl]-3-methyl-3H-benzoimidazol-5-carbonylamino}ethoxy}benzoate (Compound 75)

(a) A solution comprising 2,3,4,6-tetrafluoronitrobenzene (0.6 g, 3.1 mmol) and ammonia in dioxane (Aldrich, 0.5M, 7.5 mmol) was stirred at room temperature for 3 hours to give a fine white precipitate. The mixture was diluted with an equal volume of water to dissolve the white precipitate and give yellow crystals. The crystals were isolated were collected and dried to provide 2,3,5-trifluoro-6-nitroaniline (307 mg, 51%) as yellow needles; m.p. 66° C.; $^1$H NMR (CDCl$_3$) δ 6.4 (1H, m), δ 6.0 (2H, s).

(b) A mixture of 2,3,5-trifluoro-6-nitroaniline (300 mg, 1.56 mmol) and 10% palladium on carbon in absolute ethanol was hydrogenated overnight at atmospheric pressure, filtered under nitrogen and concentrated to provide 1,2-diamino-3,4,6-trifluorobenzene (219 mg, 87% yield) as a purple crystalline solid; MS M$^+$ 162.7, +41. +82 (+ACN, +2ACN). (calcd for C$_6$H$_5$F$_3$N$_2$: 162.11).

(c) A mixture of 1,2-diamino-3,4,6-trifluorobenzene (1.92 g, 11.8 mmol), ethyl 2-ethoxycarbonimidoylpropionate (3.1 g, 14.7 mmol) and absolute ethanol (6 ml) was heated at reflux until no further progression of the reaction was indicated by TLC indicated the reaction was not progressing further, filtered from NH$_4$Cl and concentrated. The residue was purified by chromatography on silica (hexane: methylene chloride: ethyl acetate, 5:5:1) to give ethyl 2-(4,6,7-trifluoro-1H-benzoimidazol-2-yl)propionate (1.37 g, 42%) as a tan crystalline solid; NMR (CDCl$_3$): δ 10.35 (s, ½H), δ 7.05 (s, ½H), 6.7 (m, 1H), δ 4.25 (dd, 2H), δ 4.15 (dd, 1H), δ 1.73 (d, 3H), δ 1.31 (t, 3H); M$^+$ 272.9 (calcd for C$_{12}$H$_{11}$F$_3$N$_2$O$_2$: 272.23).

(d) Ethyl 2-(4,6,7-trifluoro-1H-benzoimidazol-2-yl)propionate (988 mg, 3.63 mmol) and ethyl 2-[2-(4-amino-3-methylaminobenzoylamino)ethoxy]benzoate (1.3 g, 3.63 mmol) were combined and placed under vacuum for 4 hours and then further combined with DMPU (4 ml). The mixture was stirred until in solution, evacuated overnight under high vacuum to remove residual gases, heated to 195° C. under a nitrogen stream for 4 hours, cooled to room temperature and partitioned between ethyl acetate and water. The organic layer was separated and washed with brine, dried over sodium sulfate and concentrated. The residue was purified by chromatography on silica (stepwise gradient of 100% hexane to 100% ethyl acetate) and further purified by crystallization from MeOH/THF/water to provide ethyl 2-(2-{2-[1-(4,6,7-trifluoro-1H-benzoimidazol-2-yl)ethyl]-3-methyl-3H-benzoimidazol-5-carbonylamino}ethoxy}benzoate (1.0 g, 49%) as a white crystalline solid:

NMR (CDCl$_3$): δ 6.84–8.07 (m, 8H), δ 4.93 (dd, 1H), δ 4.34 (dd, 2H), δ 4.27 (m, 2H), δ 3.95 (m, 2H), δ 3.9 (s, 3H), δ 1.93 (d, 3H), δ 1.78 (s, 2H), δ 1.38 (t, 3H); LCMS M$^+$ 566.2 BioIon M$^+$ 565.7 (calcd for C$_{29}$H$_{26}$F$_3$N$_5$O$_4$: 565.55).

Proceeding as in Example 10 the following compounds of the invention were prepared:

ethyl 2-(2-{2-[1-(5,6-difluoro-1H-benzoimidazol-2-yl)ethyl]-3-methyl-3H-benzoimidazol-5-ylcarbonylamino}ethoxy)benzoate (Compound 76), MS (BioIon) C$_{29}$H$_{27}$N$_5$O$_4$F$_2$ m/e calc 547.56; found 548.1 (MH$^+$);

ethyl 2-(2-{2-[1-(4,6-difluoro-1H-benzoimidazol-2-yl)ethyl]-3-methyl-3H-benzoimidazol-5-ylcarbonylamino}ethoxy)benzoate (Compound 77, MS (LCMS) C$_{29}$H$_{27}$F$_2$N$_5$O$_4$ m/e calc 547.56; found 548.3 (MH$^+$);

ethyl 2-(2-{2-[1-(4,5,6-trifluoro-1H-benzoimidazol-2-yl)ethyl]-3-methyl-3H-benzoimidazol-5-ylcarbonylamino}ethoxy)benzoate (Compound 78), MS (LCMS) C$_{29}$H$_{26}$F$_3$N$_5$O$_4$ m/e calc 565.55; found 566.2 (MH$^+$); and ethyl 2-{2-[3-methyl-2-(4,6,7-trifluoro-1H-benzoimidazol-2-ylmethyl)-3H-benzoimidazol-5-ylcarbonylamino]ethoxy}benzoate (Compound 79), MS (BioIon) C$_{28}$H$_{24}$F$_3$N$_5$O$_4$ m/e calc 551.52; found 551.2.

Example 11

2-(2-{2-[1-(4,6,7-Trifluoro-1H-benzoimidazol-2-yl)ethyl]-3-methyl-3H-benzoimidazol-5-ylcarbonylamino}ethoxy)benzoic acid (Compound 80)

A mixture comprising ethyl 2-(2-{2-[1-(4,6,7-trifluoro-1H-benzoimidazol-2-yl)ethyl]-3-methyl-3H-benzoimidazol-5-carbonylamino}ethoxy}benzoate (118 mg, 0.21 mmol), methanol (4 ml) and 2N sodium hydroxide (2.1 ml) was stirred at room temperature for 4 hours, neutralized with 2N hydrochloric acid (2.1 ml) and partitioned between ethyl acetate and saturated ammonium chloride. The aqueous layer was separated and extracted with ethyl acetate (X3). The combined organic layers were washed with brine, dried over sodium sulfate and concentrated to a white solid. The residue was dissolved in warm ethanol (10 ml) and 4M hydrogen chloride/dioxane solution. The solution was diluted with ethyl ether to give a precipitate. The precipitate was isolated and dried to give 2-(2-{2-[1-(4,6,7-trifluoro-1H-benzoimidazol-2-yl)ethyl]-3-methyl-3H-benzoimidazol-5-ylcarbonylamino}ethoxy)benzoic acid as a white solid; MS (LCMS) C$_{27}$H$_{22}$F$_3$N$_5$O$_4$ m/e calc 537.50; found 538.4 (MH$^+$).

Proceeding as in Example 1 the following compounds of the invention were prepared:

2-(2-{2-[1-(5,6-difluoro-1H-benzoimidazol-2-yl)ethyl]-3-methyl-3H-benzoimidazol-5-ylcarbonylamino}ethoxy)benzoic acid (Compound 81), MS (LCMS) C$_{27}$H$_{23}$N$_5$O$_4$F$_2$ m/e calc 519.51; found 520.2 (MH$^+$);

2-(2-{2-[1-(4,6-difluoro-1H-benzoimidazol-2-yl)ethyl]-3-methyl-3H-benzoimidazol-5-ylcarbonylamino}ethoxy)benzoic acid (Compound 82), MS (LCMS) C$_{27}$H$_{23}$F$_2$N$_5$O$_4$ m/e calc 519.51; found 520.2 (MH$^+$); and 2-(2-{2-[1-(4,5,6-trifluoro-1H-benzoimidazol-2-yl)ethyl]-3-methyl-3H-benzoimidazol-5-carbonylamino}ethoxy)benzoic acid (Compound 83), MS (BioIon) C$_{27}$H$_{22}$F$_3$N$_5$O$_4$ m/e calc 537.5; found 537.7 (MH$^+$).

Example 12

Ethyl 2-(2-{2-[1-(1-isobutyryl-5-methoxycarbonyloxy-1H-benzoimidazol-2-yl)ethyl]-3-methyl-3H-benzoimidazol-5-ylcarbonylamino}ethoxy)benzoate (Compound 84)

A mixture comprising ethyl 2-(2-{2-[1-(5-hydroxy-1H-benzoimidazol-2-yl)ethyl]-3-methyl-3H-benzoimidazol-5- carbonylamino}ethoxy)benzoate (0.50 g, 0.95 mmol), dimethylformamide (5 mL), cesium carbonate (0.93 g, 2.85 mmol) and isobutyric anhydride (0.17 mL, 1.05 mmol) was stirred for 2 hours, then diluted with dichloromethane (50 mL) and passed through a celite pad. The solvents were removed in vacuo and the residue was dissolved in dichloromethane (5 mL). The solution was combined with diisopropylethylamine (0.47 mL, 2.7 mmol) and methyl chloroformate (0.1 mL, 1.3 mmol) and the mixture was stirred for 1 hour. The solvents were removed in vacuo and the residue was purified by silica gel chromatography using ethanol and dichloromethane as eluent to provide ethyl 2-(2-{2-[1-(1-isobutyrl-5-methoxycarbonyloxy-1H-benzoimidazol-2-yl)ethyl]-3-methyl-3H-benzoimidazol-5-ylcarbonylamino}ethoxy)benzoate (0.20 g, 32% yield) as a colorless amorphous solid; MS (BioIon) $C_{35}H_{37}N_5O_8$ m/e calc 655.72; found 656.1 (MH$^+$).

Proceeding as in Example 12 the following prodrug derivatives of the invention were prepared:

methyl 2-(1-{6-[2-(2-ethoxycarbonylphenoxy)ethylcarbamoyl]-1-methyl-1H-benzoimidazol-2-yl}ethyl)-5-hydroxybenzoimidazole-1-carboxylate (Compound 85), MS (ESI) $C_{31}H_{31}N_5O_7$ m/e calc 585.62; found 586.2 (MH$^+$);

ethyl 2-(1-{6-[2-(2-ethoxycarbonylphenoxy)ethylcarbamoyl]-1-methyl-1H-benzoimidazol-2-yl}ethyl)-5-methoxycarbonyloxybenzoimidazole-1-carboxylate (Compound 86), MS (ESI) $C_{33}H_{33}N_5O_7$ m/e calc 643.66; found 644.2 (MH$^+$);

ethyl 2-(2-{2-[1-(5-hydroxy-1-isobutyryl-1H-benzoimidazol-2-yl)ethyl]-3-methyl-3H-benzoimidazol-5-ylcarbonylamino}ethoxy)benzoate (Compound 87), MS (ESI) $C_{33}H_{35}N_5O_6$ m/e calc 597.68; found 598.2 (MH$^+$);

ethyl 2-(2-{2-[1-(1-benzoyl-5-hydroxy-1H-benzoimidazol-2-yl)ethyl]-3-methyl-3H-benzoimidazol-5-ylcarbonylamino}ethoxy)benzoate (Compound 88), MS (ESI) $C_{36}H_{33}N_5O_6$ m/e calc 631.69; found 632.3 (MH$^+$);

ethyl 2-(2-{2-[1-(1-dimethylcarbamoyl-5-hydroxy-1H-benzoimidazol-2-yl)ethyl]-3-methyl-3H-benzoimidazol-5-ylcarbonylamino)ethoxy}benzoate (Compound 89), MS (ESI) $C_{32}H_{34}N_6O_6$ m/e calc 598.66; found 599.3 (MH$^+$);

ethyl 2-(2-{2-[1-(1-acetoxymethyl-5-hydroxy-1H-benzoimidazol-2-yl)ethyl]-3-methyl-3H-benzoimidazol-5-ylcarbonylamino}ethoxy)benzoate (Compound 90), MS (BioIon) $C_{32}H_{33}N_5O_7$ m/e calc 599.65; found 600.7 (MH$^+$);

ethyl 2-[2-(2-{1-[1-(2,2-dimethylpropionyloxymethyl)-5-hydroxy-1H-benzoimidazol-2-yl]ethyl}-3-methyl-3H-benzoimidazol-5-ylcarbonylamino)ethoxy]benzoate (Compound 91), MS (ESI) $C_{35}H_{39}N_5O_7$ m/e calc 641.74; found 642.3 (MH$^+$);

ethyl 2-(2-{2-[1-(1-isobutyrl-5-methoxycarbonyloxy-1H-benzoimidazol-2-yl)ethyl]-3-methyl-3H-benzoimidazol-5-ylcarbonylamino}ethoxy)benzoate (Compound 92), MS (BioIon) $C_{35}H_{37}N_5O_8$ m/e calc 655.72; found 656.1 (MH$^+$);

ethyl 5-ethoxycarbonyloxy-2-(1-{6-[2-(2-ethoxycarbonylphenoxy)ethylcarbamoyl]-1-methyl-1H-benzoimidazol-2-yl}ethyl)benzoimidazole-1-carboxylate (Compound 93), MS (ESI) $C_{35}H_{37}N_5O_9$ m/e calc 671.72; found 672.4 (MH$^+$);

isopropyl 2-(1-{6-[2-(2-ethoxycarbonylphenoxy)ethylcarbamoyl]-1-methyl-1H-benzoimidazol-2-yl}ethyl)-5-isopropoxycarbonyloxy-benzoimidazole-1-carboxylate (Compound 94), MS (ESI) $C_{37}H_{41}N_5O_9$ m/e calc 699.79; found 700.4 (MH$^+$); and ethyl 2-(2-{2-[1-(1-acetyl-5-hydroxy-1H-benzoimidazol-2-yl)ethyl]-3-methyl-3H-benzoimidazol-5-ylcarbonylamino}ethoxy)benzoate (Compound 95), MS (ESI) $C_{31}H_{31}N_5O_6$ m/e calc 569.62; found 570.1 (MH$^+$).

Proceeding as described in this application or by methods known to those of ordinary skill the following additional compounds of the invention were prepared:

C-[2-(5-aminomethyl-1H-benzoimidazol-2-ylmethyl)-3H-benzoimidazol-5-yl]methylamine (Compound 96);

C-[2-(1H-naphtho[2,3-d]imidazol-2-ylmethyl)-1H-benzoimidazol-5-yl]methylamine (Compound 97), MS (BioIon) $C_{20}H_{17}N_5$ m/e calc 327.4; found 328.1 (MH$^+$);

C-[2-(5-methyl-1H-benzoimidazol-2-ylmethyl)-1H-benzoimidazol-5-yl]methylamine (Compound 98), MS (BioIon) $C_{17}H_{17}N_5$ m/e calc 291.4; found 292.3 (MH$^+$);

2-(5-aminomethyl-1H-benzoimidazol-2-ylmethyl)-1H-benzoimidazole-5-carboxylic acid (Compound 99);

3-[2-(5-aminomethyl-1H-benzoimidazol-2-ylmethyl)-1H-benzoimidazol-5-ylcarbonylamino]propionic acid (Compound 100), $^1$H-NMR (300 Mhz, CD$_3$OD): 1.92 (m, 2H, J=7.2Hz), 2.38 (t, 2H, J=7.2 Hz), 3.47 (t, 2H, J=7.2 Hz), 4.30 (s, 2H), 7.54 (d, 1H, J=10.0 Hz), 7.69 (d, 1H, J=8.6 Hz), 7.75 (d, 1H, J=10.0 Hz), 7.81 (s, 1H), 7.87 (d, 1H, J=8.6 Hz), 8.12 (s, 1H);

2-(5-aminomethyl-1H-benzoimidazol-2-ylmethyl)-N-(2-naphth-1-ylethyl)-1H-benzoimidazole-5-carboxamide (Compound 101), $^1$H-NMR (300 Mhz, CD$_3$OD): 3.42 (t, 2H, J=7.5 Hz), 3.75 (t, 2H, J=7.5 Hz), 7.39–7.81 (m, 12H), 8.08 (s, 1H), 8.27 (d, 1H, J=10.0 Hz);

2-(5-aminomethyl-1H-benzoimidazol-2-ylmethyl)-3-methyl-N-(2-naphth-1-ylethyl)-3H-benzoimidazole-5-carboxamide (Compound 102), $^1$H-NMR (300 Mhz, CD$_3$OD): 3.41 (t, 2H, J=7.4 Hz), 3.72 (t, 2H, J=7.4 Hz), 3.96 (s, 3H), 4.27 (s, 2H), 7.37–7.54 (m, 5H), 7.67 (d, 1H, J=8.7 Hz), 7.71–7.77 (m, 2H), 7.80–7.85 (m, 2H), 8.70 (d, 1H, J=0.9 Hz), 8.24 (d, 1H, J=8.1 Hz);

2-(5-aminomethyl-1H-benzoimidazol-2-ylmethyl)-3-methyl-N-(2-naphth-1-ylethyl)-3H-benzoimidazole-4-carboxamide (Compound 103), $^1$H-NMR (300 Mhz, CD$_3$OD): 3.45 (t, 2H, J=7.2 Hz), 3.74 (s, 3H), 3.83 (t, 2H, J=7.2 Hz), 4.27 (s, 2H), 7.36–7.55 (m, 7H), 7.71–7.77 (m, 3H), 7.83–7.86 (m, 2H), 8.24 (d, 1H, J=8.1 Hz);

(S)-2-[2-(5-aminomethyl-1H-benzoimidazol-2-ylmethyl)-1H-benzoimidazol-5-ylcarbonylamino]-3-indol-3-ylpropionic acid (Compound 104), $^1$H-NMR (300 Mhz, CD$_3$OD): 3.36 (dd, 1H, J=14.6, 8.1 Hz), 3.53 (dd, 1H, J=14.6, 5.0 Hz), 3.92 (s, 3H), 4.27 (s, 2H), 6.97 (t, 1H, J=7.4 Hz), 7.07 (t, 1H, J=7.4 Hz), 7.16 (s, 1H), 7.33 (d, 1H J=7.8 Hz), 7.51 (dd, 1H, J=8.4,1.5 Hz), 7.60–7.66 (m, 2H), 7.73–7.80 (m, 3H), 7.96 (d, 1H, J=0.9 Hz), 8.39 (d, J=7.5 Hz, partially exchanged);

(R)-2-[2-(5-aminomethyl-1H-benzoimidazol-2-ylmethyl)-1H-benzoimidazol-5-ylcarbonylamino]-3-indol-3-ylpropionic acid (Compound 105), $^1$H-NMR (300 Mhz, CD$_3$OD): 3.35 (dd, 1H, J=14.5, 8.1 Hz), 3.51 (dd, 1H, J=14.4, 4.8 Hz), 3.90 (s, 3H), 4.23 (s, 2H), 6.96 (t, 1H, J=7.4 Hz), 7.06 (t, 1H, J=7.4 Hz), 7.14 (s, 1H), 7.31 (d, 1H, J=7.8 Hz), 7.44 (d, 1H, J=7.8 Hz), 7.58–7.74 (m, 5H), 7.94 (s, 1H), 8.33 (d, J=8.1 Hz, partially exchanged);

2-(1H-benzoimidazol-2-ylmethyl)-N-(2-naphth-1-ylethyl)-1H-benzoimidazole-5-carboxamide (Compound 106), $^1$H-NMR (300 Mhz, CD$_3$OD): 3.42 (t, 2H, J=7.4 Hz), 3.76 (t, 2H, J=7.4 Hz), 3.97 (s, 3H), 7.38–7.60 (m, 5H), 7.65 (d, 1H, J=8.7Hz), 7.72–7.79 (m, 4H), 7.85 (dd, 1H, J=8.6,1.5 Hz), 8.04 (d, 1H, J=1.2 Hz), 8.26 (d, 1H, J=8.4 Hz);

2-(5-aminomethyl-1H-benzoimidazol-2-ylmethyl)-3-methyl-N-(4-aminobutyl)-3H-benzoimidazole-4-carboxamide (Compound 107), MS (BioIon) C$_{22}$H$_{27}$N$_7$O, m/e calc 405.4; found 406.5 (MH$^+$);

2-[1-(5-aminomethyl-1H-benzoimidazol-2-yl)ethyl]-3-methyl-N-(2-naphth-1-ylethyl)-3H-benzoimidazole-5-carboxamide (Compound 108), MS (BioIon) C$_{31}$H$_{30}$N$_6$O$_1$ m/e calc 502.6; found 503.3 (MH$^+$);

2-(1H-imidazo[4,5-c]pyridin-2-ylmethyl)-3-methyl-N-(2-naphth-1-ylethyl)-3H-benzoimidazole-5-carboxamide (Compound 109), MS (BioIon) C$_{28}$H$_{24}$N$_6$O$_1$ m/e calc 460.5; found 461.3 (MH$^+$);

2-(5-aminomethyl-1H-benzoimidazol-2-ylcarbonyl)-3-methyl-N-(2-naphth-1-ylethyl)-3H-benzoimidazole-5-carboxamide (Compound 110), MS (BioIon) C$_3$H$_{26}$N$_6$O$_2$ m/e calc 502.6; found 503.6 (MH$^+$);

2-(5-carbamoyl-1H-benzoimidazol-2-ylmethyl)-N-(2-naphth-1-ylethyl)-1H-benzoimidazole-5-carboxamide (Compound 111), 2-(5-aminomethyl-4,5,6,7-tetrahydro-1H-benzoimidazol-2-ylmethyl)-3-methyl-N-(2-naphth-1-ylethyl)-3H-benzoimidazole-5-carboxamide (Compound 112), $^1$H-NMR (300 Mhz, CD$_3$OD): 1.67 (m, 1H), 2.14 (m, 1H), 2.24 (m, 1H), 2.47 (dd, 1H, J=15.3, 9.3 Hz), 2.76 (m, 2H), 2.90 (dd, 1H, J=15.7, 7.5 Hz), 3.05 (d, 2H, J=6.9 Hz), 3.41 (t, 2H, J=7.4 Hz), 3.75 (t, 2H, J=7.4 Hz), 3.90 (s, 3H), 7.35–7.53 (m, 5H), 7.61 (d, 1H, J=8.4 Hz), 7.72–7.75 (m, 2H), 7.85 (dd, 1H, J=8.1,1.2 Hz), 7.99 (d, 1H, J=0.9 Hz), 8.26 (d, 1H, J=8.4 Hz);

2-(5-aminomethyl-1H-benzoimidazol-2-ylmethyl)-3-methyl-N-(3-phenylpropyl)-3H-benzoimidazole-5-carboxamide (Compound 113), $^1$H-NMR (300 Mhz, CD$_3$OD): 1.98 (m, 2H), 2.72 (t, 2H, J=7.6 Hz), 3.46 (t, 2H, J=7.2 Hz), 4.01 (s, 3H), 4.29 (s, 2H), 7.12–7.17 (m, 1H), 7.21–7.28 (m, 4H), 7.56 (d, 1H, J=8.1 Hz), 7.70 (d, 1H, J=8.7 Hz), 7.77 (d, 1H, J=8.4 Hz), 7.85–7.88 (m, 2H), 8.16 (s, 1H, J=1H);

2-(5-aminomethyl-1H-benzoimidazol-2-ylmethyl)-3-methyl-N-(2-phenoxyethyl)-3H-benzoimidazole-5-carboxamide (Compound 114), $^1$H-NMR (300 Mhz, CD$_3$OD): 3.80 (t, 2H, J=5.0 Hz), 3.99 (s, 3H), 4.17 (t, 2H, J=5.0 Hz), 4.27 (s, 2H), 6.88 (t, 1H, J=7.5Hz), 6.92 (d, 2H, J=7.5 Hz), 7.22 (t, 2H, J=7.5 Hz), 7.55 (d, 1H, J=8.7 Hz), 7.68 (d, 1H, J=6.6 Hz), 7.77 (d, 1H, J=8.4 Hz), 7.84 (s, 1H), 7.88 (d, 1H, J=8.7 Hz), 8.18 (s, 1H);

2-[5-(1-iminoethyl)-4,5,6,7-tetrahydro-1H-imidazo[4,5-c]pyridin-2-ylmethyl]-3-methyl-N-(2-naphth-1-ylethyl)-3H-benzoimidazole-5-carboxamide (Compound 115), $^1$H-NMR (300 Mhz, CD$_3$OD): 2.45 (2.43, s, 3H), 2.96 (m, 2H), 3.42 (t, 2H, J=7.4 Hz), 3.75 (t, 2H, J=7.4 Hz), 3.93 (s, 3H), 3.98 (m, 2H), 4.70 (4.80, s, 2H), 7.38–7.53 (m, 4H), 7.63–7.87 (m, 4H), 8.04 (d, J=1.5 Hz, 8.08, s, 1H), 8.26 (d, 1H, J=8.0 Hz);

2-[5-(1-iminoethyl)-4,5,6,7-tetrahydro-1H-imidazo[4,5-c]pyridin-2-ylcarbonyl]-3-methyl-N-(2-naphth-1-ylethyl)-3H-benzoimidazole-5-carboxamide (Compound 116), $^1$H-NMR (300 Mhz, CD$_3$OD): 2.45 (2.43, s, 3H), 3.03 (m, 2H), 3.41 (t, 2H, J=7.4 Hz), 3.74 (t, 2H, J=7.4 Hz), 3.97 (m, 2H), 4.18 (4.18, s, 3H), 4.66 (4.80, s, 2H), 7.38–7.54 (m, 4H), 7.72–7.92 (m, 4H), 8.04 (s, 1H), 8.26 (d, 1H, J=7.8 Hz);

2-(5-iminomethyl-4,5,6,7-tetrahydro-1H-imidazo[4,5-c]pyridin-2-ylmethyl)-3-methyl-N-(2-naphth-1-ylethyl)-3H-benzoimidazole-5-carboxamide (Compound 117), $^1$H-NMR (300 Mhz, CD$_3$OD): 2.95 (m, 2H), 3.40 (t, 2H, J=7.4 Hz), 3.74 (t, 2H, J=7.4 Hz), 3.90 (3.89, s, 3H), 3.98 (m, 2H), 4.70 (4.82, s, 2H), 7.39–7.52 (m, 4H), 7.63–7.84 (m, 4H), 8.03 (s, 1H), 8.16 (8.18, s, 1H), 8.24 (d, 1H, J=8.4 Hz);

2-(5-aminomethyl-4,5,6,7-tetrahydro-1H-benzoimidazol-2-ylcarbonyl)-3-methyl-N-(2-naphth-1-ylethyl)-3H-benzoimidazole-5-carboxamide (Compound 118), $^1$H-NMR (300 Mhz, CD$_3$OD): 1.69 (m, 1H), 2.15 (m, 1H), 2.20 (m, 1H), 2.55 (dd, 1H, J=15.0, 11.4 Hz), 2.81–3.08 (m, 5H), 3.44 (t, 2H, J=7.5 Hz), 3.74 (m, 2H), 4.23 (s, 3H), 7.39–7.52 (m, 4H), 7.75 (dd, 1H, J=6.1, 3.2 Hz), 7.83–7.88 (m, 2H), 7.97 (d, 1H, J=8.7 Hz), 8.10 (s, 1H), 8.27 (d, 1H, J=8.1 Hz);

2-[5-(1-iminoethyl)-4,5,6,7-tetrahydro-1H-imidazo[4,5-c]pyridin-2-ylmethyl]-3-methyl-N-(2-phenoxyethyl)-3H-benzoimidazole-5-carboxamide (Compound 119), $^1$H-NMR (300 Mhz, CD$_3$OD): 2.45 (2.43, s, 3H), 2.95 (m, 2H), 3.80 (t, 2H, J=5.6 Hz), 3.95 (s, 3H), 3.98 (m, 2H), 4.17 (t, 2H, J=5.6 Hz), 4.71 (4.81, s, 2H), 6.89 (t, 1H, J=7.3 Hz), 6.93 (d, 2H, J=8.6 Hz), 7.23 (dd, 2H, J=8.6, 7.3 Hz), 7.66 (d, 1H, J=7.8 Hz), 7.85 (d, 1H, J=7.8 Hz), 8.13 (s, 1H);

2-[5-(1-iminoethyl)-4,5,6,7-tetrahydro-1H-imidazo[4,5-c]pyridin-2-ylmethyl]-3-methyl-N-(2-benzo[1,3]dioxol-4-ylethyl)-3H-benzoimidazole-5-carboxamide (Compound 120), $^1$H-NMR (300 Mhz, CD$_3$OD): 2.45 (2.43, s, 3H), 2.89–2.97 (m, 4H), 3.65 (t, 2H, J=7.1 Hz), 3.94 (s, 3H), 3.98 (m, 2H), 4.71 (4.81, s, 2H), 5.83 (s, 2H), 6.65–6.74 (m, 3H), 7.64 (d, 1H, J=7.8 Hz), 7.76–7.79 (m, 1H), 8.06 (m, 1H);

2-[5-(1-iminoethyl)-4,5,6,7-tetrahydro-1H-imidazo[4,5-c]pyridin-2-ylmethyl]-3-methyl-N-(-benzoimidazol-1-ylethyl)-3H-benzoimidazole-5-carboxamide (Compound 121), $^1$H-NMR (300 Mhz, CD$_3$OD): 2.46 (2.44, s, 3H), 2.96 (m, 2H), 3.92 (s, 3H), 3.95–4.01 (m, 4H), 4.73 (4.79, s, 2H), 4.80 (m, 2H), 7.54–7.64 (m, 4H), 7.83 (dd, 1H, J=6.5, 2.2 Hz), 7.93 (s, 1H), 7.98 (dd, J=6.5, 2.1 Hz), 9.49 (s, 1H);

N-[2-(5-hydroxy-1H-indol-2-yl)ethyl]-2-[5-(1-iminoethyl)-4,5,6,7-tetrahydro-1H-imidazo[4,5-c]pyridin-2-ylmethyl]-3-methyl-3H-benzoimidazole-5-carboxamide (Compound 122), $^1$H-NMR (300 Mhz, CD$_3$OD): 2.42 (2.39, s, 3H), 2.90 (m, 2H), 2.99 (t, 2H, J=7.1 Hz), 3.67 (t, 2H, J=7.1 Hz), 3.75 (s, 3H), 3.93 (m, 2H), 4.66 (4.76, s, 2H), 6.61 (dd, 1H, J=8.5, 2.3 Hz), 6.94 (d, 1H, J=2.3 Hz), 7.06 (s, 1H), 7.12 (d, 1H, J=8.5 Hz), 7.59 (d, 1H, J=8.4 Hz), 7.76 (dd, 1H, J=8.4, 1.2 Hz), 7.87 (d, 1H, J=1.2 Hz);

2-[5-(1-iminoethyl)-4,5,6,7-tetrahydro-1H-imidazo[4,5-c]pyridin-2-ylmethyl]-3-methyl-N-[2-(2-chlorophenoxy)ethyl]-3H-benzoimidazole-5-carboxamide (Compound 123), MS (BioIon) C$_{26}$H$_{28}$N$_7$O$_2$C m/e calc 506.0; found 506.3 (MH$^+$);

2-[5-(1-iminoethyl)-4,5,6,7-tetrahydro-1H-imidazo[4,5-c]pyridin-2-ylmethyl]-3-methyl-N-[2-(3-chlorophenoxy)ethyl]-3H-benzoimidazole-5-carboxamide (Compound 124), MS (BioIon) C$_{26}$H$_{28}$N$_7$O$_2$Cl m/e calc 506.0; found 506.7 (MH$^+$);

2-[5-(1-iminoethyl)-4,5,6,7-tetrahydro-1H-imidazo[4,5-c]pyridin-2-ylmethyl]-3-methyl-N-(2-naphth-1-ylethyl)-3H-benzoimidazole-5-carboxamide (Compound 125), $^1$H-NMR (300 Mhz, CD$_3$OD): 2.48 (2.46, s, 3H), 3.00 (m, 2H), 3.60 (t, 2H, J=6.6 Hz), 3.90–4.05 (m, 7H), 4.76 (4.76, s, 2H), 6.64 (6.66, s, partially exchanged), 7.45–7.95 (m, 9H), 8.02 (m, partially exchanged), 8.17 (d, 1H, J=8.1 Hz), 8.96 (s, partially exchanged);

2-[5-(1-iminoethyl)-4,5,6,7-tetrahydro-1H-imidazo[4,5-c]pyridin-2-ylmethyl]-3-methyl-N-(2-hydroxy-2-naphth-1-ylethyl)-3H-benzoimidazole-5-carboxamide (Compound 126), 1H-NMR (300 Mhz, CD$_3$OD): 2.45 (2.43, s, 3H), 2.94 (m, 2H), 3.55 (dd, 1H, J=13.6, 8.3 Hz), 3.91–3.99 (m, 6H), 4.70 (4.80, s, 2H), 5.78 (dd, 1H, J=8.3, 3.6 Hz), 7.44–7.54 (m, 3H), 7.66 (d, 1H, J=8.4 Hz), 7.76–7.88 (m, 4H), 8.08 (m, 1H), 8.39 (d, 1H, J=8.4 Hz);

2-[5-(1-iminoethyl)-4,5,6,7-tetrahydro-1H-imidazo[4,5-c]pyridin-2-ylmethyl]-3-methyl-N-[2-(2-hydroxynaphth-1-yl)ethyl]-3H-benzoimidazole-5-carboxamide (Compound 127), $^1$H-NMR (300 Mhz, CD$_3$OD): 2.43 (2.41, s, 3H), 2.92 (m, 2H), 3.41 (t, 2H, J=7.1 Hz), 3.69 (t, 2H, J=7.1 Hz), 3.85 (s, 3H), 3.93–3.96 (m, 2H), 4.68 (4.78, s, 2H), 7.11 (d, 1H, J=8.7 Hz), 7.21 (t, 1H, J=7.5 Hz), 7.38 (dt, 1H, J=1.2, 7.6 Hz), 7.50–7.61 (m, 2H), 7.69–7.75 (m, 2H), 7.93 (s, 1H), 8.07 (d, 1H, J=8.4 Hz);

2-[5-(1-iminoethyl)-4,5,6,7-tetrahydro-1H-imidazo[4,5-c]pyridin-2-ylmethyl]-3-methyl-N-[2-(4-hydroxynaphthal-1-yl)ethyl]-3H-benzoimidazole-5-carboxamide (Compound 128), $^1$H-NMR (300 Mhz, CD$_3$OD): 2.42 (2.40, s, 3H), 2.89 (m, 2H), 3.27 (m, 2H), 3.69 (t, 2H, J=7.2 Hz), 3.82 (3.83, s, 3H), 3.93 (m, 2H), 4.64 (4.76, s, 2H), 6.72 (d, 1H, J=7.8 Hz), 7.17 (d, 1H, J=7.5 Hz), 7.37 (t, 1H, J=7.5 Hz), 7.46 (dt, 1H, J=0.9, 6.9 Hz), 7.62 (d, 1H, J=8.5 Hz), 7.77 (d, 1H, J=8.5 Hz), 7.95 (s, 1H), 8.12 (d, 1H, J=8.4 Hz), 8.17 (d, 1H, J 8.4 Hz);

2-[5-(1-iminoethyl)-4,5,6,7-tetrahydro-1H-imidazo[4,5-c]pyridin-2-ylmethyl]-3-methyl-N-[2-(2-methoxyphenoxy)ethyl]-3H-benzoimidazole-5-carboxamide (Compound 129), $^1$H-NMR (300 Mhz, CD$_3$OD): 2.45 (2.43, s, 3H), 2.95 (m, 2H), 3.80 (m, 5H), 3.95 (s, 3H), 3.98 (m, 2H), 4.17 (t, 2H,1J=5.4 Hz), 4.71 (4.81, s, 2H), 6.85–7.00 (m, 4H), 7.66 (d, H, J=8.7 Hz), 7.84 (m, 1H), 8.13 (s, 1H);

2-[5-(1-iminoethyl)-4,5,6,7-tetrahydro-1H-imidazo[4,5-c]pyridin-2-ylmethyl]-3-methyl-N-naphth-2-ylmethyl-3H-benzoimidazole-5-carboxamide (Compound 130), $^1$H-NMR (300 Mhz, CD$_3$OD): 2.44 (2.42, s, 3H), 2.92 (m, 2H), 3.91 (s, 3H), 3.95 (m, 2H), 4.68 (4.78, s, 2H), 4.77 (s, 2H), 7.41–7.44 (m, 2H), 7.50 (dd, 1h, J=8.6,1.1 Hz), 7.67 (d, 1H, J=8.4 Hz), 7.78–7.83 (m, 4H), 7.90 (m, 1H), 8.16 (m, 1H);

2-[5-(1-iminoethyl)-4,5,6,7-tetrahydro-1H-imidazo[4,5-c]pyridin-2-ylmethyl]-3-methyl-N-(3-pyrid-4-ylpropyl)-3H-benzoimidazole-5-carboxamide (Compound 131), $^1$H-NMR (300 Mhz, CD$_3$OD): 2.11 (m, 2H), 2.46 (2.43, s, 3H), 2.96 (m, 2H), 3.06 (t, 2H, J=7.7 Hz), 3.51 (t, 2H, J=6.8 Hz), 3.98 (m, 5H), 4.72 (4.82, s, 2H), 7.67 (d, 1H, J=8.5 Hz), 7.83 (dd, 1H, J=8.5, 1.3 Hz), 8.00 (d, 2H, J=6.6 Hz), 8.15 (d, 1H, J=1.3 Hz), 8.70 (d, 2H, J=6.6 Hz);

2-(5-guanidino-1H-benzoimidazol-2-ylmethyl)-3-(2,3-dihydroxy)propyl-N-(2-naphth-1-ylethyl)-3H-benzoimidazole-5-carboxamide (Compound 132), MS (BioIon) C$_{32}$H$_{32}$N$_8$O$_3$ m/e calc 576.6; found 577.5 (MH$^+$); $^1$H-NMR (300 Mhz, CD$_3$OD): 3.41 (t, 2H, J=7.5 Hz), 3.58–3.76 (m, 4H), 4.05 (m, 1H), 4.45 (dd, 1H, J=14.9, 8.5 Hz), 4.61 (dd, 1H, J=14.9, 3.2 Hz), 7.36–7.52 (m, 4H), 7.66–7.85 (m, 4H), 8.14 (s, 1H), 8.25 (d, 1H, J=7.8 Hz);

2-[5-(1-iminoethyl)-4,5,6,7-tetrahydro-1H-imidazo[4,5-c]pyridin-2-ylmethyl]-3-methyl-N-[2-(4-methoxyphenoxy)ethyl]-3H-benzoimidazole-5-carboxamide (Compound 133), $^1$H-NMR (300 Mhz, CD$_3$OD): 2.45 (2.43, s, 3H), 2.95 (m, 2H), 3.70 (m, 2H), 3.77 (t, 2H, J=5.6 Hz), 3.95 (s, 3H), 3.98 (m, 2H), 4.12 (t, 2H, J=5.6 Hz), 4.71 (4.81, s, 2H), 6.78–6.89 (m, 4H), 7.66 (d, 1H, J=8.4 Hz), 7.84 (m, 1H), 8.13 (d, 1H, J=1.2 Hz);

2-(5-guanidino-1H-benzoimidazol-2-ylcarbonyl)-3-(2,3-dihydroxy)propyl-N-(2-naphth-1-ylethyl)-3H-benzoimidazole-5-carboxamide (Compound 134), MS (BioIon) C$_{32}$H$_{30}$N$_7$O$_4$ m/e calc 590.6; found 590.7 (MH$^+$); $^1$H-NMR (300 Mhz, CD$_3$OD): 3.42 (t, 2H, J=7.4 Hz), 3.74 (t, 2H, J=7.4 Hz), 4.00 (d, 2H, J=4.2 Hz), 4.38 (t, 1H, J=11.7 Hz), 4.56 (dd, 1H, J=12.5, 3.5 Hz), 7.34–7.51 (m, 5H), 7.61–7.65 (m, 2H), 7.72–7.86 (m, 4H), 8.05 (d, 1H, J=1.2 Hz), 8.25 (d, 1H, J=8.1 Hz);

2-[5-(1-iminoethyl)-4,5,6,7-tetrahydro-1H-imidazo[4,5-c]pyridin-2-ylmethyl]-3-methyl-N-[2-(1,2,3,4-tetrahydronaphth-1-yl)ethyl]-3H-benzoimidazole-5-carboxamide (Compound 135), $^1$H-NMR (300 Mhz, CD$_3$OD): 1.69–2.11 (m, 6H), 2.45 (2.43, s, 3H), 2.73 (m, 2H), 2.88 (m, 1H), 2.95 (m 2H), 3.52 (t, 2H, J=7.4 Hz), 3.97 (m, 5H), 4.72 (4.81, s, 2H), 6.99–7.06 (m, 3H), 7.15-7.18 (m, 1H), 7.67 (d, 1H, J=8.7 Hz), 7.82–7.86 (m, 1H), 8.14 (d, 1H, J=0.9 Hz);

2-[5-(1-iminoethyl)-4,5,6,7-tetrahydro-1H-imidazo[4,5-c]pyridin-2-ylmethyl]-3-methyl-N-[2-(3-methoxyphenoxy)ethyl]-3H-benzoimidazole-5-carboxamide (Compound 136), $^1$H-NMR (300 Mhz, CD$_3$OD): 2.45 (2.42, s, 3H), 2.95 (m, 2H), 3.71 (s, 3H), 3.78 (t, 2H, J=5.6 Hz), 3.94 (s, 3H), 3.97 (m, 2H), 4.15 (t, 2H, J=5.6 Hz), 4.71 (4.80, s, 2H), 6.46–6.54 (m, 3H), 7.12 (t, 1H, J=8.0 Hz), 7.66 (d, 1H, J=8.4 Hz), 7.83 (m, 1H), 8.12 (m, 1H, J=1.2 Hz);

2-(5-guanidino-1H-benzoimidazol-2-ylmethyl)-N-(3-phenylpropyl)-1H-benzoimidazole-5-carboxamide (Compound 137), 2-(5-guanidino-1H-benzoimidazol-2-ylmethyl)-3-(3-hydroxy)propyl-N-(2-naphth-1-ylethyl)-3H-benzoimidazole-5-carboxamide (Compound 138), $^1$H-NMR (300 Mhz, CD$_3$OD): 2.09 (m, 2H), 3.44 (t, 2H, J=7.4 Hz), 3.58 (t, 2H, J=5.6 Hz), 3.77 (t, 2H, J=7.4 Hz), 4.55 (t, 2H, J=7.1 Hz), 7.32 (dd, 1H, J=8.6,1.9 Hz), 7.37–7.55 (m, 4H), 7.61 (d, 1H, J=1.9 Hz), 7.69 (d, 1H, J=8.4 Hz), 7.73–7.88 (m, 4H), 8.11 (s, 1H), 8.28 (d, 1H, J=8.1 Hz);

2-(5-guanidino-1H-benzoimidazol-2-ylmethyl)-3-(2,3-dihydroxy)propyl-N-[2-(2-methoxy)phenoxyethyl]-3H-benzoimidazole-5-carboxamide (Compound 139), MS (BioIon) C$_{29}$H$_{32}$N$_8$O$_5$ m/e calc 572.62; found 573.3 (MH$^+$); $^1$H-NMR (300 Mhz, CD$_3$OD): 3.58-3.69 (m, 2H), 3.80 (m, 5H), 4.07 (m, 1H), 4.17 (t, 2H, J=5.3 Hz), 4.47 (dd, 1H, J=15.0, 8.4 Hz), 4.64 dd, 1H, J=15.0, 3.0 Hz), 6.66–7.00 (m, 4H), 7.38 (dd, 1H, J=8.6,1.7 Hz), 7.66 (d, 1H, J=1.7 Hz), 7.70 (d, 1H, J=8.6 Hz), 7.78 (d, 1H, J=8.6 Hz), 7.87 (d, 1H, J=8.6,1.5 Hz), 8.24 (d, 1H, J=1.5 Hz);

2-[1-(5-guanidino-1H-benzoimidazol-2-yl)ethyl]-3-(2,3-dihydroxypropyl)-N-(2-naphth-1-ylethyl)-3H-benzoimidazole-5-carboxamide (Compound 140), MS (BioIon) $C_{33}H_{34}N_8O_3$ m/e calc 590.7; found 591.3 (MH$^+$);

2-(5-guanidino-1H-benzoimidazol-2-ylcarbonyl)-3-(2,3-dihydroxypropyl)-N-[2-(2-methoxyphenoxy)ethyl]-3H-benzoimidazole-5-carboxamide (Compound 141), MS (BioIon) $C_{29}H_{30}N_8O_6$ m/e calc 586.6; found 587.5 (MH$^+$); $^1$H-NMR (300 Mhz, CD$_3$OD): 3.33 (m, 1H), 3.81 (m, 5H), 3.98 (d, 2H, J=4.5 Hz), 4.18 (t, 2H, J=5.4 Hz), 4.38 (t, 1H, J=12.0 Hz), 4.57 (dd, 1H, J=12.0, 3.5 Hz), 6.85–7.00 (m, 4H), 7.30 (dd, 1H, J=8.7, 2.2 Hz), 7.60 (d, 1H, J=2.2 Hz), 7.64 (d, 1H, J=8.4 Hz), 7.74 (d, 1H, J=8.7 Hz), 7.80 (dd, 1H, J=8.4,1.5 Hz), 8.14 (d, 1H, J=1.5 Hz);

2-[5-(1-iminoethyl)aminomethyl-1H-benzoimidazol-2-ylmethyl]-3-(2,3-dihydroxy)propyl—N-[2-(2-methoxy)phenoxyethyl]-3H-benzoimidazole-5-carboxamide (Compound 142), $^1$H-NMR (300 Mhz, CD$_3$OD): 2.28 (s, 3H), 3.64 (m, 2H), 3.80 (s, 3H), 3.79–3.85 (m, 2H), 4.05 (m, 1H), 4.18 (t, 2H, J=5.4 Hz), 4.46 (dd, 1H, J=15.0, 8.7 Hz), 4.62–4.66 (m 3H), 6.86–7.00 (m, 4H), 7.53 (dd, 1H, J=8.7,1.2 Hz), 7.68 (d, 1H, J=8.4 Hz), 7.77–7.80 (m, 2H), 7.84 (dd, 1H, J=8.4,1.4 Hz), 8.21 (d, 1H, J=1.4 Hz);

methyl 2-{2-[2-(5-guanidino-1H-benzoimidazol-2-ylmethyl)-3-methyl-3H-benzoimidazol-5-ylcarbonylamino]ethoxy}benzoate (Compound 143), MS (BioIon) $C_{28}H_{28}N_8O_4$ m/e calc 54.56; found 541.4 (MH$^+$);

2-{-2-[2-(5-guanidino-1H-benzoimidazol-2-ylmethyl)-3-methyl-3H-benzoimidazol-5-ylcarbonylamino]ethoxy}benzoic acid (Compound 144);

methyl 3-{-2-[2-(5-guanidino-1H-benzoimidazol-2-ylmethyl)-3-methyl-3H-benzoimidazol-5-ylcarbonylamino]ethoxy}benzoate (Compound 145), MS (BioIon) $C_{28}H_{28}N_8O_4$ m/e calc 540.5; found 541.4 (MH$^+$);

2-(5-guanidino-1H-benzoimidazol-2-ylmethyl)-3-methyl-N-[2-(2,6-dimethoxy)phenoxyethyl]-3H-benzoimidazole-5-carboxamide (Compound 146), $^1$H-NMR (300 Mhz, CD$_3$OD): 3.71 (t, 2H, J=5.3 Hz), 3.73 (s, 6H), 4.01 (s, 3H), 4.13 (t, 2H, J=5.3 Hz), 6.63 (d, 2H, J=8.4 Hz), 6.99 (t, 1H, J=8.4 Hz), 7.33 (dd, 1H, J=8.6,1.9 Hz), 7.63 (d, 1H, J=1.9 Hz), 7.74 (d, 1H, J=8.7 Hz), 7.75 (d, 1H, J=8.6 Hz), 7.90 (dd, 1H, J=8.7,1.5 Hz), 8.21 (d, 1H, J=1.5 Hz);

2-(5-guanidinomethyl-1H-benzoimidazol-2-ylmethyl)-3-(2,3-dihydroxy)propyl-N-[2-(2-methoxyphenoxy)ethyl]-3H-benzoimidazole-5-carboxamide (Compound 147), $^1$H-NMR (300 Mhz, CD$_3$OD): 3.57–3.69 (m, 2H), 3.80 (m, 5H), 4.05 (m, 1H), 4.17 (t, 2H, J=5.4 Hz), 4.45 (dd, 1H, J=15.0, 8.7 Hz), 4.58–4.65 (m, 3H), 6.85–7.00 (m, 4H), 7.50 (dd, 1H, J=8.7,1.5 Hz), 7.67 (d, 1H, J=8.5 Hz), 7.72 (d, 1H, J=1.5 Hz), 7.76 (d, 1H, J=8.7 Hz), 7.82 (dd, 1H, J=8.5,1.4 Hz), 8.19 (d, 1H, J=1.4 Hz);

2-(5-iminomethylaminomethyl-1H-benzoimidazol-2-ylmethyl)-3-(2,3-dihydroxy)propyl-N-[2-(2-methoxy)phenoxyethyl]-3H-benzoimidazole-5-carboxamide (Compound 148),$^1$H-NMR (300 Mhz, CD$_3$OD): 3.58–3.70 (m, 2H), 3.81 (m, 5H), 4.06 (m, 1H), 4.19 (t, 2H, J=5.4 Hz), 4.46 (dd, 1H, J=15.0, 8.7 Hz), 4.64 (dd, 1H, J=15.0, 3.0 Hz), 4.69 (4.73, s, 2H), 6.86–7.01 (m, 4H), 7.51 (dd, 1H, J=8.1,1.5 Hz), 7.69 (d, 1H, J=8.6 Hz), 7.76–7.79 (m, 2H), 7.84 (dd, 1H, J=8.6,1.3 Hz), 7.96 (8.12, s, 1H), 8.21 (d, 1H, J=1.3 Hz);

2-(5-guanidino-1H-benzoimidazol-2-ylmethyl)-3-methyl-N-(2-hydroxy-2-quinol-4-ylethyl)-3H-benzoimidazole-5-carboxamide (Compound 149), $^1$H-NMR (300 Mhz, CD$_3$OD): 3.60 (dd, 1H, J=13.8, 7.5 Hz), 3.97–4.06 (m, 4H), 5.99 (dd, 1H, J=7.5, 3.6 Hz), 7.35 (dd, 1H, J=8.7, 2.0 Hz), 7.65 (d, 1H, J=2.0 Hz), 7.69 (d, 1H, J=8.7 Hz), 7.77 (d, 1H, J=8.7 Hz), 7.84 (dd, 1H, J=8.7,1.5 Hz), 7.99 (m, 1H), 8.11–8.18 (m, 2H), 8.26 (d, 1H, J=8.4 Hz), 8.33 (d, 1H, J=5.7 Hz), 8.88 (d, 1H, J=8.7 Hz), 8.15 (d, 1H, J=5.7 Hz);

2-(5-guanidino-1H-benzoimidazol-2-ylmethyl)-3-methyl-N-[2-(3-methyl-2,4-dioxoquinazolin-1-yl)ethyl]-3H-benzoimidazole-5-carboxamide (Compound 150), MS (BioIon) $C_{29}H_{28}N_{10}O_3$ m/e calc 564.6; found 565.5 (MH$^+$);

methyl 2-{2-[2-(5-guanidino-1H-benzoimidazol-2-ylcarbonyl)-3-methyl-3H-benzoimidazol-5-ylcarbonylamino]ethoxy}benzoate (Compound 151), MS (BioIon) $C_{28}H_{26}N_8O_5$ m/e calc 554.5; found 554.8 (MH$^+$);

2-(5-guanidino-1H-benzoimidazol-2-ylmethyl)-3-(2-hydroxy)ethyl-N-(2-naphth-1-ylethyl)-3H-benzoimidazole-5-carboxamide (Compound 152), 1H-NMR (300 Mhz, CD$_3$OD): 3.44 (t, 2H, J=7.4 Hz), 3.77 (t, 2H, J=7.4 Hz), 3.95 (t, 2H, J=4.9 Hz), 4.56 (t, 2H, J=4.9 Hz), 7.32 (dd, 1H, J=8.7,1.8 Hz), 7.40–7.54 (m, 4H), 7.61 (d, 1H, J=1.8 Hz), 7.67–7.89 (m, 5H), 8.09 (d, 1H, J=1.2 Hz), 8.28 (d, 1H, J=8.1 Hz);

2-(5-guanidino-1H-benzoimidazol-2-ylmethyl)-3-methyl-N-[2-(3-oxo-2,3-dihydrobenzo[1,4]oxazin-4-yl)ethyl]-3H-benzoimidazole-5-carboxamide (Compound 153);

2-(5-guanidino-1H-benzoimidazol-2-ylcarbonyl]-3-(2-hydroxyethyl)-N-(2-naphth-2-ylethyl)-3H-benzoimidazole-5-carboxamide (Compound 154), $^1$H-NMR (300 Mhz, CD$_3$OD): 3.42 (t, 2H, J=7.3 Hz), 3.75 (t, 2H, J=7.3 Hz), 4.48–4.51 (m, 2H), 7.29 (dd, 1H, J=8.6,1.9 Hz), 7.38–7.52 (m, 4H), 7.58 (d, 1H, J=1.9 Hz), 7.62 (d, 1H, J=8.7 Hz), 7.71–7.76 (m, 3H), 7.86 (d, 1H, J=8.6 Hz), 8.06 (s, 1H), 8.26 (d, 1H, J=8.1 Hz);

2-(5-guanidino-1H-benzoimidazol-2-ylcarbonyl)-3-methyl-N-(2-naphth-1-ylethyl)-3H-benzoimidazole-5-carboxamide (Compound 155), 2-(5-guanidino-1H-benzoimidazol-2-ylcarbonyl)-3-(3-hydroxypropyl)-N-(2-naphth-1-ylethyl)-3H-benzoimidazole-5-carboxamide (Compound 156);

2-(5-imidazol-1-yl-1H-benzoimidazol-2-ylmethyl)-3-methyl-N-(2-naphth-1-ylethyl)-3H-benzoimidazole-5-carboxamide (Compound 157);

2-[1-(5-guanidino-1H-benzoimidazol-2-yl)ethyl]-3-methyl-N-(2-naphth-1-ylethyl)-3H-benzoimidazole-5-carboxamide (Compound 158), MS (BioIon) $C_{31}H_{30}N_8O_1$ m/e calc 530.6; found 531.1 (MH$^+$);

2-[1-(5-imidazol-1-yl-1H-benzoimidazol-2-yl)ethyl]-3-methyl-N-(2-naphth-1-ylethyl)-3H-benzoimidazole-5-carboxamide (Compound 159), MS (BioIon) $C_{33}H_{29}N_7O$, m/e calc 539.6; found 540.1 (MH$^+$);

2-{1-[5-(2-aminoimidazol-1-yl)-1H-benzoimidazol-2-yl]ethyl}-3-methyl-N-(2-naphth-1-ylethyl)-3H-benzoimidazole-5-carboxamide (Compound 160), MS (BioIon) $C_{33}H_{30}N_8O_1$ m/e calc 554.7; found 555.2 (MH$^+$);

1-(5-guanidino-1H-benzoimidazol-2-yl)-3-hydroxy-1-methyl-N-(2-naphth-1-ylethyl) 3,4-dihydro-1H-2-oxa-4a,9-diazafluorene-6-carboxamide (Compound 161);

2-[1-(5-guanidino-1H-benzoimidazol-2-yl)ethyl]-3-(4-hydroxybutyl)-N-(2-naphth-1-ylethyl)-3H-benzoimidazole-5-carboxamide (Compound 162), MS (BioIon) $C_{34}H_{36}N_8O_2$ m/e calc 588.7; found 589.3 (MH$^+$);

3-[2-[1-(5-guanidino-1H-benzoimidazol-2-yl)ethyl]-6-(2-naphth-1-ylethylcarbamoyl)benzoimidazol-1-yl]propane-1-sulfonic acid (Compound 163), MS (BioIon) $C_{33}H_{34}N_8O_4S$ m/e calc 638.7; found 639.2 (MH$^+$);

3-[2-[1-(5-imidazol-1-yl-1H-benzoimidazol-2-yl)ethyl]-6-(2-naphth-1-ylethylcarbamoyl)benzoimidazol-1-yl]propane-1-sulfonic acid (Compound 164), MS (BioIon) $C_{35}H_{33}N_7O_4S$ m/e calc 647.8; found 648.2 (MH$^+$);

2-[1-(5-guanidino-1H-benzoimidazol-2-yl)-2-methylpropyl]-3-methyl-N-(2-naphth-1-ylethyl)-3H-benzoimidazole-5-carboxamide (Compound 165), MS (BioIon) $C_{33}H_{34}N_8O_1$ m/e calc 558.7; found 559.6 (MH$^+$);

2-[1-(1H-imidazo[4,5-c]pyridin-2-yl)ethyl]-3-methyl-N-(2-naphth-1-ylethyl)-3H-benzoimidazole-5-carboxamide (Compound 166), MS (BioIon) $C_{29}H_{26}N_6O_1$ m/e calc 474.6; found 475.2 (MH$^+$);

2-{5-[1-(N-methylimino)ethyl]-4,5,6,7-tetrahydro-1H-imidazo[4,5-c]pyridin-2-ylmethyl}-3-methyl-N-(2-naphth-1-ylethyl)-3H-benzoimidazole-5-carboxamide (Compound 167), MS (BioIon) $C_{31}H_{33}N_7O$ m/e calc 519.71; found 520.9 (MH$^+$);

imino(2-{1-[1-methyl-6-(2-naphth-1-ylethylcarbamoyl)-1H-benzoimidazol-2-yl]ethyl}-1,4,6,7-tetrahydroimidazo[4,5-c]pyridin-5-yl)acetic acid (Compound 168), MS (BioIon) $C_{31}H_{31}N_7O_3$ m/e calc 549.6; found 550.2 (MH$^+$);

2-{1-[5-(1-iminoethyl)-4,5,6,7-tetrahydro-1H-imidazo[4,5-c]pyridin-2-yl]ethyl}-3-methyl-N-(2-naphth-1-ylethyl)-3H-benzoimidazole-5-carboxamide (Compound 169), MS (BioIon) $C_{31}H_{33}N_7O_1$ m/e calc 519.6; found 520.3 (MH$^+$);

2-{1-[5-(N-methylamidino)-4,5,6,7-tetrahydro-1H-imidazo[4,5-c]pyridin-2-yl]ethyl}-3-methyl-N-(2-naphth-1-ylethyl)-3H-benzoimidazole-5-carboxamide (Compound 170), MS (BioIon) $C_{31}H_{34}N_8O_1$ m/e calc 534.7; found 535.1 (MH$^+$);

2-(2-{2-[1-(5-guanidino-1H-benzoimidazol-2-yl)ethyl]-3-methyl-3H-benzoimidazol-5-ylcarbonylamino}ethoxy)-5-methoxybenzoic acid (Compound 171), MS (BioIon) $C_{29}H_{30}N_8O_5$ m/e calc 570.6; found 571.2 (MH$^+$);

2-(2-{2-[1-(5-guanidino-1H-benzoimidazol-2-yl)ethyl]-3-methyl-3H-benzoimidazol-5-ylcarbonylamino}ethoxy)isophthalic acid (Compound 172), MS (BioIon) $C_{29}H_{30}N_8O_5$ m/e calc 570.6; found 571.3 (MH$^+$);

2-(2-{2-[1-(5-guanidino-1H-benzoimidazol-2-yl)-1-hydroxyethyl]-3-methyl-3H-benzoimidazol-5-ylcarbonylamino}ethoxy)-6-methoxybenzoic acid (Compound 173), MS (BioIon) $C_{29}H_{30}N_8O_6$ m/e calc 586.6; found 587.2 (MH$^+$);

ethyl 2-[2-(2-{1-[5-(N-acetylguanidino)-1H-benzoimidazol-2-yl]ethyl}-3-methyl-3H-benzoimidazol-5-ylcarbonylamino)ethoxy]benzoate (Compound 174), MS (BioIon) $C_{31}H_{32}N_8O_5$ m/e calc 596.6; found 597.2 (MH$^+$);

2-{-[5-(N,N-dimethylamidino)-4,5,6,7-tetrahydro-1H-imidazo[4,5-c]-pyridin-2-ylethyl}-3-methyl-N-(2-naphth-1-ylethyl)-3H-benzoimidazole-5-carboxamide (Compound 175);

2-{1-[5-(2-amino-1,1-dimethylethyl)-1H-benzoimidazol-2-yl]ethyl}-3-methyl-N-(2-naphth-1-ylethyl)-3H-benzoimidazole-5-carboxamide (Compound 176);

2-{1-[5-(1-iminoethyl)-4,5,6,7-tetrahydro-1H-imidazo[4,5-c]pyridin-2-yl]ethyl}—N-ethyl-3-methyl-3H-benzoimidazole-5-carboxamide (Compound 177);

2-[2-(2-{1-[5-(N-acetylguanidino)-1H-benzoimidazol-2-yl]ethyl}-3-methyl-3H-benzoimidazol-5-ylcarbonylamino)ethoxy]benzoic acid (Compound 178), MS (BioIon) $C_{30}H_{30}N_8O_5$ m/e calc 582.6; found 583.3 (MH$^+$);

2-[2-(2-{1-[5-(1-aminocyclopropyl)-1H-benzoimidazol-2-yl]ethyl}-3-methyl-3H-benzoimidazol-5-ylcarbonylamino)ethoxy]benzoic acid (Compound 179), MS (BioIon) $C_{31}H_{30}N_6O_4$ m/e calc 538.6; found 539.3 (MH$^+$);

2-[1-(5-imidazol-1-yl-1H-benzoimidazol-2-yl)ethyl]-3-methyl-N-(3-methylbutyl)-3H-benzoimidazole-5-carboxamide (Compound 180), MS (BioIon) $C_{26}H_{29}N_7O_1$ m/e calc 455.6; found 456.2 (MH$^+$);

2-(1H-benzoimidazol-2-ylethyl)-3-methyl-N-(2-phenoxyethyl)-3H-benzoimidazole-5-carboxamide (Compound 181), MS (BioIon) $C_{26}H_{25}N_5O_2$ m/e calc 439.5; found 440.2 (MH$^+$);

ethyl 2-[2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)ethoxy]benzoate (Compound 182);

2-[1-(5-guanidino-1H-benzoimidazol-2-yl)ethyl]-3-methyl-N-[2-(2,4-dioxo-3,4-dihydro-2H-quinazolin-1-yl)ethyl]-3H-benzoimidazole-5-carboxamide (Compound 183);

2-{1-[5-(1-iminoethyl)-4,5,6,7-tetrahydro-1H-imidazo[4,5-c]pyridin-2-yl]ethyl}-N-(3-methoxypropyl)-3-methyl-3H-benzoimidazole-5-carboxamide (Compound 184);

N-ethyl-2-[1-(5-imidazol-1-yl-1H-benzoimidazol-2-yl)ethyl]-3-methyl-3H-benzoimidazole-5-carboxamide (Compound 185), MS (BioIon) $C_{23}H_{23}N_7O_1$ m/e calc 413.5; found 414.1 (MH$^+$);

2-[1-(5-imidazol-1-yl-1H-benzoimidazol-2-yl)ethyl]-N-(2-methoxyethyl)-3-methyl-3H-benzoimidazole-5-carboxamide (Compound 186), MS (BioIon) $C_{24}H_{25}N_7O_2$ m/e calc 443.5; found 444.2 (MH$^+$);

1-(2-[1-(5-imidazol-1-yl-1H-benzoimidazol-2-yl)ethyl]-3-methyl-3H-benzoimidazol-5-ylcarbonylamino)-4-methylpentanoic acid (Compound 187), MS (BioIon) $C_{27}H_{29}N_7O_3$ m/e calc 499.6; found 500.3 (MH$^+$);

2-(2-{2-[1-(5-imidazol-1-yl-1H-benzoimidazol-2-yl)ethyl]-3-methyl-3H-benzoimidazol-5-ylcarbonylamino}ethoxy)benzoic acid (Compound 188), MS (BioIon) $C_{30}H_{27}N_7O_4$ m/e calc 549.6; found 550.2 (MH$^+$);

2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)-4-methylpentanoic acid (Compound 189);

2-{1-[5-(N,N-dimethylamidino)-4,5,6,7-tetrahydro-1H-imidazo[4,5-c]pyridin-2-yl]ethyl)-3-methyl-3H-benzoimidazol-5-ylcarbonylamino)ethoxy]benzoic acid (Compound 190), MS (BioIon) $C_{39}H_{34}N_8O_4$ m/e calc 558.6; found 559.3 (MH$^+$);

2-[2-(2-{1-[5-(2-carboxy-1-iminoethyl)-4,5,6,7-tetrahydro-1H-imidazo[4,5-c]pyridin-2-yl]ethyl}-3-methyl-3H-benzoimidazol-5-ylcarbonylamino)ethoxy]benzoic acid (Compound 181), MS (BioIon) $C_{29}H_{31}N_7O_6$ m/e calc 573.6; found 530.3 (MH$^+$), loss of $CO_2$;

2-(2-{2-[1-(5-imidazol-1-yl-1H-benzoimidazol-2-yl)ethyl]-3-(2-methoxyethyl)-3H-benzoimidazol-5-ylcarbonylamino}ethoxy)benzoic acid (Compound 192), MS (BioIon) $C_{32}H_{31}N_7O_5$ m/e calc 593.6; found 594.2 (MH$^+$);

2-[1-(5-imidazol-1-yl-1H-benzoimidazol-2-yl)ethyl]-3-(2-methoxyethyl)-N-(2-methoxyethyl)-3H-benzoimidazole-5-carboxamide (Compound 193), MS (BioIon) $C_{26}H_{29}N_7O_3$ m/e calc 487.6; found 488.2 (MH$^+$);

2-[2-(2-{1-[5-(1-iminoethyl)-4,5,6,7-tetrahydro-1H-imidazo [4,5-c]pyridin-2-yl]ethyl)-3-(2-methoxyethyl)-3H-benzoimidazol-5-ylcarbonylamino)ethoxy]benzoic acid (Compound 194);

3-(2-{2-[1-(5-guanidino-1H-benzoimidazol-2-yl)ethyl]-3-methyl-3H-benzoimidazol-5-ylcarbonylamino}ethoxy)benzoic acid (Compound 185), MS (BioIon) $C_{28}H_{28}N_8O_4$ m/e calc 540.6; found 541.3 (MH$^+$);

2-(2-{2-[1-(5-guanidino-1H-benzoimidazol-2-yl)ethyl]-3-(2-methoxyethyl)-3H-benzoimidazol-5-ylcarbonylamino}ethoxy)benzoic acid (Compound 196), MS (BioIon) $C_{30}H_{32}N8O_5$ m/e calc 584.6; found 585.3 (MH$^+$);

2-(2-{2-[1-(5-guanidino-1H-benzoimidazol-2-yl)ethyl]-3-(3-sulfopropyl)-3H-benzoimidazol-5-ylcarbonylamino}ethoxy)benzoic acid (Compound 197), MS (BioIon) $C_{30}H_{32}N_8O_7S$ m/e calc 648.7; found 649.6 (MH$^+$);

2-(2-{2-[1-(5-imidazol-1-yl-1H-benzoimidazol-2-yl)ethyl]-3-(3-sulfopropyl)-3H-benzoimidazol-5-ylcarbonylamino}ethoxy)benzoic acid (Compound 198), MS (BioIon) $C_{32}H_{31}N_7O_7S$ m/e calc 657.7; found 658.4 (MH$^+$);

2-(2-{2-[1-(5-imidazol-1-yl-3-methyl-3H-benzoimidazol-2-yl)ethyl]-3-methyl-3H-benzoimidazol-5-ylcarbonylamino}ethoxy)benzoic acid (Compound 199), MS (BioIon) $C_{31}H_{29}N_7O_4$ m/e calc 563.6; found 564.2 (MH$^+$);

2-(2-{2-[1-(5-imidazol-1-yl-1H-benzoimidazol-2-yl)ethyl]-3-(2-hydroxypropyl)-3H-benzoimidazol-5-ylcarbonylamino}ethoxy)benzoic acid (Compound 200), MS (BioIon) $C_{32}H_{31}N_7O_5$ m/e calc 593.6; found 594.3 (MH$^+$);

2-{2-[2-(1-{5-[1-(N-hydroxyimino)ethyl]-4,5,6,7-tetrahydro-1H-imidazo[4,5-c]pyridin-2-yl}ethyl)-3-methyl-3H-benzoimidazol-5-ylcarbonylamino]ethoxy}benzoic acid (Compound 201);

ethyl 2-(2-{2-[1-(5-guanidino-1H-benzoimidazol-2-yl)ethyl]-3-methyl-3H-benzoimidazol-5-ylcarbonylamino}ethoxy)benzoate (Compound 202), MS (BioIon) $C_{31}H_{32}N_8O_4$ m/e calc 568.6; found 569.5 (MH$^+$);

ethyl 2-[2-(2-{1-[5-(1-iminoethyl)-4,5,6,7-tetrahydro-1H-imidazo[4,5-c]pyridin-2-yl]ethyl}-1,4,6,7-tetrahydroimidazo[4,5-c]pyridin-5-ylcarbonylamino)ethoxy]benzoate (Compound 203), MS (BioIon) $C_{28}H_{36}N_8O_4$ m/e calc 549.0; found 548.2 (MH$^+$);

ethyl 4-{2-[1-(5-guanidino-1H-benzoimidazol-2-yl)ethyl]-3-methyl-3H-benzoimidazol-5-ylcarbonylamino}butyrate (Compound 204), MS (BioIon) $C_{25}H_{30}N_8O_3$ m/e calc 490.57; found 491.3 (MH$^+$);

2-[1-(5-guanidino-1H-benzoimidazol-2-yl)ethyl]-3-methyl-N-[2-(2-tetrazol-1-ylphenoxy)ethyl)-3H-benzoimidazole-5-carboxamide (Compound 205), MS (BioIon) $C_{28}H_{28}N_{12}O_2$ m/e calc 564.56; found 565.3 (MH$^+$);

2-[2-(2-{1-[5-(1-iminoethylamino)-1H-benzoimidazol-2-yl]ethyl}-3-methyl-3H-benzoimidazol-5-ylcarbonylamino)ethoxy]benzoic acid (Compound 206), MS (BioIon) $C_{31}H_{33}N_7O_4$ m/e calc 567.6; found 568.4 (MH$^+$);

ethyl 4-(2-{2-[1-(5-guanidino-1H-benzoimidazol-2-yl)ethyl]-3-methyl-3H-benzoimidazol-5-ylcarbonylamino}ethoxy)benzoate (Compound 207), MS (BioIon) $C_{30}H_{32}N_8O_4$ m/e calc 568.6; found 569.4 (MH$^+$);

5-(2-{2-[1-(5-guanidino-1H-benzoimidazol-2-yl)ethyl]-3-methyl-3H-benzoimidazol-5-ylcarbonylamino}ethoxy)isophthalic acid (Compound 208), MS (BioIon) $C_{29}H_{28}N_8O_6$ m/e calc 584.6; found 585.3 (MH$^+$);

4-(2-{2-[1-(5-guanidino-1H-benzoimidazol-2-yl)ethyl]-3-methyl-3H-benzoimidazol-5-ylcarbonylamino}ethoxy)benzoic acid (Compound 209), MS (BioIon) $C_{28}H_{28}N_8O_4$ m/e calc 540.6; found 541.2 (MH$^+$);

2-(2-{2-[1-(5-guanidino-1H-benzoimidazol-2-yl)ethyl]-3-(2-hydroxypropyl)-3H-benzoimidazol-5-ylcarbonylamino}ethoxy)benzoic acid (Compound 210), MS (BioIon) $C_{30}H_{32}N_8O_5$ m/e calc 584.6; found 585.4 (MH$^+$);

2-[1-(5-imidazol-1-yl-1H-benzoimidazol-2-yl)ethyl]-3-methyl-N-[2-(2-methoxyphenoxy)ethyl]-3H-benzoimidazole-5-carboxamide (Compound 211), MS (BioIon) $C_{31}H_{29}N_7O_2$ m/e calc 535.6; found 536.3 (MH$^+$);

2-(2-{2-[1-(5-guanidino-1H-benzoimidazol-2-yl)ethyl]-3-methyl-3H-benzoimidazol-5-ylcarbonylamino}ethoxy)benzoic acid (Compound 212), MS (BioIon) $C_{27}H_{26}N_8O_4$ m/e calc 526.6; found 527.2 (MH$^+$);

2-[1-(5-imidazol-1-yl-1H-benzoimidazol-2-yl)ethyl]-3-methyl-N-(2-phenoxyethyl)-3H-benzoimidazole-5-carboxamide (Compound 213), MS (BioIon) $C_{29}H_{27}N_7O_2$ m/e calc 505.6; found 506.2 (MH$^+$);

2-(2-{2-[1-(5-imidazol-1-yl-1H-benzoimidazol-2-yl)ethyl]-1H-benzoimidazol-5-ylcarbonylamino}ethoxy)benzoic acid (Compound 214), MS (BioIon) $C_{29}H_{25}N_7O_4$ m/e calc 535.6; found 536.4 (MH$^+$);

ethyl 2-(2-(2-[1-(5-guanidino-1H-benzoimidazol-2-yl)ethyl]-3-methyl-3H-benzoimidazol-5-ylcarbonylamino}ethoxy)-4-methylbenzoate (Compound 215), MS (BioIon) $C_{31}H_{34}N_8O_4$ m/e calc 582.7; found 583.5 (MH$^+$);

2-(2-{2-[1-(5-guanidino-1H-benzoimidazol-2-yl)ethyl]-3-methyl-benzoimidazol-5-ylcarbonylamino}ethoxy)-4-methylbenzoic acid (Compound 216), MS (BioIon) $C_{29}H_{30}N_8O_4$ m/e calc 554.6; found 555.5 (MH$^+$);

2-[2-(2-{1-[5-(1-iminoethyl)-4,5,6,7-tetrahydro-1H-imidazo[4,5-c]pyridin-2-yl]ethyl}-1,4,6,7-tetrahydroimidazo[4,5-c]pyridin-5-ylcarbonylamino)ethoxy]benzoate (Compound 217), MS (ESI) $C_{26}H_{32}N_8O_4$ m/e calc 520.58; found 521.3 (MH$^+$);

ethyl 2-(2-{2-[5-(N-methylamidino)-1H-benzoimidazol-2-ylmethyl]-3-methyl-3H-benzoimidazol-5-ylcarbonylamino}ethoxy)benzoate (Compound 218), MS (BioIon) $C_{30}H_{31}N_7O_4$ m/e calc 553.6; found 554.3 (MH$^+$);

2-[2-(2-{1-[5-(1-iminoethyl)-4,5,6,7-tetrahydro-1H-imidazo[4,5-c]pyridin-2-yl]ethyl}-3-(3-sulfopropyl)-3H-benzoimidazol-5-ylcarbonylamino)ethoxy]benzoic acid (Compound 219), MS (BioIon) $C_{31}H_{35}N_7O_7$ m/e calc 637.7; found 638.3 (MH$^+$);

ethyl 2-(2-{1-[5-(1-iminoethyl)-4,5,6,7-tetrahydro-1H-imidazo[4,5-c]pyridin-2-yl]ethyl}-3-methyl-3H-benzoimidazol-5-ylcarbonylamino)-4-methylvalerate (Compound 220);

ethyl 2-{2-[2-(1-{5-[1-(N-hydroxyimino)ethyl]-4,5,6,7-tetrahydro-1H-imidazo[4,5-c]pyridin-2-yl}ethyl)-3-methyl-3H-benzoimidazol-5-ylcarbonylamino]ethoxy}benzoate (Compound 221);

2-[1-(1H-benzoimidazol-2-yl)ethyl]-3-methyl-N-[2-(2-methoxyphenoxy)ethyl]-3H-benzoimidazole-5-carboxamide (Compound 222), MS (BioIon) $C_{27}H_{72}N_5O_3$ m/e calc 469.5; found 469.5 (MH$^+$);

2-(2-ethoxycarbonylphenoxy)ethyl 2-[1-(6-guanidino-1H-benzoimidazol-2-yl)ethyl]-1,4,6,7-tetrahydroimidazo[4,5-c]pyridine-5-carboxylate (Compound 223), MS (BioIon) $C_{28}H_{32}N_8O_5$ m/e calc 560.62; found 561.3 (MH$^+$);

4-{2-[1-(5-guanidino-1H-benzoimidazol-2-yl)ethyl]-3-methyl-3H-benzoimidazol-5-ylcarbonylamino}butyric acid (Compound 224), MS (BioIon) $C_{23}H_{26}N_8O_3$ m/e calc 462.52; found 462.8 (MH$^+$);

2-{1-[5-(1-iminoethyl)-4,5,6,7-tetrahydro-1H-imidazo[4,5-c]pyridin-2-yl]ethyl}-3-methyl-N-[2-(2-tetrazolylphenoxy)ethyl]-3H-benzoimidazole-5-carboxamide (Compound 225), MS (ESI) $C_{28}H_{31}N_{11}O_2$ m/e calc 553.6; found 553.5 (MH$^+$);

isopropyl 2-(2-{2-[1-(5-imidazol-1-yl-1H-benzoimidazol-2-yl)ethyl]-3-methyl-3H-benzoimidazol-5-ylcarbonylamino}ethoxy)benzoate (Compound 226), MS (BioIon) $C_{33}H_{33}N_7O_4$ m/e calc 591.3; found 591.4 (MH$^+$);

2-{1-[5-(1-iminoethyl)-4,5,6,7-tetrahydro-1H-imidazo[4,5-c]pyridin-2-yl]ethyl}-3-methyl-N-[2-(3-tetrazolylphenoxy)ethyl]-3H-benzoimidazole-5-carboxamide (Compound 227), MS (BioIon) $C_{28}H_{31}N_{11}O_2$ m/e calc 553.59; found 553.5 (MH$^+$);

2-{1-[5-(1-iminoethyl)-4,5,6,7-tetrahydro-1H-imidazo[4,5-c]pyridin-2-yl]ethyl}-3-methyl-N-[2-(4-tetrazolylphenoxy)ethyl]-3H-benzoimidazole-5-carboxamide (Compound 228), MS (ESI) $C_{28}H_{31}N_{11}O_2$ m/e calc 553.59; found 553.5 (MH$^+$);

cyclohexyl 2-(2-{2-[1-(5-imidazol-1-yl)-1H-benzoimidazol-2-yl]ethyl}-3-methyl-3H-benzoimidazol-5-ylcarbonylamino)ethoxybenzoate (Compound 229), MS (ESI) $C_{36}H_{37}N_7O_4$ m/e calc 631.3; found 631.5 (MH$^+$);

2-[2-(2-{1-[5-(N-methylamidino)-1H-benzoimidazol-2-yl]ethyl}-3-methyl-3H-benzoimidazol-5-ylcarbonylamino)ethoxy]benzoic acid (Compound 230), MS (BioIon) $C_{28}H_{27}N_7O_4$ m/e calc 525.6; found 525.5 (MH$^+$);

2-[2-(2-{1-[5-(1-iminoethylamino)-1H-benzoimidazol-2-yl]ethyl}-3-methyl-3H-benzoimidazol-5-ylcarbonylamino)ethoxy]benzoic acid (Compound 231), MS (BioIon) $C_{29}H_{29}N_7O_4$ m/e calc 539.6; found 539.8 (MH$^+$);

2-(3-{2-[1-(5-guanidino-1H-benzoimidazol-2-yl)ethyl]-1,4,6,7-tetrahydroimidazo[4,5-c]pyridin-5-ylcarbonyl}propoxy)benzoic acid (Compound 232), MS (BioIon) $C_{27}H_{30}N_8O_4$ m/e calc 530.60; found 531.7 (MH$^+$);

2-(2-{2-[1-(5-guanidino-1H-benzoimidazol-2-yl)ethyl]-1,4,6,7-tetrahydroimidazo[4,5-c]pyridin-5-ylformyloxy}ethoxy)benzoic acid (Compound 233), MS (BioIon) $C_{26}H_{28}N_8O_5$ m/e calc 532.56; found 533.2 (MH$^+$);

2-methoxyethyl 2-(2-{2-[1-(5-imidazol-1-yl-1H-benzoimidazol-2-yl)ethyl]-3-methyl-3H-benzoimidazol-5-ylcarbonylamino}ethoxy)benzoate (Compound 234), MS (BioIon) $C_{33}H_{33}N_7O_5$ m/e calc 607.3; found 607.4 (MH$^+$);

isobutyl 2-(2-{2-[1-(5-imidazol-1-yl-1H-benzoimidazol-2-yl)ethyl]-3-methyl-3H-benzoimidazol-5-ylcarbonylamino}ethoxy)benzoate (Compound 235), MS (BioIon) $C_{34}H_{35}N_7O_4$ m/e calc 605.3; found 605.4 (MH$^+$);

2-(2-methoxyethoxy)ethyl 2-(2-{2-[1-(5-imidazol-1-yl-1H-benzoimidazol-2-yl)ethyl]-3-methyl-3H-benzoimidazol-5-ylcarbonylamino}ethoxy)benzoate (Compound 236), MS (BioIon) $C_{35}H_{37}N_7O_6$ m/e calc 651.3; found 651.3 (MH$^+$);

butyl 2-(2-{2-[1-(5-imidazol-1-yl-1H-benzoimidazol-2-yl)ethyl]-3-methyl-3H-benzoimidazol-5-ylcarbonylamino}ethoxy)benzoate (Compound 237), MS (BioIon) $C_{34}H_{35}N_7O_4$ n/e calc 605.3; found 605.4 (MH$^+$);

2-[1-(1H-benzoimidazol-2-yl)ethyl]-3-methyl-N-[2-(3-oxo-2,3-dihydrobenzo[1,4]oxazin-4-yl)ethyl]-3H-benzoimidazole-5-carboxamide (Compound 238), MS (BioIon) $C_{28}H_{26}N_6O_3$ m/e calc 494.2; found 494.5 (MH$^+$);

2-[1-(1H-benzoimidazol-2-yl)ethyl]-3-methyl-N-[2-(2-fluorophenoxy)ethyl]-3H-benzoimidazole-5-carboxamide (Compound 239);

2-[1-(1H-benzoimidazol-2-yl)ethyl]-3-methyl-N-[2-(3-fluorophenoxy)ethyl]-3H-benzoimidazole-5-carboxamide (Compound 240);

2-[1-(1H-benzoimidazol-2-yl)ethyl]-3-methyl-N-[2-(2-isopropoxyphenoxy)ethyl]-3H-benzoimidazole-5-carboxamide (Compound 241), MS (BioIon) $C_{29}H_{31}N_5O_3$ m/e calc 497.2; found 497.6 (MH$^+$);

2-[1-(1H-benzoimidazol-2-yl)ethyl]-3-methyl-N-[2-(2-methylphenoxy)ethyl]-3H-benzoimidazole-5-carboxamide (Compound 242), MS (BioIon) $C_{27}H_{27}N_5O_2$ m/e calc 453.2; found 453.5 (MH$^+$);

2-[1-(1H-benzoimidazol-2-yl)ethyl]-3-methyl-N-[2-(2-ethoxyphenoxy)ethyl]-3H-benzoimidazole-5-carboxamide (Compound 243), MS (BioIon) $C_{28}H_{29}N_5O_3$ m/e calc 483.2; found 483.5 (MH$^+$);

2-[1-(5-guanidino-1H-benzoimidazol-2-yl)ethyl]-3-methyl-N-[2-(2-methoxyphenoxy)ethyl]-3H-benzoimidazole-5-carboxamide (Compound 244), MS (BioIon) $C_{28}H_{30}N_8O_3$ m/e calc 526.6; found 526.8 (MH$^+$);

ethyl 2-(2-{2-[1-(5-guanidino-1H-benzoimidazol-2-yl)ethyl]-1,4,6,7-tetrahydroimidazo[4,5-c]pyridin-5-ylcarbonylamino}ethoxy)benzoate (Compound 245), MS (BioIon) $C_{28}H_{33}N_9O_4$ m/e calc 559.6; found 559.6 (MH$^+$);

2-methoxyethyl 2-(2-{2-[1-(1H-benzoimidazol-2-yl)ethyl]-3-methyl-3H-benzoimidazol-5- ylcarbonylamino}ethoxy)benzoate (Compound 246), MS (BioIon) $C_{31}H_{31}N_5O_4$ m/e calc 541.6; found 541.5 (MH$^+$);

ethyl 2-{2-{2-[1-(5-guanidino-1H-benzoimidazol-2-yl)ethyl]-3-methyl-3H-benzoimidazol-5-ylcarbonylamino}ethoxy)benzoate (Compound 247), MS (BioIon) $C_{29}H_{30}N_8O_4$ m/e calc 554.6; found 555.4 (MH$^+$);

2-{2-{2-[1-(5-guanidino-1H-benzoimidazol-2-yl)ethyl]-3-methyl-3H-benzoimidazol-5-ylcarbonylamino}ethoxy)benzoic acid (Compound 248), MS (BioIon) $C_{28}H_{28}N_8O_4$ m/e calc 540.6; found 541.3 (MH$^+$);

2-[1-(5-guanidino-1H-benzoimidazol-2-yl)ethyl]-N-[2-(2-carbamoylphenoxy)ethyl]-3-methyl-3H-benzoimidazole-5-carboxamide (Compound 249), MS (BioIon) $C_{28}H_{29}N_9O_3$ m/e calc 539.6; found 540.5 (MH$^+$);

2-[1-(5-guanidino-1H-benzoimidazol-2-yl)ethyl]-N-[2-(2-carbamoyl-4-chlorophenoxy)ethyl]-3-methyl-3H-benzoimidazole-5-carboxamide (Compound 250), MS (BioIon) $C_{28}H_{28}N_9O_3Cl$ m/e calc 574.0; found 574.2 (MH$^+$);

4-chloro-2-(2-{2-[1-(5-guanidino-1H-benzoimidazol-2-yl)ethyl]-3-methyl-3H-benzoimidazol-5-ylcarbonylamino}ethoxy)benzoic acid (Compound 251), MS (BioIon) $C_{28}H_{27}N_8O_4Cl$ m/e calc 575.0 found 575.2 (MH$^+$);

5-chloro-2-(2-{2-[1-(5-guanidino-1H-benzoimidazol-2-yl)ethyl]-3-methyl-3H-benzoimidazol-5-ylcarbonylamino}ethoxy)benzoic acid (Compound 252), MS (BioIon) $C_{28}H_{27}N_8O_4Cl$ m/e calc 575.0; found 575.2 (MH$^+$);

6-chloro-2-(2-{2-[1-(5-guanidino-1H-benzoimidazol-2-yl)ethyl]-3-methyl-3H-benzoimidazol-5-ylcarbonylamino}ethoxy)benzoic acid (Compound 253), MS (BioIon) $C_{28}H_{27}N_8O_4Cl$ m/e calc 575.0; found 575.2 (MH$^+$);

4,6-dichloro-2-(2-{2-[1-(5-guanidino-1H-benzoimidazol-2-yl)ethyl]-3-methyl-3H-benzoimidazol-5-ylcarbonylamino}ethoxy)benzoic acid (Compound 254), MS (BioIon) $C_{28}H_{26}N_8O_4Cl_2$ m/e calc 609.5; found 609.1 (MH$^+$);

ethyl 2-(2-{2-[1-(1H-benzoimidazol-2-yl)ethyl]-3-methyl-3H-benzoimidazole-5-carbonylamino}ethoxy)benzoate (Compound 255), MS (BioIon) $C_{29}H_{29}N_5O_4$ m/e calc 511.6; found 512.2 (MH$^+$);

2-[1-(5-guanidino-1H-benzoimidazol-2-yl)ethyl]-3-methyl-N-{2-[2,4-dioxo-3-(2-trimethylsilanylethyl)-3,4-dihydro-2H-quinazolin-1-yl]ethyl}-3H-benzoimidazole-5-carboxamide (Compound 256), MS (BioIon) $C_{34}H_{40}N_{10}O_3Si$ m/e calc 664.8; found 665.4 (MH$^+$);

2-[1-(5-guanidino-1H-benzoimidazol-2-yl)ethyl]-3-methyl-N-{2-[2,4-dioxo-3,4-dihydro-2H-quinazolin-1-yl]ethyl}-3H-benzoimidazole-5-carboxamide (Compound 257), MS (BioIon) $C_{29}H_{28}N_{10}O_3$ m/e calc 564.6; found 565.2 (MH$^+$);

2-[1-(1H-benzoimidazol-2-yl)ethyl]-N-[2-(2-cyanophenoxy)ethyl]-3-methyl-3H-benzoimidazole-5-carboxamide (Compound 258), MS (BioIon) $C_{27}H_{24}N_6O_2$ m/e calc 454.5; found 465.1 (MH$^+$);

5-(2-{2-[1-(1H-benzoimidazol-2-yl)ethyl]-3-methyl-3H-benzoimidazol-5-ylcarbonylamino}ethoxy)isophthalic acid (Compound 259), MS (BioIon) $C_{28}H_{25}N_5O_6$ m/e calc 527.5; found 528.4 (MH$^+$);

2-(2-methoxyethoxy)ethyl 2-(2-{2-[1-(1H-benzoimidazol-2-yl)ethyl]-3-methyl-3H-benzoimidazol-5-ylcarbonylamino}ethoxy)benzoate (Compound 260), MS (BioIon) $C_{32}H_{35}N_5O_6$ m/e calc 585.7; found 585.4 (MH$^+$);

2-(2-{2-[1-(5-guanidino-1H-benzoimidazol-2-yl)ethyl]-1,4,6,7-tetrahydroimidazo[4,5-c]pyrid-5-ylcarbonylamino}ethoxy)benzoic acid (Compound 261), MS (BioIon) $C_{29}H_{29}N_9O_4$ m/e calc 531.6; found 531.5 (MH$^+$);

2-[1-(1H-imidazo[4,5-c]pyridin-2-yl)ethyl]-N-[2-(2-methoxyphenoxy)ethyl]-3-methyl-3H-benzoimidazole-5-carboxamide (Compound 262), MS (BioIon) $C_{26}H_{26}N_6O_3$ m/e calc 470.54; found 471.4 (MH$^+$);

2-[1-(5-fluoro-1H-benzoimidazol-2-yl)ethyl]-N-[2-(2-methoxyphenoxy)ethyl]-3-methyl-3H-benzoimidazole-5-carboxamide (Compound 263), MS (BioIon) $C_{27}H_{26}N_5O_3F$ m/e calc 487.54; found 488.1 (MH$^+$);

2-[1-(5-imidazol-1-yl-1H-benzoimidazol-2-yl)ethyl]-3-methyl-N-(2-tetrazol-1-ylethyl)-3H-benzoimidazole-5-carboxamide (Compound 264), MS (ESI) $C_{24}H_{23}N_{11}O$ m/e calc 481.47; found 482.6 (MH$^+$);

2-[1-(4-hydroxy-1H-benzoimidazol-2-yl)ethyl]-N-[2-(2-methoxyphenoxy)ethyl]-3-methyl-3H-benzoimidazole-5-carboxamide (Compound 265), MS (BioIon) $C_{27}H_{27}N_5O_4$ m/e calc 485.59; found 486.3 (MH$^+$);

2-[1-(4-aminobenzoxazol-2-yl)ethyl]-N-[2-(2-methoxyphenoxy)ethyl]-3-methyl-3H-benzoimidazole-5-carboxamide (Compound 266), MS (BioIon) $C_{27}H_{27}N_5O_4$ m/e calc 485.59; found 486.1 (MH$^+$);

3-{2-[1-(1H-benzoimidazol-2-yl)ethyl]-6-[2-(2-methoxyphenoxy)ethylcarbamoyl]benzoimidazol-1-yl}propane-1-sulfonic acid (Compound 267), MS (BioIon) $C_{29}H_{31}N_5O_6S$ m/e calc 577.66; found 577.4 (MH$^+$);

3-{2-[1-(5-imidazol-1-yl-1H-benzoimidazol-2-yl)ethyl]-6-[2-(2-methoxyphenoxy)ethylcarbamoyl]benzoimidazol-1-yl}propane-1-sulfonic acid (Compound 268), MS (BioIon) $C_{32}H_{33}N_7O_6S$ m/e calc 643.72; found 644.6 (MH$^+$);

ethyl 2-[2-(2-{1-[1-(2-methoxyethyl)-1H-benzoimidazol-2-yl]ethyl}-3-methyl-3H-benzoimidazole-5-carbonylamino)ethoxy]benzoate (Compound 269), MS (BioIon) $C_{32}H_{35}N_5O_5$ m/e calc 569.66; found 570.5 (MH$^+$);

benzyl 2-[1-(5-imidazol-1-yl-1H-benzoimidazol-2-yl)ethyl]-1,4,6,7-tetrahydroimidazo[4,5-c]pyridine-5-carboxylate (Compound 270), MS (BioIon) $C_{29}H_{30}N_8O_6$ m/e calc 586.6; found 587.2 (MH$^+$);

ethyl 2-(4-{2-[1-(1H-benzoimidazol-2-yl)ethyl]-1,4,6,7-tetrahydroimidazo[4,5-c]pyridin-5-yl}-4-oxobutoxy)benzoate (Compound 271);

1-{2-[1-(1H-benzoimidazol-2-yl)ethyl]-1,4,6,7-tetrahydroimidazo[4,5-c]pyridin-5-yl}-4-(2-methoxyphenoxy)butan-1-one (Compound 272);

2-(5-guanidino-1H-benzoimidazol-2-ylmethyl)-N-(2-naphth-1-ylethyl)imidazo[1,2-a]pyridine-6-carboxamide (Compound 273);

N-[3-(2-ethoxyphenyl)propyl]-2-[1-(5-hydroxy-1H-benzoimidazol-2-yl)ethyl]-3-methyl-3H-benzoimidazole-5-carboxamide (Compound 274), MS (BioIon) $C_{29}H_{31}N_5O_3$ m/e calc 497.62; found 497.4;

N-[3-(2-butoxyphenyl)propyl]-2-[1-(5-hydroxy-1H-benzoimidazol-2-yl)ethyl]-3-methyl-3H-benzoimidazole-5-carboxamide (Compound 275), MS (BioIon) $C_{31}H_{35}N_5O_3$ m/e calc 525.65; found 526.3;

2-[1-(5-hydroxy-1H-benzoimidazol-2-yl)ethyl]-3-methyl-N-[3-(2-propoxyphenyl)propyl]-3H-benzoimidazole-5-carboxamide (Compound 276), MS (BioIon) $C_{31}H_{33}N_5O_3$ m/e calc 511.62; found 512.3;

2-[1-(5-hydroxy-1H-benzoimidazol-2-yl)ethyl]-N-{2-[2-(3-methyl-[1,2,4]oxadiazol-5-yl)phenoxy]ethyl}-3-methyl-3H-benzoimidazole-5-carboxamide (Compound 277), MS (BioIon) $C_{29}H_{27}N_7O_4$ m/e calc 538.1; found 537.58;

ethyl 2-(2-{2-[1-(4-fluoro-5-hydroxy-1H-benzoimidazol-2-yl)ethyl]-3-methyl-3H-benzoimidazol-5-ylcarbonylamino}ethoxy)benzoate (Compound 278), MS (ESI) $C_{29}H_{28}N_5O_5$ m/e calc 545.57 found 545.6;

2-(2-{2-[1-(4-fluoro-5-hydroxy-1H-benzoimidazol-2-yl)ethyl]-3-methyl-3H-benzoimidazol-5-ylcarbonylamino}ethoxy)benzoic acid (Compound 279), MS (BioIon) $C_{27}H_{24}N_5O_5F$ m/e calc 517.52 found 517.4;

ethyl 2-(2-{2-[1-(6-fluoro-4-hydroxy-1H-benzoimidazol-2-yl)ethyl]-3-methyl-3H-benzoimidazol-5-ylcarbonylamino}ethoxy)benzoate (Compound 280), MS (BioIon) $C_{29}H_{28}N_5O_5F$ m/e calc 545.57 found 545.9;

2-(2-{2-[1-(6-fluoro-4-hydroxy-1H-benzoimidazol-2-yl)ethyl]-3-methyl-3H-benzoimidazol-5-ylcarbonylamino}ethoxy)benzoic acid (Compound 280), MS (BioIon) $C_{27}H_{24}N_{50}O_5F$ m/e calc 517.52 found 517.6;

ethyl 2-(2-{2-[1-(4,5-difluoro-7-hydroxy-1H-benzoimidazol-2-yl)ethyl]-3-methyl-3H-benzoimidazol-5-ylcarbonylamino}ethoxy)benzoate (Compound 281), MS (BioIon) $C_{29}H_{27}N_5O_5F_2$ m/e calc 563.56 found 563.9; and 2-(2-{2-[1-(4,5-difluoro-7-hydroxy-1H-benzoimidazol-2-yl)ethyl]-3-methyl-3H-benzoimidazol-5-ylcarbonylamino}ethoxy)benzoic acid (Compound 282), MS (ESI) $C_{29}H_{27}N_5O_5F_2$ m/e calc 536.1 found 535.51.

Example 13

In vitro Tryptase Inhibition Assay

Tryptase solution (60 g/mL) was prepared by dissolving tryptase purified from human lung or skin tissue preparations or human mast cell line (HMC-1) or obtained from commercial sources, e.g., ICN Biomeidals, Irvine, Calif., Athens Research & Technology, Athens, Ga., etc., in a solvent mixture comprising: 10 mM 2-N-morpholinoethane sulfonic acid, 2 mM $CaCl_2$, 20% glycerol and 50 g/mL heparin. Substrate solution containing 2 mM synthetic tripeptide (tosyl-Gly-Pro-Lys-p-nitroanilide) was obtained from Sigma. Test Compound solutions were prepared by diluting a stock solution (1 mg of test Compound in 200 µL of dimethylsulfoxide (DMSO)) by ten-fold into assay buffer (comprising: Tris-HCl (pH 8.2), 50 mM; NaCl, 100 MM; 0.05% polyoxyethylenesorbitan monolaurate (Tween-20®); and zinc chloride, 150 µM) and then making seven additional three-fold dilutions into 10% DMSO in assay buffer.

Aliquots (50 µL) from each of the eight dilutions of test compound solution were added to separate wells in a 96-well U-bottom microtiter plate. Typtase solution (25 µL) was added to each well and the solutions were mixed 1 hour at room temperature. Substrate solution (25 µL) was added to initiate the enzymatic reaction and the microtiter plates were immediately transferred to a UVIMAX Kinetic Microplate Reader (Molecular Devices). The hydrolysis of the chromogenic substrate was followed spectrophotometrically at 405 nanometers for five minutes. Initial velocity measurements were calculated from the progress curves by kinetic analysis program (BatchKi; Petr Kuzmic, University of Wisconsin, Madison, Wis.). Apparent inhibition constants (K) were calculated from the enzyme progress curves using standard mathematical models.

Proceeding as described in this application or by methods known to those of ordinary skill the following compounds of the invention were tested for tryptase inhibitory activity:

Compound 1, $K_i$=0.09 µM; Compound 12, $K_i$=29 µM; Compound 26, $K_i$=33 µM; Compound 27, $K_i$=0.6 µM; Compound 28, $K_i$=0.00007 µM; Compound 29, $K_i$=0.0008 µM; Compound 30, $K_i$=0.009 µM; Compound 37, $K_i$=0.002 µM; Compound 42, $K_i$=0.008 µM; Compound 43, $K_i$=0.002 µM; Compound 74, $K_i$=0.006 µM; Compound 75, $K_i$=0.03 µM; Compound 80, $K_i$=0.01 µM; Compound 81, $K_i$=0.01 µM; Compound 84, $K_i$=2.6 µM; Compound 102, $K_i$=0.00007 µM; Compound 112, $K_i$=0.00005 µM; Compound 115, $K_i$=0.003 µM; Compound 116, $K_i$=0.006 µM; Compound 117, $K_i$=0.008 µM; Compound 126, $K_i$=0.008 µM; Compound 127, $K_i$=0.006 µM; Compound 128, $K_i$=0.002 µM; Compound 169, $K_i$=0.001 µM; Compound 132, $K_i$=0.00002 µM; Compound 134, $K_i$=0.00002 µM; Compound 138, $K_i$=0.0002 µM; Compound 152, $K_i$=0.0005 µM; Compound 182, $K_i$=0.004 µM; Compound 194, $K_i$=0.009 µM; Compound 203, $K_i$0.008 µM; Compound 225, $K_i$=0.008 µM; Compound 249, $K_i$=0.0007 µM; Compound 250, $K_i$=0.0004 µM; Compound 251, $K_i$=0.0008 µM; and Compound 252, $K_i$=0.0004 µM.

Example 14

Sheep Model of Asthma

The allergic sheep model of asthma was employed for the in vivo evaluation of the compounds of the invention as antiasthmatics. These methods have been published previously (see Abraham et al. (1983) *Am. Rev. Respir. Dis.* 128:839–844; Allegra et al. (1983) *J. Appl. Physiol.* 55:726–730; Russi et al. (1985) *J. Appl. Physiol.* 59:1416–1422; Soler et al. ((1989) *J. Appl. Physiol.* 67:406–413. Each sheep serves as its own control. Body weights for these animals ranged from 20–50 kilograms.

In these studies, 1 mg of Compound 13 was dissolved in 3 mL distilled water, and the total solution delivered as an aerosol 0.5 hours before, 4 hours after, and 24 hours after antigen challenge (total dose=1 mg; n=3). The results of these experiments are summarized in FIG. 1.

Figure 2:
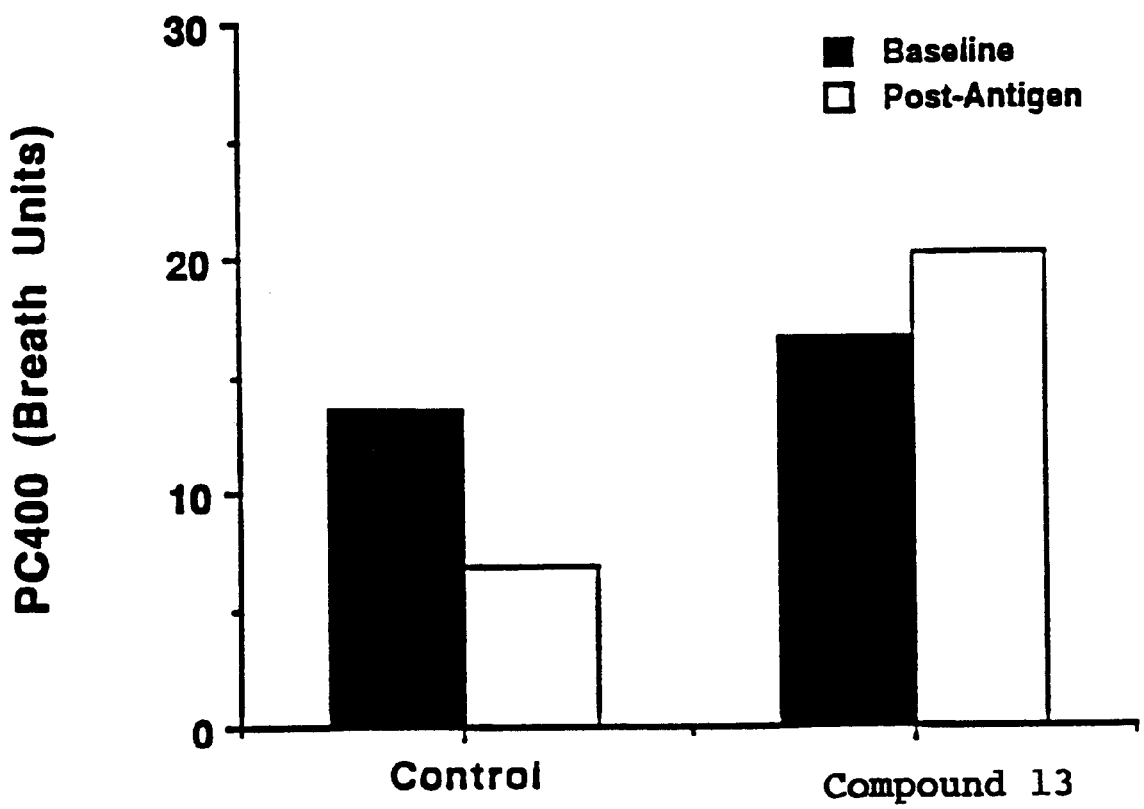
FIG. 2 is a bar chart showing the airway hyper-responsiveness (measured as PC400) antigen-challenged sheep treated with Compound 4 by aerosol administration of three 1 mg doses versus sheep treated with a control.

Twenty-four hours after antigen challenge in both the control and drug trial, the sheep developed airway hyper-responsiveness. Airway hyper-responsiveness is expressed as PC400, the concentration of carbachol that causes a 400% increase in SRL; therefore, a decrease in PC400 indicates hyper-responsiveness. Compound 13 was found to block the onset of hyper-responsiveness. As shown in FIG. 2, this compound maintained the PC400 at substantially the baseline value of 15 breath units. The number of breath units fell to 7 for those animals in the control group. Thus, treatment with Compound 13 resulted in a significant improvement in airway function in antigen challenged sheep.

Thus, the present invention provides compounds and compositions that are useful for the prevention and treatment of immunomediated inflammatory disorders, particularly those associated with the respiratory tract, including asthma, and the hyper-responsiveness phase associated with chronic asthma, in addition to allergic rhinitis. The present invention is also recognized as providing a method for treating immunomediated inflammatory disorders that are susceptible to treatment with a compound of the present invention.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

We claim:

1. A compound having the formula:

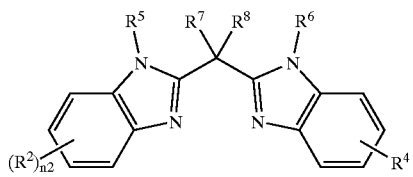

in which:
n2 is 1, 2 or 3;
each $R^2$ is independently a halogen;
$R^4$ is —C(O)NH—$X^6$—($R^{15}$) wherein:
  $X^6$ is ($C_{1-4}$)alkylene or hetero($C_{2-4}$)alkylene;
  $R^{15}$ is ($C_{6-14}$)aryl optionally substituted with one to three sub substituents independently selected from ($C_{1-4}$)alkyl, ($C_{1-4}$)alkyloxy, ($C_{1-4}$)alkyloxycarbonyl, carboxy, carbamoyl, halo, hydroxy and tetrazol-1-yl;
$R^5$ is hydrogen or ($C_{1-4}$)alkyl;
$R^6$ is hydrogen or ($C_{1-4}$)alkyl, which alkyl is optionally substituted with one to two substituents independently selected from ($C_{1-4}$)alkyloxy, hydroxy and sulfo;
$R^7$ is hydrogen or ($C_{1-6}$)alkyl; and
$R^8$ is hydrogen or ($C_{1-6}$)alkyl;
or an N-oxide derivative, prodrug derivative, protected derivative, individual isomer, mixture of isomers or a pharmaceutically acceptable salt thereof.

2. The compound of claim 1 which is selected from:
2-(2-{2-[1-(4,6,7-trifluoro-1H-benzoimidazol-2-yl)ethyl]-3-methyl-3H-benzoimidazol-5-ylcarbonylamino}ethoxy)benzoic acid; and
2-(2-{2-[1-(5,6-difluoro-1H-benzoimidazol-2-yl)ethyl]-3-methyl-3H-benzoimidazol-5-ylcarbonylamino}ethoxy)benzoic acid; or an N-oxide derivative, prodrug derivative, protected derivative, individual isomer, mixture of isomers or a pharmaceutically acceptable salt thereof.

3. A pharmaceutical composition comprising the compound of claim 1 in combination with a pharmaceutically acceptable carrier.

4. The pharmaceutical composition in accordance with claim 3, further comprising a β-adrenergic agonist compound.

5. The pharmaceutical composition in accordance with claim 4, wherein said β-adrenergic agonist compound is selected from the group consisting of albuterol, terbutaline, formoterol, fenoterol and prenaline.

6. The pharmaceutical composition in accordance with claim 3, wherein said composition comprises a pharmaceutically acceptable topical carrier.

7. The pharmaceutical composition in accordance with claim 3, wherein said composition comprises a pharmaceutically acceptable oral carrier.

8. The pharmaceutical composition in accordance with claim 3, wherein said composition comprises a pharmaceutically acceptable aerosol carrier.

9. A compound having the formula:

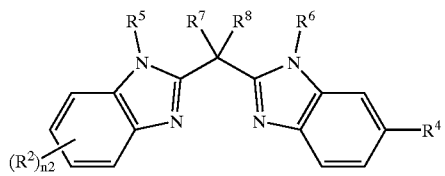

in which:
n2 is 1, 2 or 3;
each $R^2$ is independently a halogen;
$R^4$ is —C(O)NH—$X^6$—($R^{15}$) wherein:
  $X^6$ is ($C_{1-4}$)alkylene or hetero($C_{2-4}$)alkylene;
  $R^{15}$ is ($C_{6-14}$)aryl optionally substituted with one to three substituents independently selected from ($C_{1-4}$)alkyl, ($C_{1-4}$)alkyloxy, ($C_{1-4}$)alkyloxycarbonyl, carboxy, carbamoyl, halo, hydroxy and tetrazol-1-yl;
$R^5$ is hydrogen or ($C_{1-4}$)alkyl;
$R^6$ is hydrogen or ($C_{1-4}$)alkyl;
$R^7$ is hydrogen or methyl; and
$R^8$ is hydrogen or methyl.

10. The compound of claim 9 which is selected from:
2-(2-{2-[1-(4,6,7-trifluoro-1H-benzoimidazol-2-yl)ethyl]-3-methyl-3H-benzoimidazol-5-ylcarbonylamino}ethoxy)benzoic acid; and
2-(2-{2-[1-(5,6-difluoro-1H-benzoimidazol-2-yl)ethyl]-3-methyl-3H-benzoimidazol-5-ylcarbonylamino}ethoxy)benzoic acid.

11. A pharmaceutical composition comprising the compound of claim 9 in combination with a pharmaceutically acceptable carrier.

12. The pharmaceutical composition in accordance with claim 11, further comprising a β-adrenergic agonist compound.

13. The pharmaceutical composition in accordance with claim 12, wherein said β-adrenergic agonist compound is selected from the group consisting of albuterol, terbutaline, formoterol, fenoterol and prenaline.

14. The pharmaceutical composition in accordance with claim 11, wherein said composition comprises a pharmaceutically acceptable topical carrier.

15. The pharmaceutical composition in accordance with claim 11, wherein said composition comprises a pharmaceutically acceptable oral carrier.

16. The pharmaceutical composition in accordance with claim 11, wherein said composition comprises a pharmaceutically acceptable aerosol carrier.

* * * * *